(12) United States Patent
Artusi et al.

(10) Patent No.: US 10,125,121 B2
(45) Date of Patent: Nov. 13, 2018

(54) FYN KINASE INHIBITORS

(71) Applicant: ROTTAPHARM BIOTECH S.R.L., Monza (IT)

(72) Inventors: Roberto Artusi, Rho (IT); Gianfranco Caselli, Milan (IT); Lucio Rovati, Monza (IT)

(73) Assignee: ROTTAPHARM BIOTECH S.R.L., Monza (IT)

( * ) Notice: Subject to any disclaimer, the term of this patent is extended or adjusted under 35 U.S.C. 154(b) by 0 days.

(21) Appl. No.: 15/559,341

(22) PCT Filed: Dec. 23, 2015

(86) PCT No.: PCT/EP2015/081124
§ 371 (c)(1),
(2) Date: Sep. 18, 2017

(87) PCT Pub. No.: WO2016/146220
PCT Pub. Date: Sep. 22, 2016

(65) Prior Publication Data
US 2018/0111919 A1 Apr. 26, 2018

(30) Foreign Application Priority Data
Mar. 18, 2015 (EP) .................... 15159604

(51) Int. Cl.
| | | |
|---|---|---|
| *C07D 403/12* | (2006.01) |
| *C07D 413/14* | (2006.01) |
| *C07D 401/14* | (2006.01) |
| *C07D 403/14* | (2006.01) |
| *A61P 19/02* | (2006.01) |
| *A61P 25/04* | (2006.01) |

(52) U.S. Cl.
CPC ............ *C07D 403/12* (2013.01); *A61P 19/02* (2018.01); *A61P 25/04* (2018.01); *C07D 401/14* (2013.01); *C07D 403/14* (2013.01); *C07D 413/14* (2013.01)

(58) Field of Classification Search
CPC .. C07D 403/12; C07D 413/14; C07D 401/14; C07D 403/14
See application file for complete search history.

(56) References Cited

FOREIGN PATENT DOCUMENTS

WO   WO-2007023382 A2 *  3/2007  ........... C07D 401/14

OTHER PUBLICATIONS

Dimauro et al., "Structure-Guided Design of Aminopyrimidine Amides as Potent, Selective Inhibitors of Lymphocyte Specific Kinase: Synthesis, Structure-Activity Relationships, and Inhibition of in Vivo T Cell Activation", J. Med. Chem 51(6):1681-1694 (2008).

Hanke et al., "Discovery of a Novel Potent, and SRC Family-Selective Tyrosine Kinase Inhibitor", J. Biol. Chem. 271(2):695-701 (1996).

Schenone et al., "FYN Kinase in Brain Diseases and Cancer: The Search for Inhibitors", Current Medicinal Chemistry 18:2921-2942 (2011).

PCT International Search Report and Written Opinion for corresponding PCT/EP2015/081124, dated Mar. 31, 2016.

* cited by examiner

*Primary Examiner* — Matthew P Coughlin
(74) *Attorney, Agent, or Firm* — LeClairRyan PLLC

(57) ABSTRACT

The invention relates to new selective FYN kinase inhibitors of Formula (I), pharmaceutical compositions containing them, and their use for the pharmacological treatment of pain and arthritis, including osteoarthritis and rheumatoid arthritis.

15 Claims, 3 Drawing Sheets

FYN KINASE INHIBITORS

This application is a national stage application under 35 U.S.C. § 371 of PCT Application No. PCT/EP2015/081124, filed Dec. 23, 2015, which claims priority of Europe Application No. 15159604.6, filed Mar. 18, 2015.

FIELD OF THE INVENTION

The present invention relates to new chemical compounds that inhibit protein kinase and methods of making and using the same. Specifically, the present invention relates to new chemical compounds as FYN kinase inhibitors

BACKGROUND OF THE INVENTION

Osteoarthritis (OA) is a group of overlapping distinct diseases, which may have different etiologies but similar biologic, morphologic, and clinical outcomes. The disease process not only affects the articular cartilage, but involves the entire joint, including the subchondral bone, ligaments, capsule, synovial membrane, and periarticular muscles. Ultimately, the articular cartilage degenerates with fibrillation, fissures, ulceration, and full thickness loss of the joint surface. This condition is characterised by focal areas of loss of articular cartilage within synovial joints, associated with hypertrophy of bone (osteophytes and subchondral bone sclerosis) and thickening of the capsule. It may be interpreted as the reaction of synovial joints to injury. This phenomenon can occur in any joint, but is most common in selected joints of the hand, spine, knee, foot and hip. This pathological change, when severe, results in radiological changes (loss of joint space and osteophytes), which have been used in epidemiological studies to estimate the prevalence of OA at different joint sites. The molecular and cellular mechanisms at the basis of the onset of OA are, at present, unknown; it is hypothesised that abnormal load as well as trauma may have a role, but it seems certain that genetics and heritable factors are also involved. Inflammation, when present, is only secondary to a primary event. OA is the most common form of arthritis. The World Health Organization (WHO) estimates that, worldwide, 9.6% of men and 18% of women aged over 60 years have symptomatic OA, classifying OA as the 4th cause of disability in women and the 8th cause in men. It is considered that the risk of disability is the same for knee OA as for cardiac disease. Ultimately OA, due to the underlying process, which consists of an imbalance in cartilage matrix synthesis and breakdown, leading to the destruction of the articular cartilage, results in restricted joint movement, joint instability, pain and chronic disability.

While symptoms, in particular pain, can be controlled by a series of analgesic compounds (from paracetamol to NSAIDS, from opiate to NGF antagonists), it is know that none of these drugs are able to slow the disease progression. On the contrary, strong analgesic compounds could even worsen the underlying pathology (Caso di NGF). What is needed in the art are alternative or supplemental therapies, able of modifying the progressive destruction of cartilage that lastly will conduce to surgical joint replacement.

FYN is acytoplasmatic tyrosine kinase belonging to the Src family kinases that consists of 11 members in humans, including Blk, Brk, Fgr, Frk, Hck, Lck, Lyn, c-Src, Srm and c-Yes (Manning, G. et al., Science, 2002, 298, 1912). FYN has been identified and characterised in 1988 both in normal and transformed cells (Kypta, R. M. et al., EMBO J., 1988, 7, 3837-3844). It is primarily localised to the cytoplasmatic side of the plasma membrane, where it phosphorylates tyrosine residues of enzymes involved in different signalling pathways and works downstream of several cell-surface receptors.

A number of biological functions in which FYN activity is involved has been reported and includes growth factor and cytokine receptor signalling, ion channel function, platelet activation, T cell and B-cell receptor signalling, axon guidance, entry into mitosis, differentiation of natural killer cells, as extensively reported in a recent and complete review (Saito, Y. Et al., Cancer, 2010, 116, 1629).

FYN is primarily involved in several transduction pathways in the central nervous system (CNS) and in the peripheral immune system, playing in this latter important roles in regulation and functions of T-cell development and activation.

FYN overexpression induces morphogenic transformation, alteration of mitogenic signals and stimulation of cell growth and proliferation. FYN is also known to mediate integrin adhesion and cell-cell interactions. For all these reasons, FYN is involved in the onset of cancer (Kawakami T, Proc. Natl. Acad. Sci. U.S.A., 1988, 85, 3870).

For a summary of FYN activity and the status of FYN specific inhibitors a review has been published by Schenone S. on Current Medicinal Chemistry, 2011, 18, 2921.

In the publication Erin F Dimaro et al: "Structure-Guided Design of Aminopyrimidine Amides as Potent, Selective Inhibitors of Lymphocyte Specific Kinase:Synthesis, Structure-Activity Relationships, and Inhibition of in Vivo T Cell Activation" Journal of Medicinal Chemistry, American Chemical Society, vol 51, no. 6, Mar. 1, 2008, pages 1681-1694, Fyn-kinases inhibitors having structure of Aminopyrimidine amides are described.

Then, it is an object of the present invention, to provide FYN kinase inhibitors.

SUMMARY OF THE INVENTION

The objects above indicated have been achieved by a compound of Formula (I):

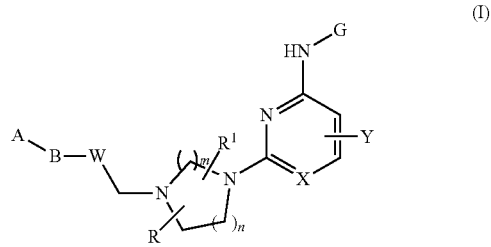

wherein:
A is selected from phenyl, 5-6 membered heterocyclic ring containing one or more hetero atoms selected from N, S and O and a($C_5$-$C_7$)cycloalkyl,
wherein said phenyl is optionally substituted with one or more substituents independently selected from halogen, trifluoromethyl, trifluoromethoxy, ($C_1$-$C_4$)alkyl, ($C_1$-$C_3$) alkoxy, ($C_3$-$C_6$)cycloalkyl, ($C_3$-$C_6$)cycloalkyloxy, nitro, amino, hydroxyl, cyano, carboxamide, sulfonamide, methansulfonyl,
said 5-6 membered heterocyclic ring is a 5-6 membered heteroaryl optionally substituted with one or more substituents independently selected from selected from halogen, trifluoromethyl, trifluoromethoxy, ($C_1$-$C_4$)alkyl, ($C_1$-

$C_3$)alkoxy, ($C_3$-$C_6$)cycloalkyl, ($C_3$-$C_6$)cycloalkyloxy, nitro, amino, hydroxyl, cyano, carboxamide, sulfonamide, methansulfonyl, or a 5 membered heterocyclic ring optionally substituted with ($C_1$-$C_3$)alkyl;

said ($C_5$-$C_7$)cycloalkyl is optionally substituted independently with one or two ($C_1$-$C_4$)alkyl;

B is independently selected from —CONH—, —NHCO—, —SO$_2$NH—, —NHCONH—;

W is phenyl or heteroaryl group comprising one or two heteroatoms selected from N, O and S, being said phenyl or said heteroaryl optionally substituted independently with one or two ($C_1$-$C_4$)alkyl, ($C_1$-$C_3$)alkoxy, ($C_3$-$C_6$) cycloalkyl, ($C_3$-$C_6$)cycloalkyloxy;

R and R$^1$ independently are selected from a group consisting of H, ($C_1$-$C_3$)alkyl and ($C_1$-$C_3$)alkoxy;

m is 1 or 2;

n is 1 or 2;

X is N or C;

Y is independently selected from H, CH$_3$, CH$_2$—OH, CN;

G is a 5-6 membered heteroaryl group, comprising one or more heteroatoms selected from N, O and S, and optionally substituted with one or more substituents independently selected from halogen, ($C_1$-$C_4$)alkyl, ($C_3$-$C_6$)cycloalkyl, or a salt, particularly a pharmaceutically acceptable salt, thereof.

The present invention is further directed to a compound or a salt, particularly a pharmaceutically acceptable salt, thereof or the use in the inhibition of a FYN kinase. The compounds of the invention are inhibitors of FYN kinase and may be useful for the treatment of FYN kinase-mediated diseases and disorders. Therefore in another aspect the invention relates to the compound of the invention for use in the treatment of FYN kinase-mediated diseases and disorders, particularly arthritis including osteoarthritis, rheumatoid arthritis and psoriatic arthritis, acute and chronic pain, such as: osteoarthritis and rheumatoid arthritis pain, postoperative pain, visceral pain, pain associated with cancer, trigeminal neuralgia, diabetic neuropathy acute and chronic pain, postoperative pain, muscular pain.

Accordingly, the invention is further directed to a method of treating a FYN kinase-mediated disease or condition in a patient which comprises administering to the patient a therapeutically effective amount of a compound according to Formula (I), or a pharmaceutically acceptable salt thereof.

"Treating" or "treatment" is intended to mean at least the mitigation of a disease condition in a patient. The methods of treatment for mitigation of a disease condition include the use of the compounds in this invention in any conventionally acceptable manner, for example for prevention, retardation, prophylaxis, therapy or cure of a mediated disease.

The present invention is also directed to a pharmaceutical composition comprising a compound of the invention or its salt and a pharmaceutically acceptable carrier.

As used herein, "pharmaceutically acceptable excipient" means a material, composition or vehicle involved in giving form or consistency to the composition.

DETAILED DESCRIPTION OF THE INVENTION

Figure 1:
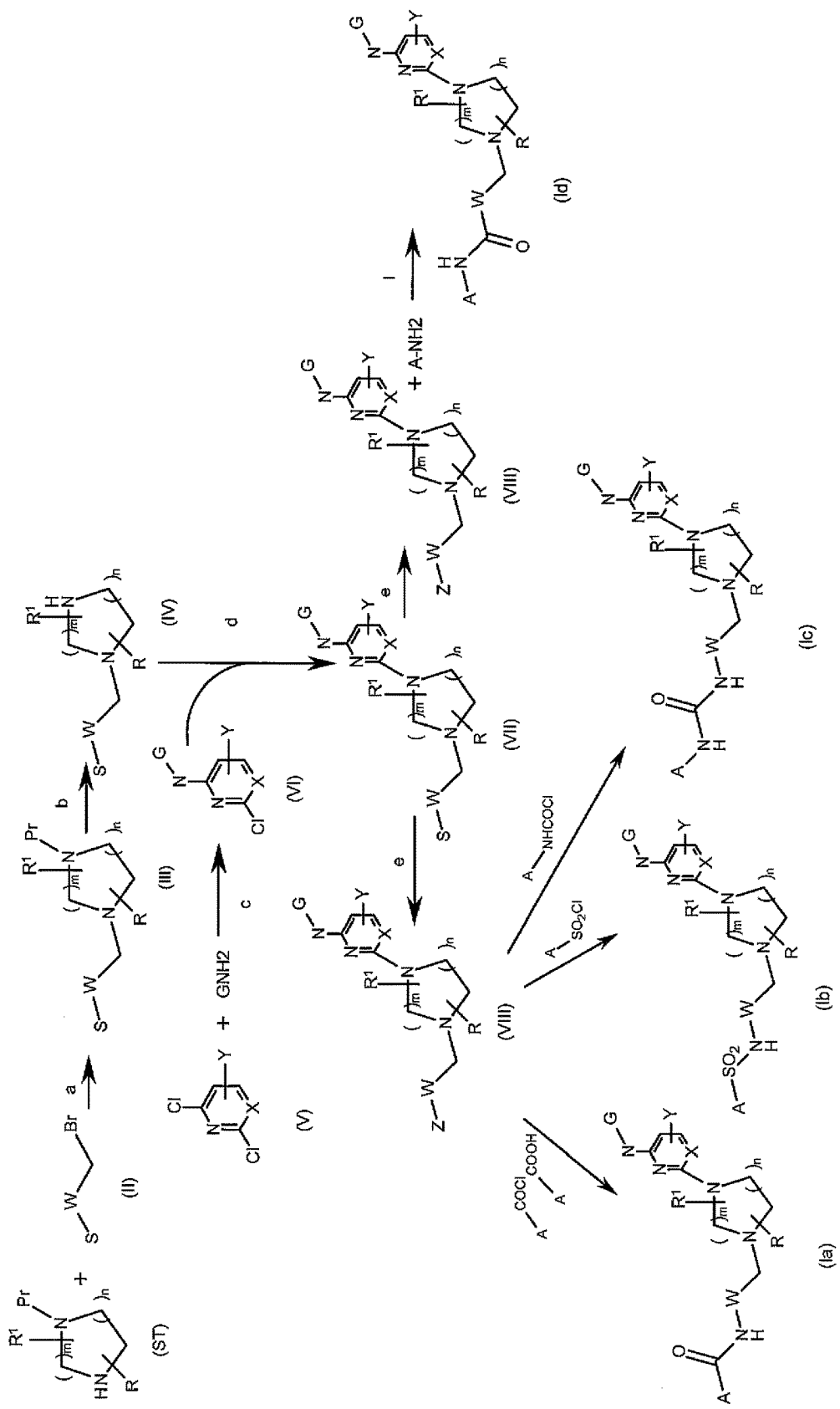
FIG. 1 reports the first and the second embodiments of the process for preparing a compound of Formula (I)

The invention relates to a compound of Formula (I):

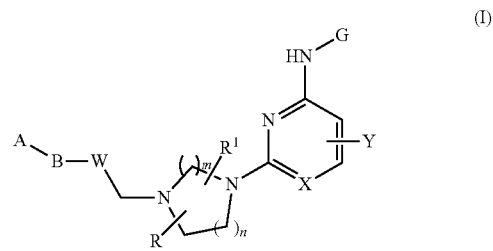

wherein:

A is selected from phenyl, 5-6 membered heterocyclic ring containing one or more hetero atoms selected from N, S and O and a($C_5$-$C_7$)cycloalkyl, wherein said phenyl is optionally substituted with one or more substituents independently selected from halogen, trifluoromethyl, trifluoromethoxy, ($C_1$-$C_4$)alkyl, ($C_1$-$C_3$) alkoxy, ($C_3$-$C_6$)cycloalkyl, ($C_3$-$C_6$)cycloalkyloxy, nitro, amino, hydroxyl, cyano, carboxamide, sulfonamide, methansulfonyl, said 5-6 membered heterocyclic ring is a 5-6 membered heteroaryl optionally substituted with one or more substituents independently selected from selected from halogen, trifluoromethyl, trifluoromethoxy, ($C_1$-$C_4$)alkyl, ($C_1$-$C_3$)alkoxy, ($C_3$-$C_6$)cycloalkyl, ($C_3$-$C_6$)cycloalkyloxy, nitro, amino, hydroxyl, cyano, carboxamide, sulfonamide, methansulfonyl, or a 5-membered heterocyclic ring optionally substituted with ($C_1$-$C_3$)alkyl;

said ($C_5$-$C_7$)cycloalkyl is optionally substituted independently with one or two ($C_1$-$C_4$)alkyl;

B is independently selected from —CONH—, —NHCO—, —SO$_2$NH—, —NHCONH—;

W is phenyl or heteroaryl group comprising one or two heteroatoms selected from N, O and S, being said phenyl or said heteroaryl optionally substituted independently with one or two ($C_1$-$C_4$)alkyl, ($C_1$-$C_3$)alkoxy, ($C_3$-$C_6$) cycloalkyl, ($C_3$-$C_6$)cycloalkyloxy;

R and R$^1$ independently are selected from a group consisting of H, ($C_1$-$C_3$)alkyl and ($C_1$-$C_3$)alkoxy;

m is 1 or 2;

n is 1 or 2;

X is N or C;

Y is independently selected from H, CH$_3$, CH$_2$—OH, CN;

G is a 5-6 membered heteroaryl group, comprising one or more heteroatoms selected from N, O and S, and optionally substituted with one or more substituents independently selected from halogen, ($C_1$-$C_4$)alkyl, ($C_3$-$C_6$)cycloalkyl, or a salt, particularly a pharmaceutically acceptable salt, thereof.

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions.

The compounds according to Formula (I) may contain one or more asymmetric centre (also referred to as a chiral centre) and may, therefore, exist as individual enantiomers, diastereomers, or other stereoisomeric forms, or as mixtures thereof. Chiral centres, such as a chiral carbon may also be present in the compounds of this invention. Where the stereochemistry of a chiral centre present in a compound of this invention, or in any chemical structure illustrated herein, is not specified the structure is intended to encompass all individual stereoisomers and all mixtures thereof. Thus, compounds according to Formula (I) containing one or more chiral centre may be used as racemic mixtures, enantiomerically enriched mixtures, or as enantiomerically pure individual stereoisomers.

It is to be understood that a solid form of a compound of the invention may exist in crystalline forms, non-crystalline forms or a mixture thereof. Such crystalline forms may also exhibit polymorphism (i.e. the capacity to occur in different crystalline forms). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/re-crystallizing the compound.

In addition, the compounds of this invention, depending on further substitution, may exist in other tautomeric forms. All tautomeric forms of the compounds described herein are intended to be encompassed within the scope of the present invention. It is to be understood that any reference to a named compound of this invention is intended to encompass all tautomers of the named compound and any mixtures of tautomers of the named compound.

As used herein, the terms "compound(s) of the invention" or "compound(s) of this invention" mean a compound of Formula (I), as defined above, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

As used herein, the term "optionally substituted" means unsubstituted groups or rings (e.g., cycloalkyl, heterocycloalkyl, and heteroaryl rings) and groups or rings substituted with one or more specified substituents.

Accordingly, a compound of the invention includes a compound of Formula (I), or a salt thereof, particularly a pharmaceutically acceptable salt thereof.

Preferably, A is phenyl. When A is phenyl, it can be substituted with preferably halogen, $(C_1-C_4)$alkyl, $(C_1-C_3)$ alkoxy, trifluoromethyl, trifluoromethoxy, methansulphonyl.

When A is a 5-6 membered heteroaryl group, it is preferably oxazole, piridyl, imidazole, pyrazol and it is optionally substituted with preferably trifluoromethyl, $(C_1-C_3)$ alkyl, trifluoromethoxy, more preferably with trifluoromethoxy.

When A is a 5-membered heterocyclic ring, it is pyrrolidine, optionally substituted preferably with methoxy.

When A is $(C_5-C_7)$cycloalkyl, it is preferably cyclopentyl, optionally substituted with $(C_1-C_4)$alkyl.

R and $R^1$ can be preferably and independently selected from H and $CH_3$. m is preferably 2 and n is preferably 1.

X is preferably N.

According to the present invention, G is preferably 1-H-pyrazol, more preferably substituted with cyclopropyl group.

More preferably the compound of the invention is selected from the group consisting of:

N-(4-((4-(4-((5-cyclopropyl-1H-pyrazol-3-yl)amino)pyrimidin-2-yl)piperazin-1-yl)methyl)phenyl)benzamide, N-(4-((4-(4-((5-cyclopropyl-1H-pyrazol-3-yl)amino)pyrimidin-2-yl)piperazin-1-yl)-methyl)phenyl)-2-(trifluoromethyl)benzamide, N-(4-((4-(4-((5-cyclopropyl-1H-pyrazol-3-yl)amino)pyrimidin-2-yl)piperazin-1-yl)-methyl)phenyl)-2-fluorobenzamide, N-(4-((4-(4-((5-cyclopropyl-1H-pyrazol-3-yl)amino)pyrimidin-2-yl)piperazin-1-yl)-methyl)phenyl)-2-methylbenzamide, 2-chloro-N-(4-((4-(4-((5-cyclopropyl-1H-pyrazol-3-yl)amino)pyrimidin-2-yl)piperazin-1-yl)methyl)phenyl)benzamide, N-(4-((4-(4-((5-cyclopropyl-1H-pyrazol-3-yl)amino)pyrimidin-2-yl)piperazin-1-yl)-methyl)phenyl)-2-isopropylbenzamide, N-(4-((4-(4-((5-cyclopropyl-1H-pyrazol-3-yl)amino)pyrimidin-2-yl)piperazin-1-yl)-methyl)phenyl)-2-methoxybenzamide, N-(4-((4-(4-((5-cyclopropyl-1H-pyrazol-3-yl)amino)pyrimidin-2-yl)piperazin-1-yl)-methyl)phenyl)-2-(trifluoromethoxy)benzamide, N-(4-((4-(4-((5-cyclopropyl-1H-pyrazol-3-yl)amino)pyrimidin-2-yl)piperazin-1-yl)-methyl)phenyl)-3-(trifluoromethyl)benzamide, N-(4-((4-(4-((5-cyclopropyl-1H-pyrazol-3-yl)amino)pyrimidin-2-yl)piperazin-1-yl)-methyl)phenyl)-4-(trifluoromethyl)benzamide, N-(4-((4-(4-((5-cyclopropyl-1H-pyrazol-3-yl)amino)pyrimidin-2-yl)piperazin-1-yl)-methyl)phenyl)-2,4-difluorobenzamide, N-(4-((4-(4-((5-cyclopropyl-1H-pyrazol-3-yl)amino)pyrimidin-2-yl)piperazin-1-yl)-methyl)phenyl)-3-fluoro-2-(trifluoromethyl)benzamide, N-(4-((4-(4-((5-cyclopropyl-1H-pyrazol-3-yl)amino)pyrimidin-2-yl)piperazin-1-yl)-methyl)phenyl)-2-fluoro-6-(trifluoromethyl)benzamide, N-(4-((4-(4-((5-cyclopropyl-1H-pyrazol-3-yl)amino)pyrimidin-2-yl)piperazin-1-yl)-methyl)phenyl)-4-fluoro-2-(trifluoromethyl)benzamide, N-(4-((4-(4-((5-cyclopropyl-1H-pyrazol-3-yl)amino)pyrimidin-2-yl)piperazin-1-yl)-methyl)phenyl)-2-methoxy-4-methylbenzamide, N-(4-((4-(4-((5-cyclopropyl-1H-pyrazol-3-yl)amino)pyrimidin-2-yl)piperazin-1-yl)-methyl)phenyl)-3-(methylsulfonyl)benzamide, N-(4-((4-(4-((5-cyclopropyl-1H-pyrazol-3-yl)amino)pyrimidin-2-yl)piperazin-1-yl)-methyl)-2-methylphenyl)-2-fluorobenzamide, N-(4-((4-(4-((5-cyclopropyl-1H-pyrazol-3-yl)amino)-6-methylpyrimidin-2-yl)piperazin-1-yl)methyl)-2-ethylphenyl)-2-fluorobenzamide, N-(4-((4-(4-((5-cyclopropyl-1H-pyrazol-3-yl)amino)-6-methylpyrimidin-2-yl)piperazin-1-yl)methyl)-3-ethylphenyl)-2-fluorobenzamide, N-(4-((4-(4-((5-cyclopropyl-1H-pyrazol-3-yl)amino)pyrimidin-2-yl)piperazin-1-yl)-methyl)phenyl)-2-methyloxazole-4-carboxamide, N-(4-((4-(4-((5-cyclopropyl-1H-pyrazol-3-yl)amino)pyrimidin-2-yl)piperazin-1-yl)-methyl)phenyl)-2-methyl-5-(trifluoromethyl)oxazole-4-carboxamide, N-(6-((4-(4-((5-cyclopropyl-1H-pyrazol-3-yl)amino)pyrimidin-2-yl)piperazin-1-yl)-methyl)pyridin-3-yl)-2-methyl-5-(trifluoromethyl)oxazole-4-carboxamide, N-(4-((4-(4-((5-cyclopropyl-1H-pyrazol-3-yl)amino)pyrimidin-2-yl)piperazin-1-yl)-methyl)phenyl)-3-methylisoxazole-4-carboxamide, N-(4-((4-(4-((5-cyclopropyl-1H-pyrazol-3-yl)amino)pyrimidin-2-yl)piperazin-1-yl)-methyl)phenyl)picolinamide, N-(4-((4-(4-((5-cyclopropyl-1H-pyrazol-3-yl)amino)pyrimidin-2-yl)piperazin-1-yl)-methyl)phenyl)-3-methylpicolinamide, N-(4-((4-(4-((5-cyclopropyl-1H-pyrazol-3-yl)amino)pyrimidin-2-yl)piperazin-1-yl)-methyl)phenyl)-3-(trifluoromethyl)picolinamide, N-(4-((4-(4-((5-cyclopropyl-1H-pyrazol-3-yl)amino)pyrimidin-2-yl)piperazin-1-yl)-methyl)phenyl)-2-(trifluoromethyl)nicotinamide, N-(4-((4-(4-((5-cyclopropyl-1H-pyrazol-3-yl)amino)pyrimidin-2-yl)piperazin-1-yl)-methyl)phenyl)-2-methoxynicotinamide, N-(4-((4-(4-((5-cyclopropyl-1H-pyrazol-3-yl)amino)pyrimidin-2-yl)piperazin-1-yl)-methyl)phenyl)-4-(trifluoromethyl)nicotinamide, (R)-N-(4-((4-(4-((5-cyclopropyl-1H-pyrazol-3-yl)amino)pyrimidin-2-yl)-2-methyl-piperazin-1-yl)methyl)phenyl)-2-(trifluoromethyl)nicotinamide, (S)-N-(4-((4-(4-((5-cyclopropyl-1H-pyrazol-3-yl)amino)pyrimidin-2-yl)-2-methyl-piperazin-1-yl)methyl)phenyl)-2-(trifluoromethyl)nicotinamide, N-(4-((4-(4-((5-cyclopropyl-1H-pyrazol-3-yl)amino)pyrimidin-2-yl)piperazin-1-yl)-methyl)phenyl)-3-(trifluoromethyl)isonicotinamide, N-(4-((4-(4-((5-cyclopropyl-1H-pyrazol-3-yl)amino)pyrimidin-2-yl)piperazin-1-yl)-methyl)phenyl)-1-methyl-3-(trifluoromethyl)-1H-pyrazole-4-carboxamide, N-(4-((4-(4-((5-cyclopropyl-1H-pyrazol-3-yl)amino)pyrimidin-2-yl)piperazin-1-yl)-methyl)phenyl)-1-methyl-1H-imidazole-2-carboxamide, N-(4-((4-(4-((5-cyclopropyl-1H-pyrazol-3-yl)amino)pyrimidin-2-yl)piperazin-1-yl)-methyl)phenyl)pyrazine-2-carboxamide, N-(4-((4-(4-((5-cyclopropyl-1H-pyrazol-3-yl)amino)pyrimidin-2-yl)piperazin-1-yl)-methyl)phenyl)-3-(trifluoromethyl)pyrazine-2-carboxamide, 4-((4-(4-((5-cyclopropyl-1H-pyrazol-3-yl)amino)pyrimidin-2-yl)piperazin-1-yl)methyl)-N-(4-(trifluoromethoxy)phenyl)benzamide, 4-((4-(4-((5-cyclopropyl-1H-pyrazol-3-yl)amino)pyrimidin-2-yl)piperazin-1-yl)methyl)-N-(3-(trifluoromethyl)phenyl)benzamide, 4-((4-(4-((5-cyclopropyl-1H-pyrazol-3-yl)amino)pyrimidin-2-yl)piperazin-1-yl)methyl)-N-(4-(trifluoromethyl)phenyl)benzamide, N-(4-((4-(4-((5-cyclopropyl-1H-pyrazol-3-yl)amino)pyrimidin-2-yl)piperazin-1-yl)-methyl)phenyl)-2-fluorobenzenesulfonamide, N-(5-((4-(4-((5-cyclopropyl-1H-pyrazol-3-yl)amino)pyrimidin-2-yl)piperazin-1-yl)-methyl)pyrazin-2-yl)-2-(trifluoromethyl)benzamide, N-(6-((4-(4-((5-cyclopropyl-1H-pyrazol-3-yl)amino)pyrimidin-2-yl)piperazin-1-yl)-methyl)pyridazin-3-yl)-2-(trifluoromethyl)benzamide, N-(6-((4-(4-((5-cyclopropyl-1H-pyrazol-3-yl)amino)pyrimidin-2-yl)piperazin-1-yl)-methyl)pyridin-3-yl)-2-(trifluoromethyl)benzamide, N-(4-((4-(4-((5-cyclopropyl-1,3,4-oxadiazol-2-yl)amino)pyrimidin-2-yl)piperazin-1-yl)-methyl)phenyl)-2-(trifluoromethyl)benzamide, N-(4-((4-(4-((4-methoxypyridin-2-yl)amino)pyrimidin-2-yl)piperazin-1-yl)methyl)-phenyl)-2-(trifluoromethyl)benzamide, N-(4-((4-(4-((3-cyclopropyl-1H-pyrazol-5-yl)amino)-6-methylpyrimidin-2-yl)piperazin-1-yl)methyl)phenyl)-2-(trifluoromethyl)benzamide, N-(4-((4-(4-((3-methyl-1H-pyrazol-5-yl)amino)pyrimidin-2-yl)piperazin-1-yl)methyl)-phenyl)-2-(trifluoromethyl)benzamide, N-(4-((4-(4-((5-cyclopropyl-1H-pyrazol-3-yl)amino)pyrimidin-2-yl)piperazin-1-yl)-methyl)phenyl)-2-methyl-pyrrolidine-1-carboxamide, 1-cyclopentyl-3-(4-((4-(4-((3-cyclopropyl-1H-pyrazol-5-yl)amino)pyrimidin-2-yl)-piperazin-1-yl)methyl)phenyl) urea.

Still more preferably the compound of the invention is selected from

N-(4-((4-(4-((5-cyclopropyl-1H-pyrazol-3-yl)amino)pyrimidin-2-yl)piperazin-1-yl)-methyl)phenyl)-2-(trifluoromethyl)benzamide, and N-(4-((4-(4-((5-cyclopropyl-1H-pyrazol-3-yl)amino)pyrimidin-2-yl)piperazin-1-yl)-methyl)phenyl)-3-(trifluoromethyl)picolinamide.

Because the compounds of the invention contain basic moieties, a desired salt form may be prepared by any suitable method known in the art, including treatment of the free base with an inorganic acid, selected from the group consisting of hydrochloric acid, hydrobromic acid, sulphuric acid, nitric acid, phosphoric acid, and the like, or with an organic acid selected from the group consisting of maleic acid, succinic acid, mandelic acid, fumaric acid, malonic acid, salicylic acid, citric acid, tartaric acid, p-toluensulfonic acid.

Because of their potential use in medicine, the salts of the compounds of Formula (I) are preferably pharmaceutically acceptable salts. Salts encompassed within the term "pharmaceutically acceptable salts" refer to non-toxic salts of the compounds of this invention.

The present invention is also directed to a pharmaceutical composition comprising a compound of the invention or its salt and a pharmaceutically acceptable carrier.

The invention relates also to a pharmaceutical compound of Formula (I) or its salt for use as a medicament.

The compounds of the invention may be administered by any suitable route of administration, including both systemic administration and topical administration. Systemic administration includes oral administration, parenteral administration, trans-dermal administration, rectal administration, and administration by inhalation. The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan.

The compounds of the invention will be normally, but not necessarily, formulated into a pharmaceutical composition prior to administration to a patient. The pharmaceutical compositions of the invention are prepared using techniques and methods known to those skilled in the art.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. A dose of the pharmaceutical composition contains at least a therapeutically effective amount of a compound of this invention (i.e., a compound of Formula (I), or a salt, particularly a pharmaceutically acceptable salt, thereof). When prepared in unit dosage form, the pharmaceutical compositions may contain from 1 mg to 1000 mg of a compound of this invention.

The compounds of the invention and the pharmaceutically acceptable excipient or excipients will typically be formulated into a dosage form adapted for administration to the patient by the desired route of administration.

Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) trans-dermal administration such as trans-dermal patches; (4) rectal administration such as suppositories; (5) inhalation such as aerosols and solutions; and (6) topical administration such as creams, ointments, lotions, pastes, sprays and gels.

Suitable pharmaceutically acceptable excipients include the following types of excipients: diluents, fillers, binders, disintegrants, lubricants, granulating agents, coating agents, wetting agents, suspending agents, emulsifiers, sweeteners, flavour masking agents, colouring agents, anti-caking agents, humectants, plasticizers, viscosity increasing agents, antioxidants, preservatives, stabilizers, surfactants, and buffering agents. Suitable diluents and fillers include lactose, sucrose, dextrose, mannitol, sorbitol, starch, cellulose, calcium sulphate, and dibasic calcium phosphate. The oral solid dosage form may further comprise a binder. Suitable binders include starch, gelatin, sodium alginate, alginic acid, guar gum, povidone, and cellulose and its derivatives (e.g. microcrystalline cellulose). The oral solid dosage form may further comprise a disintegrant. Suitable disintegrants include crospovidone, sodium starch glycolate, alginic acid, and sodium carboxymethyl cellulose. The oral solid dosage form may further comprise a lubricant. Suitable lubricants include stearic acid, magnesium stearate, calcium stearate, and talc. Suitable carriers for oral dosage forms include but are not limited to magnesium carbonate, magnesium stearate, talc, lactose, pectin, dextrin, starch, methylcellulose, sodium carboxymethyl cellulose, and the like. Techniques used to prepare oral formulations are the conventional mixing, granulation and compression or capsules filling.

The compounds of the present invention may be also formulated for parenteral administration with suitable carriers including aqueous vehicles solutions (i.e.: saline, dextrose) and/or oily emulsions.

In a still further aspect the invention relates to a compound or a salt, particularly a pharmaceutically acceptable salt, for the use in the inhibition of a FYN kinase.

The compounds of the invention are inhibitors of FYN kinase and may be useful for the treatment of FYN kinase-mediated diseases and disorders.

Therefore in another aspect the invention relates to the compound of the invention for use in the treatment of FYN kinase-mediated diseases and disorders, particularly arthritis including osteoarthritis, rheumatoid arthritis and psoriatic arthritis, acute and chronic pain, such as: osteoarthritis and rheumatoid arthritis pain, postoperative pain, visceral pain, pain associated with cancer, trigeminal neuralgia, diabetic neuropathy acute and chronic pain, postoperative pain, muscular pain.

Accordingly, the invention is further directed to a method of treating a FYN kinase-mediated disease or condition in a patient which comprises administering to the patient a therapeutically effective amount of a compound according to Formula (I), or a pharmaceutically acceptable salt thereof.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate or inhibit the activity of FYN kinase such that a disease condition which is mediated by that activity is reduced, alleviated or prevented. The amount of a given compound that will correspond to such an amount will vary depending upon factors such as the particular compound (e.g., the potency ($IC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the human in need of treatment (e.g., weight), the particular compound and its properties (e.g., pharmaceutical characteristics), disease or condition and its severity and the specific composition and method being used, but can nevertheless be determined by one of skill in the art.

As above stated the compounds of the present invention may be administered orally or parenterally, in a pharmacological effective amount. For all methods of treatment herein discussed for the compounds of formula (I), the daily oral dosage regimen will preferably be from about 0.05 to about 20 mg/Kg of total body weight. It will also be recognized by one of skill in the art that the optimal quantity and spacing of individual dosages of a compound of formula (I) will be determined by the nature and extent of the condition being treated.

Accordingly, appropriate pharmaceutical composition of compounds of formula (I) or their pharmaceutically acceptable salts, optionally together with pharmaceutically acceptable carriers can be used for the treatment of diseases involving destruction of articular cartilage such as traumatic joint injuries, arthritis including osteoarthritis, rheumatoid arthritis and psoriatic arthritis. Furthermore, appropriate pharmaceutical composition of compounds of formula (I) and their pharmaceutically acceptable salts can be used for treatment of different forms of cancer, in particular colon, prostate and lung cancer.

In addition, appropriate pharmaceutical composition of compounds of formula (I) and their pharmaceutically acceptable salts can be used for treatment of acute and chronic pain, including but not limited to inflammatory pain and associated hyperalgesia and allodynia, osteoarthritis pain, postoperative pain, visceral pain, pain associated with cancer, trigeminal neuralgia, acute herpetic and post herpetic neuralgia, neuropathic pain, diabetic neuropathy.

The compounds of Formula (I) may be obtained by using synthetic procedures. In a further aspect the invention relates to a process for preparing a compound of Formula (I).

The process for preparing a compound of Formula (I) comprises the following steps:
a) adding a compound (ST) to a compound of formula (II) in the presence of a base to obtain a compound of formula (III).

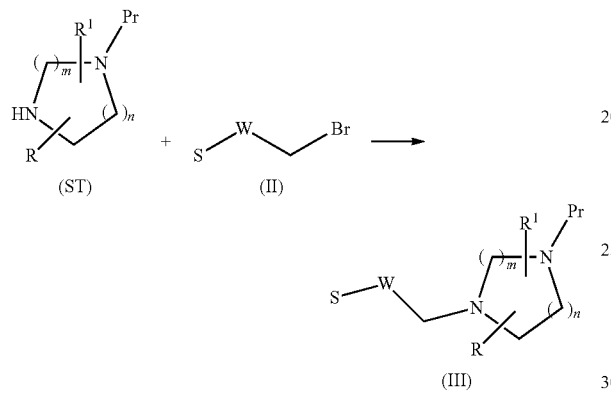

Wherein S is NO$_2$ or COOR$^2$, being said R$^2$ (C$_1$-C$_3$)alkyl
b) removing the protecting group from the compound of Formula (III) to obtain a compound of formula. (IV);

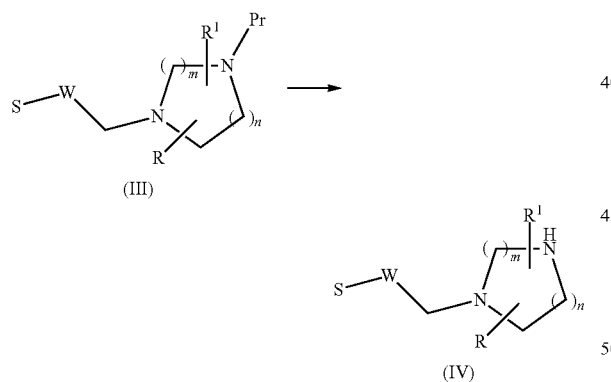

c) adding a compound of formula G-NH$_2$ to a compound of formula (V) in the presence of a base to obtain a compound of formula (VI);

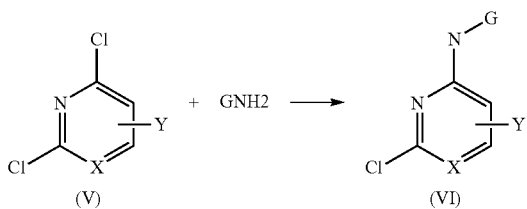

d) adding the compound (IV) to the compound of formula (VI) in the presence of a base to obtain a compound of formula (VII)

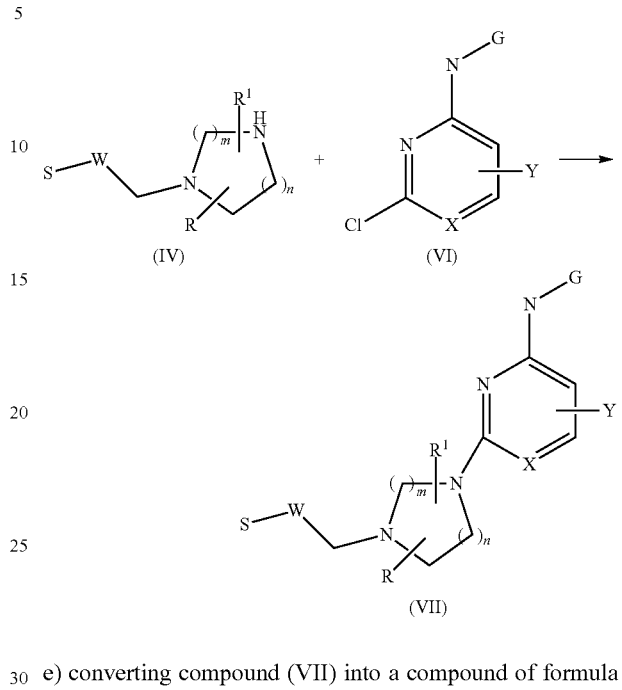

e) converting compound (VII) into a compound of formula (VIII).

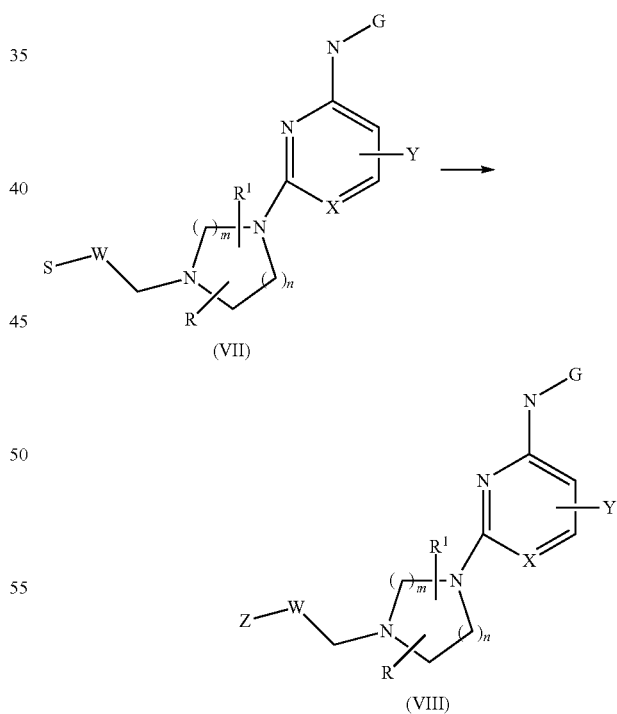

Wherein Z is NH2 or COOH
g) reacting a compound of formula (VIII)
with a compound selected from A-COCl, A-COOH, A-SO$_2$Cl, A-NHCOX, where X is a suitable leaving group, when Z is NH$_2$ or
with A-NH$_2$ when S is COOR$^2$ when Z is COOH, optionally in the presence of a condensing agent, to obtain a compound of formula (I)

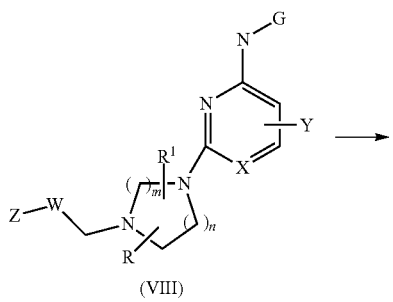

(VIII)

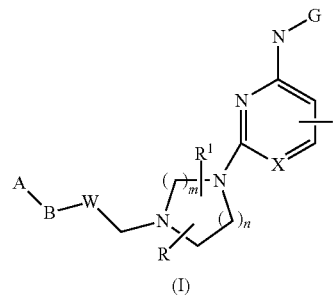

(I)

wherein R, R¹, X, Y, W, G and A have the same meaning as in Formula (I), and Pr is a protecting Group.

In a first embodiment when S in Formula (VII) is $NO_2$, step e) is a reduction to $NH_2$ group, preferably with a suitable reagent as iron, thus obtaining a compound (VIII) wherein Z is $NH_2$.

In this first embodiment step g) comprises reacting the compound of formula (VIII) wherein Z is $NH_2$ with A-COCl or A-COOH, preferably in the presence of a condensing agent, to obtain a compound of formula (Ia)

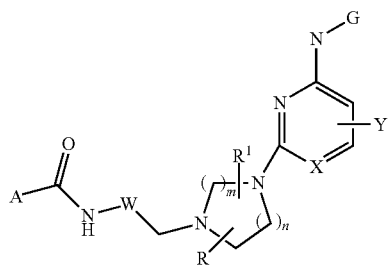

(Ia)

A-$SO_2$Cl, preferably in the presence of a condensing agent, to obtain a compound of formula (Ib)

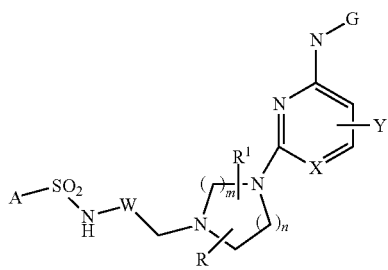

(Ib)

A-NHCOX, where X is a suitable leaving group, preferably in the presence of a condensing agent to obtain a compound of Formula (Ic)

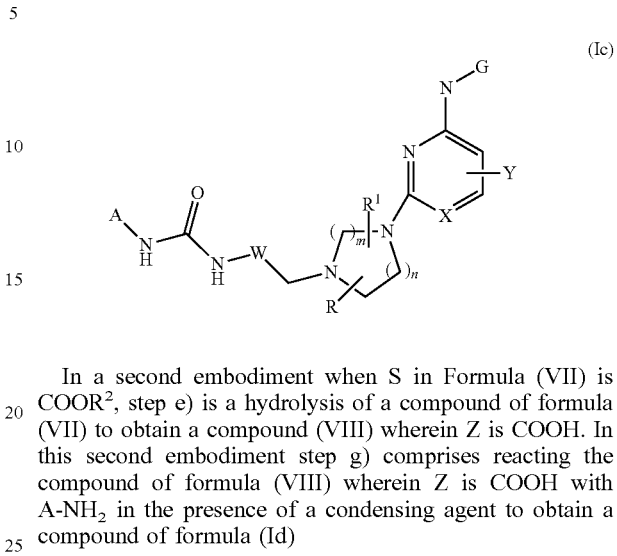

(Ic)

In a second embodiment when S in Formula (VII) is $COOR^2$, step e) is a hydrolysis of a compound of formula (VII) to obtain a compound (VIII) wherein Z is COOH. In this second embodiment step g) comprises reacting the compound of formula (VIII) wherein Z is COOH with A-$NH_2$ in the presence of a condensing agent to obtain a compound of formula (Id)

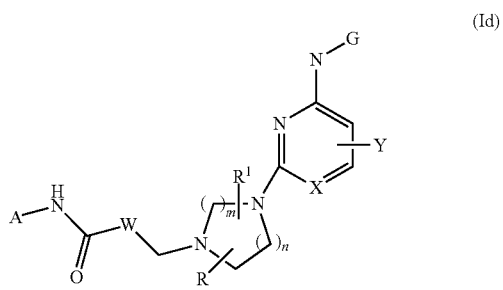

(Id)

A general complete scheme for the first embodiment and the second embodiment of the process of the invention is reported in FIG. 1.

A further aspect of this invention concerns a further process for the preparation of a compound of general formula, comprising the following steps:

a) adding a compound (ST) to a compound of formula (II) in the presence of a base to obtain a compound of formula (III).

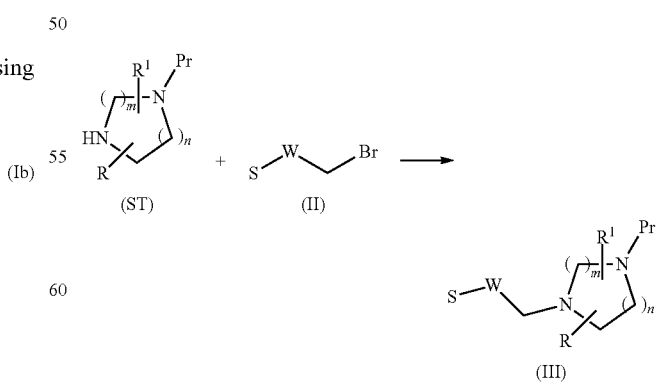

wherein S is $NO_2$ or $COOR^2$, $COOR^2$, being said $R^2$ ($C_1$-$C_3$)alkyl l) converting the compound of formula (III) into a compound of formula (X).

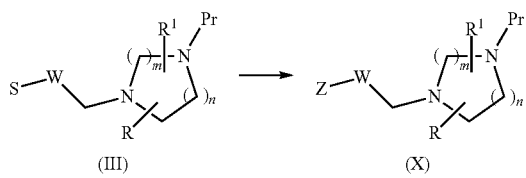

Wherein Z is NH$_2$ or COOH m) reacting a compound of formula (X) with a compound selected from A-COCl, A-COOH, A-SO$_2$Cl, A-NHCOX, where X is a suitable leaving group, when Z is NH$_2$ or with A-NH$_2$ when Z is COOH to obtain a compound of formula (XII).

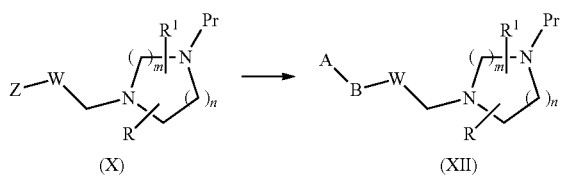

n) removing the protecting group to obtain a compound of formula (XIII).

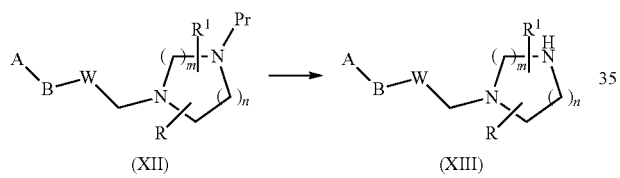

r) reacting the compound of formula (XIII) with a compound of formula (VI) in the presence of a base to obtain a compound of formula (I)

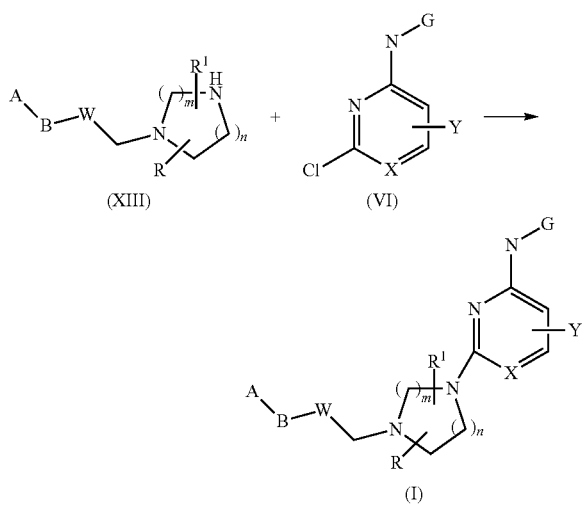

wherein R, R$^1$, X, Y, W, G and A have the same meaning as in Formula (I) and Pr is a protecting Group.

In a third embodiment when S in Formula (III) is NO$_2$, step l) is a reduction to NH$_2$ group, preferably with a suitable reagent as iron, thus obtaining a compound (X) wherein Z is NH$_2$.

In this third embodiment step m) comprises reacting the compound of formula (X) wherein Z is NH$_2$ with A-COCl or A-COOH, preferably in the presence of a condensing agent, to obtain a compound of formula (Ia)

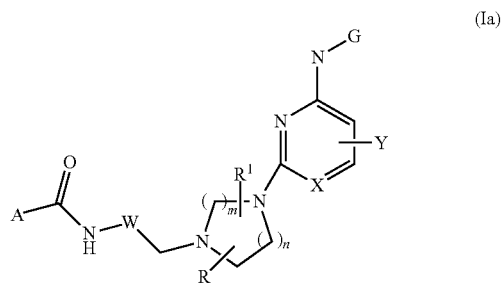

A-SO$_2$Cl, preferably in the presence of a condensing agent to obtain a compound of formula (Ib)

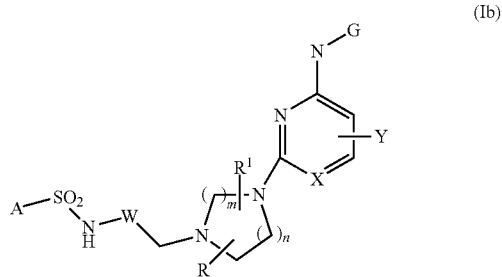

A-NHCOX, where X is a suitable leaving group, preferably in the presence of a condensing agent to obtain a compound of Formula (Ic)

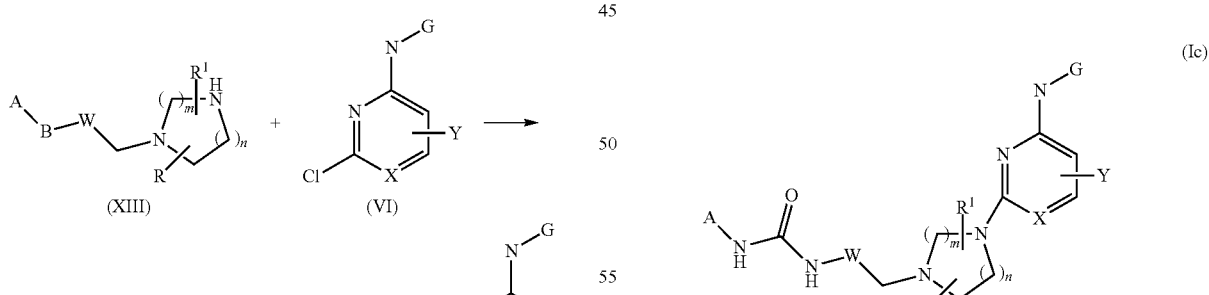

In a fourth embodiment when S in Formula (III) is COOR$^2$, step l) is a hydrolysis of a compound of formula (III) to obtain a compound (X) wherein Z is COOH. In this fourth embodiment step m) comprises reacting the compound of formula (X) wherein Z is COOH with A-NH$_2$, preferably in the presence of a condensing agent to obtain a compound of formula (Id)

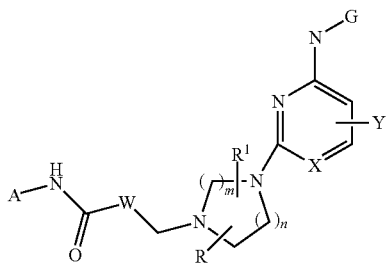

(Id)

Figure 2:
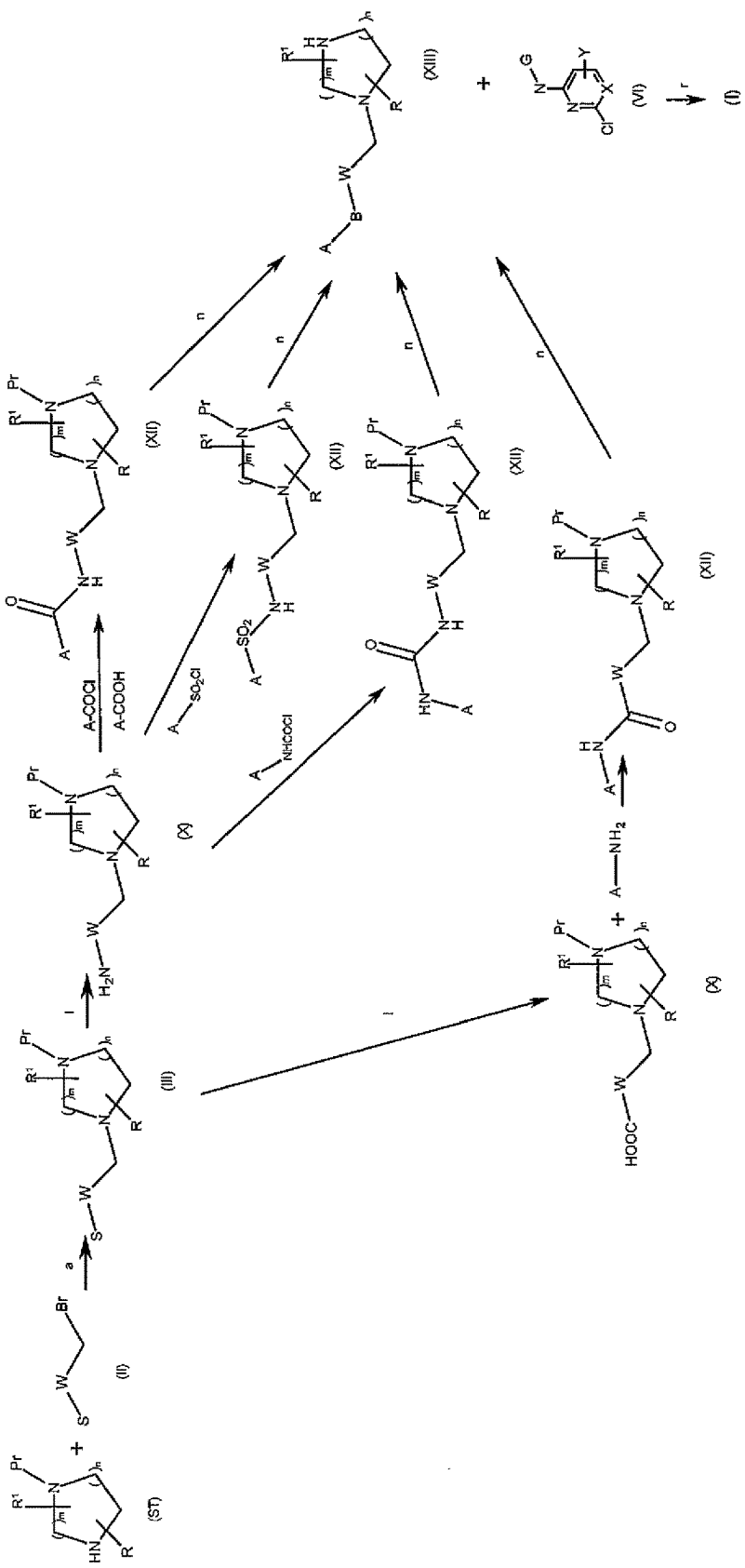
FIG. 2 reports the third and the fourth embodiments of the process for preparing a compound of Formula (I)

The first and the second embodiments of the process of the present invention are reported in FIG. 1 and the third and fourth embodiments are reported in FIG. 2.

The invention will be now described with reference to examples of preparation of the compounds of the invention and examples of absorption.

EXPERIMENTAL PART

Reagents used in the following examples were commercially available from various suppliers and used without further purifications. Solvents were used in dry form. Reactions in anhydrous environment were run under a positive pressure of dry $N_2$. Proton Nuclear Magnetic Resonance ($^1$H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal.

Mass spectra (MS) were run on a Ion Trap Thermo LCQ classic spectrometer, operating in positive ES(+) and negative ES(−) ionization mode.

UPLC spectra were performed on a Waters Acquity UPLC-SQD instrument using an Acquity UPLC-BEH C18 column (1.7 μM, 50×2.1 mm).

HPLC spectra were performed using a Waters Alliance 2965 apparatus and UV-Vis detector Waters 2996. The chromatographic method (using Phenomenex Luna C18, 150*4.6, 5μ) was the following: 35 min of elution at 30° C., mobile phase composed of different acetonitrile/methanol/ $KH_2PO_4$ (20 mM pH 2.5) mixtures, flow rate of 0.6 ml/min.

Flash silica gel chromatography was performed on Biotage automatic flash chromatography systems (Sp1 and Isolera systems) using Biotage SNAP HP silica cartridges or Biotage SNAP KP-NH cartridges.

Reverse phase chromatography was performed on Biotage automatic flash chromatography systems (Isolera systems) using RediSep Gold C-18Aq cartridges. Purifications of some basic compounds were performed using Phenomenex Strata SCX cartridges (55 μm, 70 A).

Thin layer chromatography was carried out using Merck TLC plates Kieselgel 60F-254, visualized with UV light, aqueous permanganate solution, iodine vapours.

The following abbreviations are used herein: DEAD: diethylazodicarboxylate; Boc: terbutyloxycarbonyl; DCM: dichloromethane; TFA: trifluoroacetic acid; DMF: dimethylformamide; THF: tetrahydrofuran; RT: room temperature; DMAP: dimethylamino pyridine; AcOEt: ethyl acetate; NaOH: sodium hydroxyde; KOH: potassium hydroxyde; DIPEA: N,N-diisopropylethylamine; TEA: triethyl amine; $NaHCO_3$: sodium bicarbonate; $Na_2SO_4$: sodium sulphate; Boc: terbutyloxycarbonyl; $Et_2O$: diethyl ether; $CCl_4$: carbon tetrachloride; DCE: dichloroethane MeOH: methanol.EDC HCl: N'-(3-dimethylaminopropyl)-N-ethylcarbodiimide hydrochloride; CDI: di-(1H-imidazol-1-yl)methanone; HOBt: 1H-benzo[d][1,2,3]triazol-1-ol; Pd2(dba)3: 9,9-Dimethyl-4,5-bis(diphenylphosphino)xanthene; Xantphos: Tris(dibenzylideneacetone)dipalladium(0); AIBN: Azobisisobutyronitrile; 1-Propanephosphonic acid cyclic anhydride (T3P).

General Procedure 1

Examples 1-3

Preparation of Intermediate of Formula (III) According to Procedure of FIG. 1

1-(bromomethyl)-4-nitrobenzene (1 mmol) was added to a solution of ter-butyl piperazine-1-carboxylate derivative (1.2 mmol) (Compound (ST) with suitable substitution) and triethylamine (2 mmol) in DCM. The reaction is slightly exothermic. The resulting mixture was left stirring 3 hours at RT. The reaction was diluted with DCM, washed with water and diluted citric acid, dried and evaporated to give the compounds of examples 1, 2, 3.

TABLE 1

| Example | Structure of Intermediate (III) | HNMR/MS | Yield % |
|---|---|---|---|
| 1 | $O_2N$-C$_6$H$_4$-CH$_2$-piperazine-Boc | $^1$H NMR (400 MHz, CDCl3) δ ppm 8.21 (2 H, d), 7.54 (2 H, d), 3.62 (2 H, s), 3.38-3.55 (4 H, m), 2.32-2.52 (4 H, m), 1.48 (10 H, s); ESI+ m/z 322 [M + H]$^+$ | 71 |
| 2 | $O_2N$-C$_6$H$_4$-CH$_2$-(2-methylpiperazine)-Boc (one stereoisomer) | $^1$H NMR (400 MHz, CDCl3) δ ppm 8.16-8.23 (m, 2 H) 7.51-7.58 (m, 2 H), 4.06 (d, 1 H) 3.67 (dt, 1 H) 3.33 (d, 1 H) 3.15 (t, 1 H) 3.03 (d, 2 H) 2.62 (d, 1 H) 2.46-2.57 (m, 1 H) 2.15 (t, 1 H) 1.49 (s, 3 H) 1.48 (s, 9 H) 1.12 (d, 3 H). ESI+ m/z 336 [M + H]$^+$ | 85 |
| 3 | $O_2N$-C$_6$H$_4$-CH$_2$-(2-methylpiperazine)-Boc (opposite stereoisomer) | $^1$H NMR (400 MHz, CDCl3) δ ppm 8.15-8.22 (m, 2 H) 7.54 (m, 2 H) 4.06 (d, 1 H) 3.60-3.70 (m, 1 H) 3.33 (d, 1 H) 3.14 (t, 1 H) 2.89-3.03 (m, 1 H) 2.71-2.89 (m, 1 H) 2.57-2.67 (m, 1 H) 2.51 (dtt, 1 H) 2.15 (t, 1 H) 1.48 (s, 9 H) 1.12 (d, 3 H). ESI+ m/z 336 [M + H]$^+$ | 74 |

General Procedure 2

Examples 4-6

Preparation of Intermediate of Formula (X)
According to Procedure of FIG. 2

To a solution of tert-butyl 4-(4-nitrobenzyl)piperazine-1-carboxylate derivatives (1 mmol) (compound (ST) with suitable substitution) in ethyl acetate (0.12M ml), tin(ii) chloride dihydrate (5 mmol) was added and the resulting mixture was left stirring at RT overnight. Then, saturated aqueous solution of sodium bicarbonate (20 mL) was added and vigorously stirred for 1 hour. Solids were removed by filtration through a celite pad and the organic layer of the filtrate was separated and washed with water (20 mL). The organic phase was dried over anhydrous magnesium sulfate and concentrated to give the following compounds of Formula (X).

completion. The reaction mixture was left to cool to room temperature, washed with a saturated aqueous solution of NH4Cl, then aqueous HCl 0.5 M, aqueous NaOH 1 M and finally with a saturated aqueous solution of NaHCO3. The organic layer was separated, dried over sodium sulphate, filtered and evaporated under vacuum. The resulting crude product was purified by flash chromatography on silica gel, eluting with a gradient from cyclohexane/AcOEt 1/1 to 100% AcOEt. The collected fractions were evaporated to give the compounds of examples 7-10, 14.

3b: Commercially available benzoic acid (1.3 mmol) was suspended in toluene (0.01 M), thionyl chloride (12 mmol) was added and the mixture was heated at 110° C. for 1 h. Volatiles were evaporated and the residue was added to a solution of the intermediate of formula (X) (compounds of examples 4-6 of Table 2) (1 mmol) in pyridine (40 mmol) and the resulting mixture stirred for 1 h at rt. Pyridine was evaporated, then NaOMe (2 mmol) and MeOH were added.

TABLE 2

| Example | Structure of intermediate (X) | HNMR/MS | Yield % |
|---|---|---|---|
| 4 | H2N–C6H4–CH2–piperazine–Boc | 1H NMR (400 MHz, CDCL3) δ ppm 7.11 (2 H, m), 6.66 (2 H, m), 3.65 (2 H, br. s.), 3.43 (6 H, br. s.), 2.38 (4 H, br. s.), 1.47 (10 H, s); ESI+ m/z 292 [M + H]+ | 81 |
| 5 | H2N–C6H4–CH2–(S)-methylpiperazine–Boc | 1H NMR (400 MHz, DMSO-d6) δ ppm 6.92 (m, 2 H) 6.50 (m, 2 H) 4.91 (br. s, 2 H) 3.71 (d, 1 H) 3.42-3.58 (m, 2 H) 2.95-3.07 (m, 2 H) 2.83 (m, 1 H) 2.53-2.59 (m, 1 H) 2.24-2.36 (m, 1 H) 1.90-1.99 (m, 1 H) 1.39 (s, 9 H) 1.04 (d, 3 H); ESI+ m/z 306 [M + H]+ | 100 |
| 6 | H2N–C6H4–CH2–(R)-methylpiperazine–Boc | 1H NMR (400 MHz, DMSO-d6) δ ppm 6.92 (m, 2 H) 6.50 (m, 2 H) 4.91 (br. s, 2 H) 3.71 (d, 1 H) 3.42-3.58 (m, 2 H) 2.95-3.07 (m, 2 H) 2.83 (m, 1 H) 2.53-2.59 (m, 1 H) 2.24-2.36 (m, 1 H) 1.90-1.99 (m, 1 H) 1.39 (s, 9 H) 1.04 (d, 3 H); ESI+ m/z 306 [M + H]+ | 45 |

General Procedure 3

Examples 7-14

Preparation of Intermediate of Formula (XII)
According to Procedure of FIG. 2

3a: In a round bottomed flask under nitrogen atmosphere commercially available benzoic acid (1.1 mmol) or sulphonyl chloride was suspended in 75 ml of anhydrous DCM. Then HOBt (1.4 mmol) and EDC HCl (1.1 mmol) were added and the resulting mixture stirred at room temperature for 2 hours. Then a solution of intermediates (X) (compounds of examples 4-6 of Table 2) (1.1 mmol) in 75 ml of dry DCM was added and the mixture stirred at 40° C. upon After 30 minutes solvent was evaporated and DCM and water were added. The separated organic phase was concentrated and the residue was purified by flash chromatography eluting with DCM/MeOH to give the compounds of examples 11, 12, 13.

3c: Intermediates of formula (X) (compounds of examples 4-6 of Table 2) (1 mmol) and CDI (1 mmol) were dissolved in acetonitrile (Ratio: 1.000, 0.04M) and DCM (Ratio: 0.5, 0.04M). After 2 hours at rt solvents were evaporated, residue dissolved in DMF (Ratio: 0.5, 0.04M) and corresponding amine (1 mmol) was added and the mixture left at 60° C. upon completion. The reaction was then poured in water and extracted with AcOEt (3×); organic phases were collected, washed with water, dried and evaporated to give the title urea (compound of example 15).

TABLE 3

| Example | Structure of intermediate (XII) | HNMR/MS | Procedure Yield % |
|---|---|---|---|
| 7 | 2-CF3-C6H4-C(O)NH-C6H4-CH2-piperazine-Boc | 1H NMR (400 MHz, CDCl3) δ ppm 7.78 (1 H, s), 7.70 (2 H, s), 7.56 (2 H, s), 7.43 (1 H, s), 7.37 (2 H, s), 7.09 (1 H, s), 6.68 (1 H, s), 3.52 (2 H, s), 3.44 (6 H, br. s.), 2.41 (6 H, br. s.), 1.48 (13 H, s) ESI+ m/z 464 [M + H]+ | 3a quantitative |
| 8 | 2-F-C6H4-C(O)NH-C6H4-CH2-piperazine-Boc | 1H NMR (400 MHz, DMSO-d6) δ ppm 10.39 (1 H, s), 10.08 (1 H, s), 9.05-9.21 (1 H, m), 8.30 (1 H, dd), 8.18 (1 H, d), 8.10 (1 H, d), 7.63-7.76 (3 H, m), 7.54-7.63 (1 H, m), 7.26-7.41 (4 H, m), 6.76 (1 H, d), 3.67-3.84 (4 H, m), 3.50 (2 H, s), 2.45 (4 H, t) ESI+ m/z 485 [M + H]+ | 3a 53 |
| 9 | 3-CF3-C6H4-C(O)NH-C6H4-CH2-piperazine-Boc | 1H NMR (400 MHz, CDCl3) δ ppm 8.15 (1 H, s), 8.09 (1 H, d), 7.80-7.90 (2 H, m), 7.58-7.71 (3 H, m), 7.37 (2 H, d), 3.53 (2 H, s), 3.40-3.50 (4 H, m), 2.37-2.46 (5 H, m), 1.48 (9 H, s); ESI+ m/z 464 [M + H]+ | 3a quantitative |
| 10 | 4-CF3-C6H4-C(O)NH-C6H4-CH2-piperazine-Boc | Missing ESI+ m/z 464 [M + H]+ | 3a 88 |
| 11 | pyridin-2-yl-C(O)NH-C6H4-CH2-piperazine-Boc | 1H NMR (400 MHz, DMSO-d6) δ ppm 10.58 (1 H, s), 8.75 (1 H, s), 8.16 (1 H, s), 8.07 (1 H, s), 7.83 (2H, d), 7.68 (1 H, s), 7.27 (2 H, d), 3.38-3.44 (2 H, m), 2.68 (4 H, s), 2.28 (4 H, br. s.), 1.49 (9H, s) ESI+ m/z 396 [M + H]+ | 3b 80 |
| 12 | 2-CF3-pyridin-3-yl-C(O)NH-C6H4-CH2-(2-methyl)piperazine-Boc | 1H NMR (400 MHz, DMSO-d6) d ppm 10.65 (s, 1 H) 8.86 (d, 1 H) 8.20 (d, 1 H) 7.86 (dd, 1 H) 7.61 (d, 2 H) 7.30 (d, 2 H) 3.87 (d, 1 H) 3.42-3.62 (m, 2 H) 3.21 (d, 1 H) 3.00-3.11 (m, 1 H) 2.87 (br. s., 1 H) 2.53-2.61 (m, 1 H) 2.39 (br. s., 1 H) 1.98-2.08 (m, 1 H) 1.35-1.41 (m, 9 H) 1.06 (d, 3 H). ESI+ m/z 479 [M + H]+ | 3b 90 |
| 13 | 2-CF3-pyridin-3-yl-C(O)NH-C6H4-CH2-(2-methyl)piperazine-Boc | 1H NMR (400 MHz, DMSO-d6) d ppm 10.65 (s, 1 H) 8.86 (d, 1 H) 8.20 (d, 1 H) 7.86 (dd, 1 H) 7.61 (d, 2 H) 7.30 (d, 2 H) 3.87 (d, 1 H) 3.42-3.62 (m, 2 H) 3.21 (d, 1 H) 3.00-3.11 (m, 1 H) 2.87 (br. s., 1 H) 2.53-2.61 (m, 1 H) 2.39 (br. s., 1 H) 1.98-2.08 (m, 1 H) 1.35-1.41 (m, 9 H) 1.06 (d, 3 H). ESI+ m/z 479 [M + H]+ | 3b 81 |
| 14 | 2-F-C6H4-S(O)2-NH-C6H4-CH2-piperazine-Boc | 1H NMR (400 MHz, DMSO-d6) δ ppm 10.53 (1 H, br. s.), 7.82 (1 H, t), 7.68 (1 H, d), 7.29-7.47 (2 H, m), 7.15 (2 H, d), 7.05 (2 H, d), 3.35 (2 H, s), 3.27 (4 H, d), 2.22 (4 H, t), 1.38 (9 H, s); ESI+ m/z 450 [M + H]+ | 3a 59 |

TABLE 3-continued

| Example | Structure of intermediate (XII) | HNMR/MS | Procedure Yield % |
|---|---|---|---|
| 15 | (pyrrolidine-C(O)-NH-C6H4-CH2-piperazine-N-Boc) | 1H NMR (400 MHz, DMSO-d6) δ ppm 8.20 (1 H, s), 7.31 (2 H, d), 7.12 (2 H, d), 6.10 (1 H, d), 3.93 (1H, d), 3.37 (2 H, s), 3.30 (4 H, d), 2.24-2.31 (4 H, m), 1.83 (2 H, dd), 1.48-1.69 (4 H, m), 1.30-1.39 (11 H, m); ESI+ m/z 403 [M + H]+ | 3c 16 |

General Procedure 4

Figure 3:
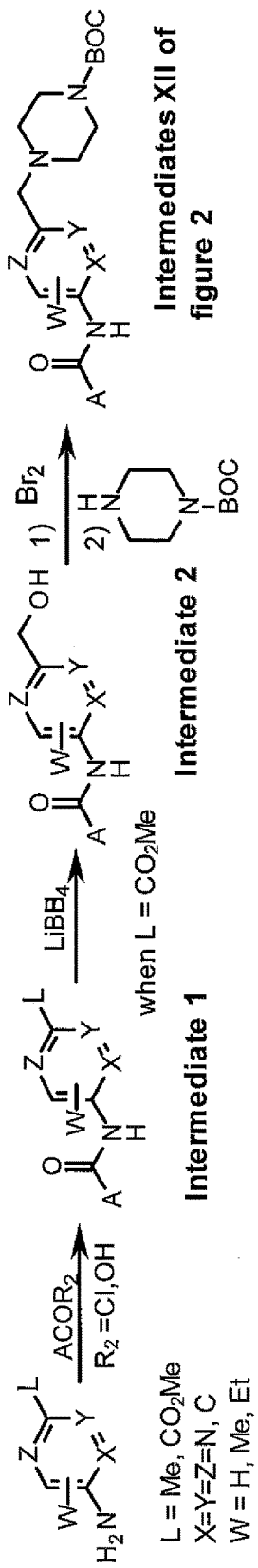
FIG. 3 reports the scheme of preparation of some intermediates of Formula (XII) of FIG. 2.

Some of the intermediates of Formula (XII) of FIG. 2 were prepared according to the procedure reported in FIG. 3

Examples 16-22

Preparation of Intermediate of Formula (1) According to Procedure of FIG. 3

4a: TEA (1.2 mmol) and the commercially available benzoyl chloride (1.1 mmol) were added at 0° C. to a solution of the corresponding aniline (1 mmol) in DCM (0.16M). The reaction mixture was left stirring at room temperature for 2 h. Sat. solution of NaHCO$_3$ (500 ml) was added. The phases were separated and the aqueous layer was extracted with DCM (3 times). The combined organic layers were evaporated and purified by flash chromatography eluting with DCM/EtOAc to obtain the compounds of examples 16-18, 20, 21 reported in Table 4.

4b: A mixture of the corresponding aniline (1 mmol), the commercially available carboxylic acid (1 mmol), (T$_3$P) in DMF (1.2 mmol) and DIPEA (2 mmol) in DMF (0.5M) was stirred at 45° C. upon completion. After that the mixture was diluted with AcOEt and washed twice with water. Organic layer was dried and evaporated and the residue was triturated in diethylether to afford the compounds of examples 19, 22 reported in Table 4.

TABLE 4

| Example | Structure of intermediate (1) | HNMR/MS | Procedure Yield % |
|---|---|---|---|
| 16 | (2-F-C6H4-C(O)-NH-(3-methyl-4-methoxycarbonyl-phenyl)) | $^1$H NMR (400 MHz, DMSO-d$_6$) δ ppm 9.95 (s, 1 H), 7.88 (s, 1 H), 7.87-7.74 (m, 3 H), 7.66-7.58 (m, 1 H), 7.42-7.33 (m, 2 H), 3.86 (s, 3 H), 2.34 (s, 3 H). ESI+ m/z 288 [M + H]+ | 4a 95 |
| 17 | (2-F-C6H4-C(O)-NH-(3-ethyl-4-methoxycarbonyl-phenyl)) | ESI+ m/z 302 [M + H]+ | 4a 79 |
| 18 | (2-F-C6H4-C(O)-NH-(2-ethyl-4-methoxycarbonyl-phenyl)) | 1H NMR (400 MHz, DMSO-d6) δ ppm 10.63 (1 H, s), 7.84 (1 H, d), 7.66-7.74 (3 H, m), 7.57-7.64 (1H, m), 7.32-7.41 (2 H, m), 3.82 (3 H, s), 2.93 (2 H, q), 1.18 (3 H, t); ESI+ m/z 302 [M + H]+ | 4a 74 |

TABLE 4-continued

| Example | Structure of intermediate (1) | HNMR/MS | Procedure Yield % |
|---|---|---|---|
| 19 | | 1H NMR (400 MHz, DMSO-d6) δ ppm 11.13 (1 H, s), 9.11 (1 H, d), 8.44-8.49 (1 H, m), 8.09 (1 H, d), 3.85-3.91 (3 H, m), 2.64 (3 H, s); ESI+ m/z 330 [M + H]+ | 4b 69 |
| 20 | | $^1$H NMR (400 MHz, DMSO-$d_6$) δ ppm 11.29 (s, 1 H), 9.25 (br. s., 1 H), 8.34 (s, 1 H), 7.88-7.82 (m, 1 H), 7.82-7.76 (m, 1 H), 7.73 (d, J = 3.9 Hz, 2 H), 2.49 (s, 3 H); ESI+ m/z 282 [M + H]+ | 4a 66 |
| 21 | | 1H NMR (400 MHz, CHLOROFORM-d) δ ppm 8.24 (1 H, d), 7.74 (1 H, d), 7.67-7.71 (1 H, m), 7.61-7.64 (1 H, m), 7.51-7.59 (2 H, m), 4.07 (3 H, s); ESI+ m/z 326 [M + H]+ | 4a 47 |
| 22 | | 1H NMR (400 MHz, DMSO-d6) δ ppm 11.54 (1 H, s), 8.89 (1 H, d), 8.23-8.45 (2 H, m), 7.81-7.90 (1H, m), 7.62-7.81 (3 H, m), 3.89 (3 H, s) ESI+ m/z 325 [M + H]+ | 4b 77 |

General Procedure 5

Examples 23-28

Preparation of Intermediate of Formula (2) According to Procedure of FIG. 3

To a solution of the esters shown in table 4 (1 mmol) in THF (volume: 0.5M), lithium borohydride 4M in THF (2.5 mmol) was added dropwise. The reaction mixture was left stirring at 50° C. upon completion. After that HCl 2N was added and the mixture was left stirring at 80° C. for an additional hour. The reaction was cooled to room temperature and sat sol of NaHCO$_3$ was added until the pH reached the value of 8. The organic phases was separated and the aqueous extracted with AcOEt (3 times). The organic phases were combined, dried over Na$_2$SO$_4$ and evaporated to obtain a crude which purified by flash chromatography eluting with DCM/MeOH, thus obtaining compounds of examples 23-28.

TABLE 5

| Example | Structure of intermediate (2) | HNMR/MS | Yield % |
|---|---|---|---|
| 23 | | 1H NMR (400 MHz, DMSO-d6) δ ppm 9.76 (s, 1 H), 7.73 (t, J = 7.1 Hz, 1 H), 7.63-7.55 (m, 1 H), 7.43-7.32 (m, 3 H), 7.21 (s, 1 H), 7.16 (d, J = 7.8 Hz, 1 H), 5.14 (br. s., 1 H), 4.47 (br. s., 2 H), 2.27 (s, 3 H) ESI+ m/z 260 [M + H]+ | 52 |

TABLE 5-continued

| Example | Structure of intermediate (2) | HNMR/MS | Yield % |
|---|---|---|---|
| 24 | (structure: 2-fluorobenzamide linked to NH of phenyl ring bearing ethyl and CH2OH) | 1H NMR (400 MHz, DMSO-d6) δ ppm 9.76 (1 H, s), 7.67-7.76 (1 H, m), 7.58 (1 H, d), 7.29-7.43 (3 H, m), 7.24 (1 H, s), 7.17 (1 H, d), 5.15 (1 H, t), 4.49 (2 H, d), 2.65 (2 H, q), 1.17 (3 H, t) ESI+ m/z 274 [M + H]+ | 87 |
| 25 | (structure: 2-fluorobenzamide linked to NH of phenyl ring bearing ethyl and CH2OH) | 1H NMR (400 MHz, DMSO-d6) δ ppm 10.28 (1 H, s), 7.66 (1 H, t), 7.51-7.61 (3 H, m), 7.29-7.38 (3H, m), 5.00 (1 H, t), 4.50 (2 H, d), 2.62 (2 H, q), 1.18 (3 H, t), ESI+ m/z 274 [M + H]+ | 78 |
| 26 | (structure: 2-methyl-5-trifluoromethyl-oxazole-4-carboxamide linked to pyridine-CH2OH) | $^1$H NMR (400 MHz, DMSO-d$_6$) δ ppm 11.10 (s, 1H), 9.09-9.01 (m, 1H), 8.49 (d, J = 8.8 Hz, 1H), 7.71 (d, J = 8.3 Hz, 1H), 4.69 (s, 2H), 2.64 (s, 3H) ESI+ m/z 302 [M + H]+ | 6 |
| 27 | (structure: 2-trifluoromethylbenzamide linked to pyridazine-CH2OH) | 1H NMR (400 MHz, CHLOROFORM-d) δ ppm 8.24 (1 H, d), 7.74 (1 H, d), 7.67-7.71 (1 H, m), 7.61-7.64 (1 H, m), 7.51-7.59 (2 H, m), 4.07 (3 H, s); ESI+ m/z 326 [M + H]+ | 44 |
| 28 | (structure: 2-trifluoromethylbenzamide linked to pyridine-CH2OH) | 1H NMR (400 MHz, DMSO-d6) δ ppm 11.05 (1 H, s), 8.29 (1 H, s), 8.12 (1 H, d), 7.57-7.85 (5 H, m), 5.26 (1 H, t), 4.51 (2 H, d) ESI+ m/z 297 [M + H]+ | 94 |

General Procedure 6

Examples 29-35

Preparation of Intermediate of Formula (XII) According to Procedure of FIG. 2

6a: The alcohols (1 mmol) represented in table 5 were dissolved in DCM (0.1M) and the solution cooled to ° C. prior to addition of tri-bromo-phosphine (1.1 mmol). The resulting mixture was stirred at 0° C. upon completion. After that solvent was evaporated and the residue, dissolved in little volume of DMF and added to a stirred and cooled solution of commercially available tert-butyl piperazine-1-carboxylate (1 mmol) and DIPEA (2 mmol) in DMF (0.1 M). This mixture was then stirred at 0° C. for 2 h and then at RT upon completion. The reaction was partitioned between water and EtOAC, organic phase was separated and washed with water (3 time), dried and concentrated to a crude which was purified by flash chromatography (eluent: cyclohexane/AcOEt).

6b: AIBN (0.3 mmol) was added to a suspension of example 20(1 mmol) and N-bromosuccinimide (1.1 mmol) in CCl4 (0.7M). The reaction mixture was left stirring at 80° C. upon completion. The reaction mixture was taken up into a mixture of DCM/water. The phases were separated and the aqueous layer was extracted with DCM (2 times). The combined organic layers were evaporated to obtain an oil which was dissolved in little volume of DMF and added to a stirred and cooled solution of commercially available tert-butyl piperazine-1-carboxylate (1 mmol) and DIPEA (2 mmol) in DMF (0.1 M). This mixture was then stirred at 0° C. for 2 h and then at RT upon completion. The reaction was partitioned between water and EtOAC, organic phase was separated and washed with water (3 time), dried and concentrated to a crude which was purified by flash chromatography (eluent: cyclohexane/AcOEt).

According to the above procedures 6a and 6b the compounds reported in Table 6 were obtained.

TABLE 6

| Example | Structure | HNMR/MS | Procedure Yield % |
|---------|-----------|---------|-------------------|
| 29 | 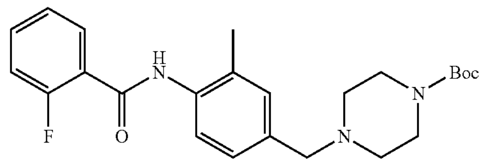 [SMILES: Cc1cc(CN2CCN(C(=O)OC(C)(C)C)CC2)ccc1NC(=O)c1ccccc1F] | 1H NMR (400 MHz, DMSO-d6) δ ppm 11.91 (s, 1 H), 7.88 (d, 1 H), 7.74 (t, 1 H), 7.63-7.55 (m, 1 H), 7.45 (d, 1 H), 7.41-7.31 (m, 2 H), 7.24 (s, 1 H), 7.19 (d, 1 H), 3.70 (2 H, s), 3.48 (2 H, s), 2.43 (4 H, br s), 2.28 (3 H, br s), 1.40 (9 H, s) ESI+ m/z 430 [M + H]+ | 6a 57 |
| 30 | 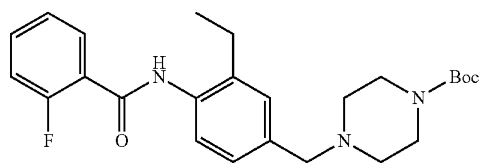 [SMILES: CCc1cc(CN2CCN(C(=O)OC(C)(C)C)CC2)ccc1NC(=O)c1ccccc1F] | 1H NMR (400 MHz, DMSO-d6) δ ppm 11.87 (1 H, s), 7.72 (1 H, t), 7.54-7.66 (1 H, m), 7.30-7.47 (3 H, m), 7.14-7.30 (2 H, m), 3.71 (2h, br s); 3.50 (2 H, s), 2.69 (2 H, q), 2.43 (4 H, s), 1.40 (9 H, s), 1.18 (3 H, t); ESI+ m/z 442 [M + H]+ | 6a 67 |
| 31 | 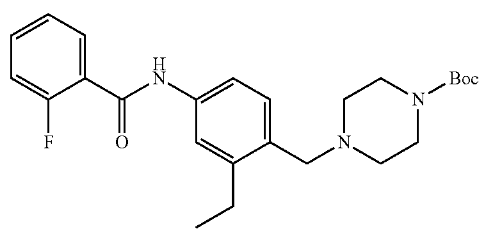 [SMILES: CCc1cc(NC(=O)c2ccccc2F)ccc1CN1CCN(C(=O)OC(C)(C)C)CC1] | 1H NMR (400 MHz, DMSO-d6) δ ppm 10.31 (1 H, s), 7.66 (1 H, t), 7.54-7.61 (2 H, m), 7.52 (1 H, d), 7.30-7.38 (2 H, m), 7.20 (1 H, d), 3.43 (2 H, s), 3.29 (2 H, d), 2.69 (2 H, q), 2.51 (4 H, s), 1.40 (9 H, s), 1.18 (3 H, t); ESI+ m/z 442 [M + H]+ | 6a 56 |
| 32 | 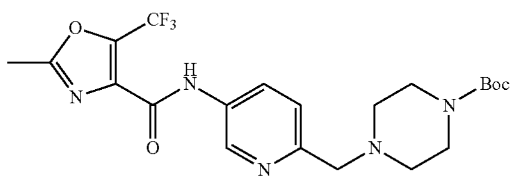 | 1H NMR (400 MHz, DMSO-d6) δ ppm 11.91 (1 H, br. s.), 8.88 (1 H, d), 8.21 (1 H, dd), 7.88 (1 H, d), 7.49 (1 H, d), 3.71 (4 H, br. s.), 3.62 (2 H, s), 2.63 (3 H, s), 2), 1.40 (9 H, s); ESI+ m/z 402 [M + H]+ | 6a 16 |
| 33 | 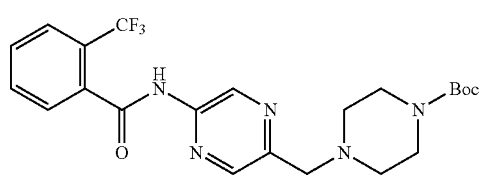 [SMILES: CC(C)(C)OC(=O)N1CCN(Cc2cnc(NC(=O)c3ccccc3C(F)(F)F)cn2)CC1] | 1H NMR (400 MHz, DMSO-d6) δ ppm 11.43 (1 H, br. s.), 8.44 (1 H, s), 7.83-7.88 (1 H, m), 7.77-7.82 (1 H, m), 7.69-7.76 (2 H, m), 3.61 (2 H, s), 2.70 (4 H, t), 2.62 (1 H, s), 2.36 (4 H, br. s.); 1.40 (9 H, s); ESI+ m/z 465 [M + H]+ | 6b 92 |
| 34 | 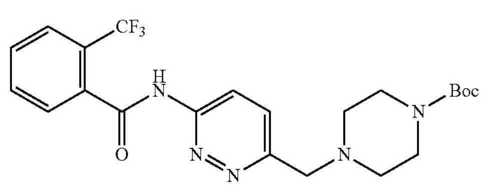 [SMILES: CC(C)(C)OC(=O)N1CCN(Cc2ccc(NC(=O)c3ccccc3C(F)(F)F)nn2)CC1] | 1H NMR (400 MHz, DMSO-d6) δ ppm 11.92 (1 H, br. s.), 8.40 (1 H, d), 7.69-7.99 (6 H, m), 6.33 (1 H, br. s.), 6.06 (1 H, br. s.), 3.61 (2 H, s), 2.70 (4 H, t), 2.62 (1 H, s), 2.36 (4 H, br. s.); 1.40 (9H; s) ESI+ m/z 464 [M + H]+ | 6a 27 |
| 35 | 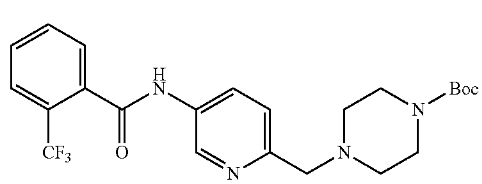 [SMILES: CC(C)(C)OC(=O)N1CCN(Cc2ccc(NC(=O)c3ccccc3C(F)(F)F)cn2)CC1] | 1H NMR (400 MHz, DMSO-d6) δ ppm 11.06 (1 H, br. s.), 8.24 (1 H, br. s.), 8.12 (1 H, d), 7.83 (1 H, d), 7.76 (2 H, d), 7.61-7.72 (2 H, m), 3.44 (2 H, s), 2.69 (4 H, br. s.), 2.30 (4 H, br. s.); ESI+ m/z 465 [M + H]+ | 6a 16 |

General Procedure 7

Examples 36-52

Preparation of Intermediate of Formula (IV) According to Procedure of FIG. 1 and Preparation of Intermediate of Formula (XIII) According to Procedure of FIG. 2

To a solution of Intermediates (XII) (FIG. 2) and Intermediates (III) (FIG. 1) (1 mmol) in DCM (2M), trifluoroacetic acid (10 mmol) was added and the resulting mixture was stirred at RT upon completion. Solvents were evaporated and the residue was purified by SPE-SCX to give the compounds reported in Table 7.

TABLE 7

| Example | Structure of Intermediate (IV) and (XIII) | HNMR/MS | Yield % |
|---|---|---|---|
| 36 | O$_2$N-phenyl-CH$_2$-piperazine-NH | 1H NMR (400 MHz, DMSO-d6) δ ppm 8.19 (2 H, m), 7.59 (2 H, m), 3.56 (2 H, s), 2.70 (4 H, t), 2.30 (4H, br. s.); ESI+ m/z 222 [M + H]+ | 92 |
| 37 | 2-CF$_3$-benzamide-phenyl-CH$_2$-piperazine-NH | 1H NMR (400 MHz, DMSO-d6) δ ppm 10.50 (1 H, s), 7.76-7.89 (2 H, m), 7.65-7.76 (2 H, m), 7.61 (2H, s), 7.26 (2 H, d), 2.60-2.72 (6 H, m), 2.27 (7 H, br. s.); ESI+ m/z 364 [M + H]+ | 95 |
| 38 | 2-F-benzamide-phenyl-CH$_2$-piperazine-NH | 1H NMR (400 MHz, DMSO-d6) δ ppm 10.36 (1 H, s), 7.62-7.73 (3 H, m), 7.53-7.62 (1 H, m), 7.30-7.40 (2 H, m), 7.26 (2 H, d), 3.39 (2 H, s), 2.68 (4 H, t), 2.27 (4 H, br. s.) ESI+ m/z 314 [M + H]+ | 69 |
| 39 | 3-CF$_3$-benzamide-phenyl-CH$_2$-piperazine-NH | 1H NMR (400 MHz, DMSO-d6) δ ppm 10.43 (1 H, s), 8.22-8.35 (2 H, m), 7.97 (1 H, d), 7.79 (1 H, t), 7.71 (2 H, m), 7.29 (2 H, m), 3.40 (2 H, s), 2.68 (4 H, t), 2.28 (4 H, br. s.); ESI+ m/z 364 [M + H]+ | 83 |
| 40 | 4-CF$_3$-benzamide-phenyl-CH$_2$-piperazine-NH | 1H NMR (400 MHz, DMSO-d6) δ ppm 8.14 (2 H, m), 7.91 (2 H, m), 7.71 (2 H, m), 7.28 (2 H, m), 2.69 (9H, br. s.), 2.28 (9 H, br. s.); ESI+ m/z 364 [M + H]+ | 95 |
| 41 | 2-F-benzamide-(2-methyl)phenyl-CH$_2$-piperazine-NH | 1H NMR (400 MHz, DMSO-d6) δ ppm 11.91 (s, 1 H), 7.88 (d, 1 H), 7.74 (t, 1 H), 7.63-7.55 (m, 1 H), 7.45 (d, 1 H), 7.41-7.31 (m, 2 H), 7.24 (s, 1 H), 7.19 (d, 1 H), 3.70 (2 H, s), 3.48 (2 H, s), 2.43 (4 H, br s), 2.28 (3 H, br s) ESI+ m/z 330 [M + H]+ | 95 |
| 42 | 2-F-benzamide-(2-ethyl)phenyl-CH$_2$-piperazine-NH | 1H NMR (400 MHz, DMSO-d6) δ ppm 11.87 (1 H, s), 7.72 (1 H, t), 7.54-7.66 (1 H, m), 7.30-7.47 (3 H, m), 7.14-7.30 (2 H, m), 3.71 (2h, br s); 3.50 (2 H, s), 2.69 (2 H, q), 2.43 (4 H, s), 1.18 (3 H, t); ESI+ m/z 342 [M + H]+ | 90 |

TABLE 7-continued

| Example | Structure of Intermediate (IV) and (XIII) | HNMR/MS | Yield % |
|---|---|---|---|
| 43 | | 1H NMR (400 MHz, DMSO-d6) δ ppm 10.31 (1 H, s), 7.66 (1 H, t), 7.54-7.61 (2 H, m), 7.52 (1 H, d), 7.30-7.38 (2 H, m), 7.20 (1 H, d), 3.43 (2 H, s), 3.29 (2 H, d), 2.69 (2 H, q), 2.51 (4 H, s) ESI+ m/z 342 [M + H]+ | 89 |
| 44 | | 1H NMR (400 MHz, DMSO-d6) δ ppm 11.91 (1 H, br. s.), 8.88 (1 H, d), 8.21 (1 H, dd), 7.88 (1 H, d), 7.49 (1 H, d), 3.71 (4 H, br. s.), 3.62 (2 H, s), 2.63 (3H, s), 2), ESI+ m/z 372 [M + H]+ | 85 |
| 45 | | 1H NMR (400 MHz, DMSO-d6) δ ppm 10.58 (1 H, s), 8.75 (1 H, s), 8.16 (1 H, s), 8.07 (1 H, s), 7.83 (2H, d), 7.68 (1 H, s), 7.27 (2 H, d), 3.38-3.44 (2 H, m), 2.68 (4 H, s), 2.28 (4 H, br. s.) ESI+ m/z 297 [M + H]+ | 88 |
| 46 | | $^1$H NMR (400 MHz, DMSO-d$_6$) δ ppm 10.63 (s, 1 H) 8.86 (d, 1 H) 8.20 (d, 1 H) 7.86 (dd, 1 H) 7.60 (d, 2 H) 7.25-7.33 (m, 2 H) 3.90 (d, 1 H) 3.11 (d, 1 H) 2.75 (dd, 1 H) 2.63-2.71 (m, 1 H) 2.57 (dd, 1 H) 2.49 (br. s., 1 H) 2.31-2.39 (m, 1 H) 2.21-2.31 (m, 1 H) 1.91-2.00 (m, 1 H) 1.04 (d, 3 H) ESI+ m/z 379 [M + H]+ | 90 |
| 47 | | $^1$H NMR (400 MHz, DMSO-d$_6$) δ ppm 10.63 (s, 1 H) 8.86 (d, 1 H) 8.20 (d, 1 H) 7.86 (dd, 1 H) 7.60 (d, 2 H) 7.25-7.33 (m, 2 H) 3.90 (d, 1 H) 3.11 (d, 1 H) 2.75 (dd, 1 H) 2.63-2.71 (m, 1 H) 2.57 (dd, 1 H) 2.49 (br. s., 1 H) 2.31-2.39 (m, 1 H) 2.21-2.31 (m, 1 H) 1.91-2.00 (m, 1 H) 1.04 (d, 3 H) ESI+ m/z 379 [M + H]+ | 58 |
| 48 | | 1H NMR (400 MHz, DMSO-d6) δ ppm 7.80 (1 H, td), 7.57-7.67 (1 H, m), 7.27-7.41 (2 H, m), 7.09 (2H, m), 6.99 (2 H, m), 3.29 (3 H, s), 2.69 (4 H, t), 2.23 (4 H, br. s.) ESI+ m/z 350 [M + H]+ | 99 |
| 49 | | 1H NMR (400 MHz, DMSO-d6) δ ppm 11.43 (1 H, br. s.), 9.30 (1 H, s), 8.44 (1 H, s), 7.83-7.88 (1 H, m), 7.77-7.82 (1 H, m), 7.69-7.76 (2 H, m), 3.61 (2 H, s), 2.70 (4 H, t), 2.62 (1 H, s), 2.36 (4 H, br. s.) ESI+ m/z 366 [M + H]+ | 93 |
| 50 | | 1H NMR (400 MHz, DMSO-d6) δ ppm 11.92 (1 H, br. s.), 8.40 (1 H, d), 7.69-7.99 (6 H, m), 3.82 (2 H, br. s.), 2.70 (4 H, t), 2.36 (4 H, br. s.) ESI+ m/z 366 [M + H]+ | 85 |

TABLE 7-continued

| Example | Structure of Intermediate (IV) and (XIII) | HNMR/MS | Yield % |
|---|---|---|---|
| 51 | | 1H NMR (400 MHz, DMSO-d6) δ ppm 11.06 (1 H, br. s.), 8.24 (1 H, br. s.), 8.12 (1 H, d), 7.83 (1 H, d), 7.76 (2 H, d), 7.61-7.72 (2 H, m), 3.44 (2 H, s), 2.69 (4 H, br. s.), 2.30 (4 H, br. s.) ESI+ m/z 365 [M + H]+ | 75 |
| 52 | | 1H NMR (400 MHz, DMSO-d6) δ ppm 8.20 (1 H, s), 7.29 (2 H, d), 7.11 (2 H, d), 6.11 (1 H, d), 3.86-3.99 (1 H, m), 3.32 (2 H, s), 2.69 (4 H, t), 2.26 (4 H, br. s.), 1.82 (2 H, dt), 1.47-1.69 (4 H, m), 1.36 (2H, dt) ESI+ m/z 303 [M + H]+ | 84 |

Examples 53-57

Preparation of Intermediates of Formula (VI) of FIGS. 1 and 2

General Procedure 8

The GNH2 derivative (FIG. 1) (1 mmol) was dissolved in DMSO (1 ml/mmol) and DIPEA (2 mmol); the reaction was cooled to 0° C. then 2,4-dichloropyrimidine derivative (0.98 mmol) was added in portions. After 2 hours at RT the reaction was poured in cold water and the solid was:

8a: filtered, washed with water (3×100 ml) and dried at 70° C. in vacuum to give the desired compound.

8b: dissolved in EtOAc; the organic phase was washed with water, dried and evaporated. The residue was purified by silica gel chromatography eluting with DCM/AcOEt General Procedure 9

2,4-dichloropyrimidine derivative (1 mmol), GNH2 (1 mmol), Cs$_2$CO$_3$ (4 mmol) and commercially available Pd2(dba)3 (0.02 mmol) were suspended in DME (0.4M) under nitrogen in a microwave tube. Xantphos (0.04 mmol) was added, the tube was capped and subjected to 3 cycles of evacuation-backfilling with nitrogen. The reaction was heated at 105° C. for 1 h, then cooled to RT, filtered and washed with AcOEt and DCM. Solvents were evaporated and the residue purified by flash chromatography eluting with cyclohexane/AcOEt.

| Examples | Intermediate of Formula (VI) | HNMR/MS | Procedure | Yield % |
|---|---|---|---|---|
| 53 | | 1H NMR (400 MHz, DMSO-d6) δ ppm 12.17 (1 H, br. s.), 10.25 (1 H, br. s.), 8.16 (1 H, d), 7.19 (1 H, br. s.), 5.96 (1 H, br. s.), 1.72-2.04 (1 H, m), 0.88-0.99 (2 H, m), 0.65-0.73 (2 H, m) ESI+ m/z 236 [M + H]+ | 8a | 64 |
| 54 | | 1H NMR (400 MHz, DMSO-d6) δ ppm 12.12 (1 H, br. s.), 10.27 (1 H, br. s.), 8.16 (1 H, br. s.), 6.85 (1 H, br. s.), 5.74-6.50 (1 H, m), 2.22 (3 H, s) ESI+ m/z 210 [M + H]+ | 8b | 64 |
| 55 | | 1H NMR (400 MHz, DMSO-d6) δ ppm 12.13 (1 H, br. s.), 10.11 (1 H, br. s.), 7.10 (1 H, br. s.), 5.70-6.21 (1 H, m), 2.27 (3 H, s), 1.83-1.93 (1 H, m), 0.89-0.96 (2 H, m), 0.64-0.72 (2 H, m) ESI+ m/z 250 [M + H]+ | 8b | 36 |

| Examples | Intermediate of Formula (VI) | HNMR/MS | Procedure | Yield % |
|---|---|---|---|---|
| 56 | (structure: 4-methoxypyridin-2-yl amino linked to 2-chloropyrimidin-4-yl) | $^1$H NMR (400 MHz, DMSO-$d_6$) δ ppm 10.57 (1 H, s), 8.34 (1 H, d), 8.17 (1 H, d), 7.83 (1 H, d), 7.17 (1 H, br. s.), 6.72 (1 H, dd), 3.83 (3 H, s) ESI+ m/z 237 [M + H]+ | 9 | 21 |
| 57 | (structure: 5-cyclopropyl-1,3,4-oxadiazol-2-yl amino linked to 2-chloropyrimidin-4-yl) | 1H NMR (400 MHz, DMSO-d6) δ ppm 12.03 (br. s., 1H), 8.56 (d, 1H), 7.81 (d, 1H), 2.22-2.11 (m, 1H), 1.16-1.08 (m, 2H), 1.01-0.94 (m, 2H) ESI+ m/z 237 [M + H]+ | 9 | 24 |

Example 58

Intermediate of Formula (III) of FIG. 1

Preparation of tert-butyl 4-(4-(methoxycarbonyl)benzyl)piperazine-1-carboxylate (intermediate (III) when W=phenyl, S=COOCH3, m=2 n=1 Pr=tert-butylcarboxylate R=H, R$^1$=H)

In a dried two neck round bottomed flask, to a solution of N-(t-Boc)piperazine (1.561 g, 8.38 mmol) and the commercially available methyl 4-(bromomethyl)benzoate (1.6 g, 6.98 mmol) in DCM (Volume: 20 ml), N,N-diethylethanamine (2.92 ml, 20.95 mmol) was added and the resulting mixture left stirring at RT for 2 hours. After this time the mixture was washed with water and sat. NaCl subsequently and the resulting aqueous layer was extracted once with DCM. The combined organic phase was dried on Na$_2$SO$_4$ and concentrated under reduced pressure to give a colorless oil which was purified by flash chromatography eluting with a gradient of cyclohexane/AcOEt. The relevant fractions were collected and concentrated under reduced pressure to afford title compound (1.3 g; 55.7% yield).

$^1$H NMR (400 MHz, CDCl3) δ ppm 8.00 (1H, s), 7.96 (1H, d), 7.56 (1H, d), 7.42 (1H, t), 3.94 (3H, s), 3.57 (2H, s), 3.40-3.49 (4H, m), 2.41 (4H, t), 1.48 (9H, s); ESI+ m/z 335 [M+H]$^+$

Example 59

Intermediate of Formula (IV) of FIG. 1

Preparation of methyl 4-(piperazin-1-ylmethyl)benzoate(intermediate (IV) when S is COOCH3, R=H, R$^1$=H, W=phenyl, m=2 n=1)

In a one neck round-bottomed flask, to a solution of tert-butyl 4-(4-(methoxycarbonyl)benzyl)piperazine-1-carboxylate (1.3 g, 3.89 mmol) in DCM (Volume: 5 ml) cooled at −15° C. perfluoroacetic acid (5 ml, 65.3 mmol) was added and after 15 min stirring at −15° C. the mixture was allowed to reach room temp. After 2 hours stirring at RT the solvent was evaporated under reduced pressure and the residue was dissolved in MeOH and loaded onto a SPE-SCX (10 g) column. After 2 washing column volumes with MeOH the desired compound (847 mg; 93% yield) was eluted with NH3 2M solution in MeOH $^1$H NMR (400 MHz, CDCl3) δ ppm 8.00 (1H, s), 7.95 (1H, d), 7.57 (1H, d), 7.41 (1H, t), 3.94 (3H, s), 3.55 (2H, s), 2.91 (4H, t), 2.43 (4H, br. s.); ESI+ m/z 236 [M+H]+.

Example 60

Intermediate of Formula (VII) of FIG. 1

Preparation of methyl 4-((4-(4-((5-cyclopropyl-1H-pyrazol-3-yl)amino)pyrimidin-2-yl) piperazin-1-yl)methyl)benzoate(intermediate (VII) when S is COOCH3, R=H, R$^1$=H, W=phenyl, m=2 n=1, X is N, G is 5-cyclopropyl-1H-pyrazole, Y is H)

To a solution of 2-chloro-N-(5-cyclopropyl-1H-pyrazol-3-yl)pyrimidin-4-amine (1.26 g; 5.37 mmol) and methyl 4-(piperazin-1-ylmethyl)benzoate (1.9 g; 8.59 mmol) in DMSO (15 ml), DIPEA (2.81 ml; 16.1 mmol) was added. The resulting mixture was heated at 80° C. for 18 hours. After this time the DIPEA was evaporated and the resulting mixture was acidified with AcOH (1 ml) and purified by reverse phase chromatography eluting with water+0.1% AcOH only to acetonitrile+0.1% AcOH only. Relevant fractions were collected and well evaporated. The residue was dry loaded onto a normal phase column and eluted with a gradient cyclohexane\EtOAc to give title compound (VII) (2.1 g; 93% yield).

1H NMR (400 MHz, DMSO-d6) δ ppm 11.91 (1H, br. s.), 9.32 (1H, br. s.), 7.95 (1H, s), 7.82-7.91 (2H, m), 7.63 (1H, d), 7.51 (1H, t), 6.30 (1H, br. s.), 6.03 (1H, br. s.), 3.87 (3H, s), 3.66-3.73 (4H, m), 3.59 (2H, s), 2.43 (3H, t), 1.82-1.91 (1H, m), 0.86-0.93 (2H, m), 0.61-0.67 (2H, m); ESI+ m/z 434 [M+H]+

Example 61

Intermediate of Formula (VIII) of FIG. 1

Preparation of 4-((4-(4-(((5-cyclopropyl-1H-pyrazol-3-yl)amino)pyrimidin-2-yl)piperazin-1-yl)methyl) benzoic acid (intermediate (VIII) when Z is COOH, R=H, $R^1$=H, W=phenyl, m=2 n=1, X is N, G is 5-cyclopropyl-1H-pyrazole, Y is H To a solution of the compound of example 60 (331 mg; 0.761 mmol) in 1,4-dioxane (3 ml) and water (1 ml), lithium hydrate (80 mg; 1.9 mmol) was added and the resulting mixture was stirred at RT for 6 h. Then the solvents were evaporated under reduced pressure and the residue was dissolved in DMSO (2 ml), acidified with AcOH (1 ml), and purified by reverse phase chromatographyeluting with water\acetonitrile. Relevant fraction were collected and evaporated to afford title compound. (44 mg; 76% yield).

$^1$H NMR (400 MHz, DMSO-$d_6$) δ ppm 12.34 (1H, br. s.), 9.31 (1H, br. s.), 7.92 (2H, d), 7.88 (1H, d), 7.48 (2H, d), 6.30 (1H, br. s.), 6.03 (1H, br. s.), 3.70 (4H, br. s.), 3.59 (2H, s), 2.43 (4H, t), 1.81-1.90 (1H, m), 0.86-0.93 (2H, m), 0.61-0.67 (2H, m); ESI+ m/z 420 [M+H]+

Example 62

Intermediate of Formula (VII) of FIG. 1

Preparation of N-(5-cyclopropyl-1H-pyrazol-3-yl)-2-(4-(4-nitrobenzyl)piperazin-1-yl)pyrimidin-4-amine (intermediate (VII) when S is $NO_2$, R=H, $R^1$=H, W=phenyl, m=2 n=1, X is N, G is 5-cyclopropyl-1H-pyrazole, Y is H)

A solution of 2-chloro-N-(5-cyclopropyl-1H-pyrazol-3-yl)pyrimidin-4-amine (7.5 g, 31.8 mmol), 1-(4-nitrobenzyl)-piperazine (example 36) (10.56 g, 47.7 mmol) and DIPEA (16.7 ml, 95 mmol) in DMSO was heated at 100° C. overnight.

The reaction mixture was cooled, poured in water and filtered. The solid was washed twice with MeOH/water 1/1 and dried under vacuum at 60° C. to give 14 g (91% purity, brown solid, yield 95%) of title compound.

$^1$H NMR (400 MHz, DMSO-d6) δ ppm 11.90 (1H, s), 8.21 (2H, s), 8.10 (1H, s), 7.64 (2H, d), 6.69 (1H, br. s.), 5.83 (1H, br. s.), 3.67 (2H, s), 3.51 (4H, br. s.), 2.47 (4H, br. s.), 1.85 (1H, s), 0.91 (3H, br.s.), 0.67 (2H, br. s.); ESI+ m/z 421 [M+H]+

Example 63

Intermediate of Formula (VIII) of FIG. 1

Preparation of 2-(4-(4-aminobenzyl)piperazin-1-yl)-N-(5-cyclopropyl-1H-pyrazol-3-yl)pyrimidin-4-amine (intermediate (VIII) when Z is $NH_2$, R=H, $R^1$=H, W=phenyl, m=2 n=1, X is N, G is 5-cyclopropyl-1H-pyrazole, Y is H)

To a solution of ammonium chloride (15.8 g, 295 mmol) in water and methanol iron (9.16 g, 164 mmol) was added, followed by example 62 (13.8 g, 32.8 mmol). The mixture was heated at 70° C. for 1 h. The hot suspension was filtered through a pad of celite and concentrated. Water and $Et_2O$ were added, the separated aqueous phase was basified with NaOH 32% and the product extracted twice with DCM. The organic layer was dried and concentrated to give 9.64 g (96% purity, brown solid, yield 75%) of title compound.

$^1$H NMR (400 MHz, DMSO-$d_6$) δ ppm 11.91 (1H, br. s.), 9.11 (1H, br. s.), 8.10 (1H, s), 6.86-7.00 (2H, m), 6.59-6.77 (1H, m), 6.52 (2H, d), 5.83 (1H, br. s.), 4.94 (2H, s), 3.46 (4H, br. s.), 2.25-2.45 (4H, m), 1.78-1.91 (1H, m), 0.90 (2H, d), 0.66 (2H, q); ESI+ m/z 391 [M+H]+

Example 64

Preparation of Compound 2-of Table 8

2-(Trifluoromethyl)benzoic acid (0.974 g, 5.12 mmol) was suspended in Toluene (Ratio: 1.000, Volume: 20 ml), thionyl chloride (1.869 ml, 25.6 mmol) was added and the mixture was heated at 90° C. for 1 h. Solvent was evaporated and the residue was added to a solution of 2-(4-(4-aminobenzyl)piperazin-1-yl)-N-(5-cyclopropyl-1H-pyrazol-3-yl) pyrimidin-4-amine (1 g, 2.56 mmol) in pyridine (15 ml, 185 mmol) and the resulting mixture was stirred for 3 h. Pyridine was evaporated, then sodium methoxide (2 g, 37.0 mmol) and methanol (Ratio: 1.500, Volume: 30 ml) were added. After 2 h solvent was evaporated and DCM and water were added. The separated organic phase was concentrated and the residue was purified by fish chromatography (DCM to DCM/MeOH 9/1) to give title compound. (0.9 g; 62.5% yield).

1H NMR (400 MHz, DMSO-d6) δ ppm 11.91 (1H, s), 10.53 (1H, s), 9.31 (1H, br. s.), 7.87 (2H, s), 7.80 (1H, s), 7.54-7.76 (4H, m), 7.32 (2H, d), 6.31 (1H, br. s.), 6.04 (1H, br. s.), 3.69 (4H, br. s.), 3.48 (2H, s), 2.42 (4H, br. s.), 1.87 (1H, s), 0.91 (2H, d), 0.65 (2H, d); ESI+ m/z 563 [M+H]+

Example 65

Preparation of HCl Salt of Compound 2

N-(4-((4-(4-(((5-cyclopropyl-1H-pyrazol-3-yl)amino)pyrimidin-2-yl)piperazin-1-yl)methy)phenyl)-2-(trifluoromethyl)benzamide of compound 2(10 g) was suspended in MeOH (200 ml) and HCl/MeOH 3N (70 ml) was added. It was stirred for 15 minutes (the precipitate was dissolved), then it was concentrated and the residue (50 ml) was added dropwise to acetone (500 ml). The precipitate was filtered, washed with acetone (2×100 ml). and finally dried under high vacuum at 60° C. for 2 h.

1H NMR (400 MHz, DMSO-d6) δ ppm 11.59 (1H, br. s.), 11.12 (1H, br. s.), 10.76 (1H, s), 7.93 (1H, br. s.), 7.77-7.90 (4H, m), 7.72 (2H, t), 7.61 (2H, d), 6.47 (1H, br. s.), 6.23 (1H, br. s.), 4.60 (2H, d), 4.33 (2H, br. s.), 3.59-3.76 (2H, m), 3.51 (2H, d), 3.08-3.27 (2H, m), 1.95 (1H, t), 0.92-0.99 (2H, m), 0.69-0.76 (2H, m); ESI+ m/z 563 [M+H]+

Example 66

General Procedures Used to Prepare Compounds of Inventions (Formula Ia, Ib, Ic, Id):
General Procedure 10 (FIG. 1)
10a: Commercially available benzoic acid (1.3 mmol) was suspended in Toluene (0.01 M), thionyl chloride (10 mmol) was added and the mixture was heated at 110° C. for 1 h. Volatiles were evaporated and the residue was added to a solution of intermediate (VIII) of example 63 (1 mmol) in pyridine (40 mmol) and the resulting mixture stirred for 1 h at rt. Pyridine was evaporated, then NaOMe (2 mmol) and MeOH were added. After 30 minutes solvent was evaporated and DCM and water were added. The separated organic phase was concentrated and the residue was purified by flash chromatography eluting with a gradient DCM/MeOH to give the compound of Formula (Ia) reported in Table 8.

10b: Intermediate VIII of example 63 (1 mmol), HOBt (1.1 mmol) and EDCl (1.1 mmol) were dissolved in DMF (0.1M) and stirred at RT for 30 min. After this time the corresponding benzoic acid (commercially available) (1.1 mmol), was added and the mixture was left stirring at RT overnight. After night, the mixture was poured in water and extracted with EtOAc several times. The combined organic phases were washed one time with NaHCO₃ sat. solution, dried on Na₂SO₄ and concentrated under reduced pressure. The residue was purified by flash chromatography eluting with a gradient DCM:MeOH to afford the compound of Formula (Ib) reported in Table 8.

10c: Intermediate VIII of example 63(1 mmol) and CDI (1 mmol) were dissolved in acetonitrile (Ratio: 1.000, 0.04M) and DCM (Ratio: 0.5, 0.04M). After 2 hours at rt solvents were evaporated, residue dissolved in DMF (Ratio: 0.5, 0.04M) and corresponding amine (1 mmol) was added and the mixture left at 60° C. upon completion. The reaction was then poured in water and extracted with AcOEt (3×); organic phases were collected, washed with water, dried and evaporated to give the the urea compound of Formula (Ic) reported in Table 8.

10d: Intermediate (VIII) of example 61 (1 mmol), 1-hydroxybenzotriazole monohydrate (1.1 mmol) and N'-(3-Dimethylaminopropyl)-N-ethylcarbodiimide hydrochloride (1.1 mmol) were dissolved in DMF (0.1M) and stirred at RT upon completion (about 30 min). After this time the corresponding aniline (1.1 mmol), was added and the mixtures were left stirring at RT overnight. Afternight, the mixtures were poured in water and extracted with EtOAc several times. The combined organic phases were washed one time with NaHCO₃ sat. solution, dried on Na₂SO₄ and concentrated under reduced pressure. The residue was dissolved in DCM and purified by flash chromatography eluting with a gradient DCM:MeOH to afford the compound of Formula (Id) reported in Table 8.

Example 67

General Procedure 11(FIG. 2)

A solution of intermediates (VI), (1 mmol), intermediates (XIII) (1.5 mmol) and DIPEA (3 mmol) in DMSO (0.2M) was heated at 100° C. for 6 h. DIPEA was evaporated and the residue purified by reverse phase chromatography eluting with water+0.1% AcOH only to acetonitrile+0.1% AcOH only. Relevant fractions were collected and organic solvents were well evaporated; NaOH 1 N was added and the product was extracted with DCM, washed with water, dried and evaporated to give the compound of Formula reported in Table 8.

Table reported hence all the prepared compounds of the invention with NMR data.

TABLE 8

| Compound | Examples | Procedure | Yield % |
|---|---|---|---|
| 1 N-(4-((4-(4-((5-cyclopropyl-1H-pyrazol-3-yl)amino)pyrimidin-2-yl)piperazin-1-yl)methyl)phenyl)benzamide | 63 ¹H NMR (400 MHz, DMSO-d6) δ ppm 11.91 (1 H, br. s.), 10.23 (1 H, s), 9.30 (1 H, br. s.), 7.96 (2 H, d), 7.88 (1 H, d), 7.75 (2 H, m), 7.50-7.64 (3 H, m), 7.32 (2 H, m), 6.31 (1 H, br. s.), 6.05 (1 H, br. s.), 3.69 (4 H, br. s.), 3.49 (2 H, s), 2.42 (4 H, br. s.), 1.87 (1 H, t), 0.91 (2 H, d), 0.65 (2 H, d) ESI+ m/z 495 [M + H]⁺ | 10a | 71 |
| 2 N-(4-((4-(4-((5-cyclopropyl-1H-pyrazol-3-yl)amino)pyrimidin-2-yl)piperazin-1-yl)methyl)phenyl)-2-(trifluoromethyl)-benzamide | 53-37; 63 1H NMR (400 MHz, DMSO-d6) δ ppm 11.91 (1 H, s), 10.53 (1 H, s), 9.30 (1 H, br. s.), 7.78-7.90 (3 H, m), 7.68-7.75 (2 H, m), 7.66 (2 H, m), 7.32 (2 H, m), 6.32 (1 H, br. s.), 6.05 (1 H, br. s.), 3.69 (4 H, br. s.), 3.48 (2 H, s), 2.42 (4 H, t), 1.81-1.92 (1 H, m), 0.86-0.95 (2 H, m), 0.62-0.69 (2 H, m) ESI+ m/z 563 [M + H]⁺ | 11 and 10a | 61-28 |

TABLE 8-continued

| Compound | Examples | Procedure | Yield % |
|---|---|---|---|
| 3 | 53-38 | 11 | 53 |

¹H NMR (400 MHz, DMSO-d6) δ ppm 11.91 (1 H, s), 10.38 (1H, s), 9.31 (1 H, br. s.), 7.87 (1 H, d), 7.68 (3 H, s), 7.57 (1 H, br. s.), 7.25-7.42 (4 H, m), 6.34 (1 H, br. s.), 6.05 (1 H, br. s.), 3.69 (4 H, br.s.), 3.49 (2 H, s), 2.41 (4 H, br. s.), 1.87 (1 H, s), 0.91 (2 H, d), 0.65 (2 H, d)
ESI+ m/z 513 [M + H]⁺

N-(4-((4-(4-((5-cyclopropyl-1H-pyrazol-3-yl)amino)pyrimidin-2-yl)piperazin-1-yl)methyl)phenyl)-2-fluorobenzamide

| 4 | 63 | 10a | 63 |
|---|---|---|---|

¹H NMR (400 MHz, DMSO-d6) δ 11.91 (1 H, s), 10.26 (1 H, s), 9.30 (1 H, br. s.), 7.87 (1 H, s), 7.70 (2 H, s), 7.44 (1 H, s), 7.39 (1 H, s), 7.29 (2 H, s), 7.32 (2 H, s), 6.32 (1 H, br. s.), 6.04 (1 H, br. s.), 3.69 (4 H, br. s.), 3.48 (2 H, s), 2.36-2.46 (7 H, m), 1.87 (1 H, br. s.), 0.91 (2 H, d), 0.65 (2 H, d)
ESI+ m/z 509 [M + H]⁺

N-(4-((4-(4-((5-cyclopropyl-1H-pyrazol-3-yl)amino)pyrimidin-2-yl)piperazin-1-yl)methyl)phenyl)-2-methylbenzamide

| 5 | 63 | 10a | 61 |
|---|---|---|---|

¹H NMR (400 MHz, DMSO-d6) δ ppm 11.91 (1 H, s), 10.47 (1 H, s), 9.31 (1 H, br. s.), 7.88 (1 H, d), 7.69 (2 H, m), 7.55-7.62 (2 H, m), 7.52 (1 H, s), 7.46 (1 H, s), 7.32 (2 H, m), 6.31 (1 H, br. s.), 6.05 (1H, br. s.), 3.69 (4 H, br. s.), 3.48 (2 H, s), 2.41 (4 H, br. s.), 1.87 (1 H, t), 0.91 (2 H, d), 0.65 (2 H, d)
ESI+ m/z 530 [M + H]⁺

2-chloro-N-(4-((4-(4-((5-cyclopropyl-1H-pyrazol-3-yl)amino)pyrimidin-2-yl)piperazin-1-yl)methyl)phenyl)benzamide

| 6 | 63 | 10a | 62 |
|---|---|---|---|

¹H NMR (400 MHz, DMSO-d6) δ ppm 11.92 (1 H, br. s.), 10.34 (1 H, s), 9.31 (1 H, br. s.), 7.88 (1 H, d), 7.71 (2 H, d), 7.45 (2 H, d), 7.34-7.40 (1 H, m), 7.20-7.34 (3 H, m), 6.30 (1 H, br. s.), 6.04 (1 H, br. s.), 3.69 (4 H, br. s.), 3.48 (2 H, s), 3.17-3.27 (1 H, m), 2.41 (4 H, br. s.), 1.78-1.96 (1 H, m), 1.15-1.30 (6 H, m), 0.85-0.95 (2 H, m), 0.59-0.71 (2 H, m)
ESI+ m/z 537 [M + H]⁺

N-(4-((4-(4-((5-cyclopropyl-1H-pyrazol-3-yl)amino)pyrimidin-2-yl)piperazin-1-yl)methyl)phenyl)-2-isopropylbenzamide TABLE 8-continued

| Compound | Examples | Procedure | Yield % |
|---|---|---|---|
| 7 | 63 | 10a | 67 |

¹H NMR (400 MHz, DMSO-d6) δ 11.91 (1 H, br. s.), 10.09 (1 H, s), 9.30 (1 H, br. s.), 7.88 (1H, d), 7.59-7.76 (3 H, m), 7.51 (1 H, t), 7.30 (2 H, d), 7.20 (1 H, s), 7.07 (1 H, t), 6.31 (1 H, br. s.), 6.05 (1 H, br. s.), 3.91 (3 H, s), 3.69 (4 H, br. s.), 3.48 (2 H, s), 2.41 (4 H, br. s.), 1.86 (1 H, s), 0.90 (2 H, d), 0.66 (2 H, br. s.)
ESI+ m/z 525 [M + H]+

N-(4-((4-(4-((5-cyclopropyl-1H-pyrazol-3-yl)amino)pyrimidin-2-yl)piperazin-1-yl)methyl)phenyl)-2-methoxy-benzamide

| 8 | 63 | 10a | 39 |
|---|---|---|---|

¹H NMR (400 MHz, DMSO-d6) δ ppm 11.91 (1 H, s), 10.46 (1 H, s), 9.31 (1 H, br. s.), 7.88 (1 H, d), 7.61-7.76 (4 H, m), 7.47-7.59 (2 H, m), 7.32 (2 H, d), 6.32 (1 H, br. s.), 6.06 (1 H, br. s.), 3.69 (4 H, br. s.), 3.48 (2 H, s), 2.42 (4 H, br. s.), 1.87 (1 H, t), 0.91 (2 H, d), 0.65 (2 H, d)
ESI+ m/z 579 [M + H]+

N-(4-((4-(4-((5-cyclopropyl-1H-pyrazol-3-yl)amino)pyrimidin-2-yl)piperazin-1-yl)methyl)phenyl)-2-(trifluoromethoxy)benzamide

| 9 | 53-39 | 11 | 55 |
|---|---|---|---|

¹H NMR (400 MHz, DMSO-d6) δ ppm 11.91 (1 H, br. s.), 10.46 (1 H, s), 9.31 (1 H, br. s.), 8.23-8.36 (2H, m), 7.97 (1 H, d), 7.88 (1 H, d), 7.70-7.84 (3 H, m), 7.35 (1 H, t), 7.11 (1 H, d), 6.31 (1 H, br. s.), 6.05 (1 H, br. s.), 3.71 (4 H, br. s.), 3.53 (2 H, s), 2.45 (4 H, t), 1.78-1.94 (1 H, m), 0.90 (2 H, d), 0.64 (2 H, d)
ESI+ m/z 563 [M + H]+

N-(4-((4-(4-((5-cyclopropyl-1H-pyrazol-3-yl)amino)pyrimidin-2-yl)piperazin-1-yl)methyl)phenyl)-3-(trifluoromethyl)benzamide

| 10 | 53-40 | 11 | 43 |
|---|---|---|---|

¹H NMR (400 MHz, DMSO-d6) δ ppm 11.92 (1 H, br. s.), 10.45 (1 H, s), 9.31 (1 H, br. s.), 8.15 (2 H, m), 7.93 (2 H, m), 7.88 (1 H, d), 7.75 (2 H, m), 7.34 (2 H, m), 6.30 (1 H, br. s.), 6.06 (1 H, br. s.), 3.70 (4 H, br. s.), 3.50 (2 H, s), 2.42 (3 H, br. s.), 1.87 (1 H, t), 0.91 (2 H, d), 0.65 (2 H, d)
ESI+ m/z 563 [M + H]+

N-(4-((4-(4-((5-cyclopropyl-1H-pyrazol-3-yl)amino)pyrimidin-2-yl)piperazin-1-yl)methyl)phenyl)-4-(trifluoromethyl)benzamide

TABLE 8-continued

| Compound | Examples | Procedure | Yield % |
|---|---|---|---|
| 11 | 63 | 10a | 42 |

<sup>1</sup>H NMR (400 MHz, DMSO-d6) δ ppm 11.91 (1 H, s), 10.38 (1 H, s), 9.31 (1 H, br. s.), 7.87 (1 H, d), 7.71-7.81 (1 H, m), 7.68 (2 H, d), 7.37-7.48 (1 H, m), 7.32 (2 H, d), 7.23 (1 H, t), 6.32 (1 H, br. s.), 6.05 (1 H, br. s.), 3.69 (4 H, br. s.), 3.49 (2 H, s), 2.41 (4 H, t), 1.79-1.92 (1 H, m), 0.91 (2 H, d), 0.65 (2 H, d)
ESI+ m/z 531 [M + H]$^+$ N-(4-((4-(4-((5-cyclopropyl-1H-pyrazol-3-yl)amino)pyrimidin-2-yl)piperazin-1-yl)methyl)phenyl)-2,4-difluoro-Benzamide

| 12 | 63 | 10a | 54 |
|---|---|---|---|

<sup>1</sup>H NMR (400 MHz, DMSO-d6) δ ppm 11.91 (1 H, s), 10.63 (1 H, s), 9.31 (1 H, br. s.), 7.87 (2 H, d), 7.57-7.70 (3 H, m), 7.51 (1 H, d), 7.33 (2 H, d), 6.31 (1 H, br. s.), 6.05 (1 H, br. s.), 3.69 (4 H, br. s.), 3.49 (2 H, s), 2.42 (4 H, br. s.), 1.87 (1 H, t), 0.91 (2 H, d), 0.65 (2 H, d)
ESI+ m/z 581 [M + H]$^+$ N-(4-((4-(4-((5-cyclopropyl-1H-pyrazol-3-yl)amino)pyrimidin-2-yl)piperazin-1-yl)methyl)phenyl)-3-fluoro-2-(trifluoromethyl)benzamide

| 13 | 63 | 10a | 19 |
|---|---|---|---|

<sup>1</sup>H NMR (400 MHz, DMSO-d6) δ ppm 11.91 (1 H, s), 10.77 (1 H, s), 9.30 (1 H, br. s.), 7.88 (1 H, d), 7.69-7.81 (3 H, m), 7.62 (2 H, m), 7.34 (2 H, m), 6.32 (1 H, br. s.), 6.05 (1 H, br. s.), 3.69 (4 H, br. s.), 3.49 (2 H, s), 2.42 (4 H, br. s.), 1.87 (1 H, t), 0.91 (2 H, d), 0.65 (2 H, d)
ESI+ m/z 581 [M + H]$^+$ N-(4-((4-(4-((5-cyclopropyl-1H-pyrazol-3-yl)amino)pyrimidin-2-yl)piperazin-1-yl)methyl)phenyl)-2-fluoro-6-(trifluoromethyl)benzamide

| 14 | 63 | 10a | 60 |
|---|---|---|---|

<sup>1</sup>H NMR (400 MHz, DMSO-d6) δ ppm 11.91 (1 H, s), 10.55 (1 H, s), 9.31 (1 H, br. s.), 7.88 (1 H, d), 7.79 (2 H, d), 7.57-7.74 (3 H, m), 7.32 (2 H, d), 6.31 (1 H, br. s.), 6.05 (1 H, br. s.), 3.69 (4 H, br. s.), 3.49 (2 H, s), 2.42 (4 H, br. s.), 1.77-1.93 (1 H, m), 0.91 (2 H, d), 0.65 (2 H, d)
ESI+ m/z 581 [M + H]$^+$ N-(4-((4-(4-((5-cyclopropyl-1H-pyrazol-3-yl)amino)pyrimidin-2-yl)piperazin-1-yl)methyl)phenyl)-4-fluoro-2-(trifluoromethyl)benzamide

| 15 | 63 | 10a | 33cv |
|---|---|---|---|

<sup>1</sup>H NMR (400 MHz, DMSO-d6) δ ppm 11.91 (1 H, s), 10.00 (1 H, s), 9.31 (1 H, br. s.), 7.87 (1 H, d), 7.69 (2 H, m), 7.62 (1 H, d), 7.30 (2 H, m), 7.03 (1 H, s), 6.90 (1 H, d), 6.32 (1 H, br. s.), 6.05 (1 H, br. s.), 3.93 (3 H, s), 3.69 (4 H, br. s.), 3.48 (2 H, s), 2.35-2.46 (7 H, m), 1.79-1.93 (1 H, m), 0.90 (2 H, d), 0.59-0.70 (2 H, m)
ESI+ m/z 539 [M + H]$^+$ N-(4-((4-(4-((5-cyclopropyl-1H-pyrazol-3-yl)amino)pyrimidin-2-yl)piperazin-1-yl)methyl)phenyl)-2-methoxy-4-methyl benzamide TABLE 8-continued

| Compound | Examples | Procedure | Yield % |
|---|---|---|---|
| 16 | 63 | 10a | 37 |

¹H NMR (400 MHz, DMSO-d6) δ ppm 11.91 (1 H, br. s.), 10.51 (1 H, s), 9.31 (1 H, br. s.), 8.48 (1 H, t), 8.30 (1 H, dt), 8.15 (1 H, dt), 7.81-7.90 (2 H, m), 7.75 (2 H, d), 7.35 (2 H, d), 6.31 (1 H, br. s.), 6.05 (1H, br. s.), 3.70 (4 H, br. s.), 3.50 (2 H, s), 2.43 (4 H, t), 1.79-1.93 (1 H, m), 0.86-0.95 (2 H, m), 0.64 (2H, m)
ESI+ m/z 573 [M + H]+

N-(4-((4-(4-((5-cyclopropyl-1H-pyrazol-3-yl)amino)pyrimidin-2-yl)piperazin-1-yl)methyl)phenyl)-3-(methylsulfonyl)benzamide

| 17 | 53-41 | 11 | 57 |
|---|---|---|---|

¹H NMR (400 MHz, DMSO-d6) δ ppm 11.91 (1 H, s), 9.76 (1 H, s), 9.30 (1 H, br. s.), 7.88 (1 H, d), 7.74 (1 H, t), 7.55-7.63 (1 H, m), 7.45 (1 H, d), 7.31-7.41 (2 H, m), 7.24 (1 H, s), 7.19 (1 H, d), 6.32 (1 H, br. s.), 6.05 (1 H, br. s.), 3.70 (4 H, br. s.), 3.48 (2 H, s), 2.37-2.48 (4 H, m), 2.28 (3 H, s), 1.82-1.93 (1 H, m), 0.91 (2 H, d), 0.60-0.68 (2 H, m)
ESI+ m/z 527 [M + H]+

N-(4-((4-(4-((5-cyclopropyl-1H-pyrazol-3-yl)amino)pyrimidin-2-yl)piperazin-1-yl)methyl)-2-methylphenyl)-2-fluorobenzamide

| 18 | 55-42 | 11 | 67 |
|---|---|---|---|

¹H NMR (400 MHz, DMSO-d6) d ppm 11.87 (1 H, s), 9.76 (1 H, s), 9.17 (1 H, br. s.), 7.72 (1 H, t), 7.54-7.66 (1 H, m), 7.30-7.47 (3 H, m), 7.14-7.30 (2 H, m), 6.22 (1 H, br. s.), 6.03 (1 H, br. s.), 3.71 (4 H, br. s.), 3.50 (2 H, s), 2.67 (2 H, q), 2.43 (4 H, br. s.), 1.79-1.91 (1 H, m), 1.18 (3 H, t), 0.90 (2 H, d), 0.58-0.70 (2 H, m)
ESI+ m/z 555 [M + H]+

N-(4-((4-(4-((5-cyclopropyl-1H-pyrazol-3-yl)amino)-6-methylpyrimidin-2-yl)piperazin-1-yl)methyl)-2-ethylphenyl)-2-fluorobenzamide

| 19 | 55-43 | 11 | 28 |
|---|---|---|---|

¹H NMR (400 MHz, DMSO-d6) d ppm 11.87 (1 H, br. s.), 10.32 (1 H, s), 9.18 (1 H, br. s.), 7.67 (1 H, td), 7.50-7.62 (3 H, m), 7.30-7.39 (2 H, m), 7.24 (1 H, d), 6.21 (1 H, br. s.), 6.03 (1 H, br. s.), 3.68 (4 H, br. s.), 3.46 (2 H, s), 2.73 (2 H, q), 2.42 (4 H, d), 2.12 (3 H, s), 1.81-1.91 (1 H, m), 1.21 (3 H, t), 0.90 (2H, d), 0.59-0.68 (2 H, m)
ESI+ m/z 555 [M + H]+

N-(4-((4-(4-((5-cyclopropyl-1H-pyrazol-3-yl)amino)-6-methylpyrimidin-2-yl)piperazin-1-yl)methyl)-3-ethylphenyl)-2-fluorobenzamide

| 20 | 63 | 10a | 78 |
|---|---|---|---|

¹H NMR (400 MHz, DMSO-d6) δ ppm 11.91 (1 H, br. s.), 10.04 (1 H, s), 9.30 (1 H, br. s.), 8.62 (1 H, s), 7.87 (1 H, d), 7.77 (2 H, m), 7.29 (2 H, m), 6.31 (1 H, br. s.), 6.04 (1 H, br. s.), 3.65-3.73 (4 H, m), 3.47 (2 H, s), 2.41 (4 H, t), 1.82-1.90 (1 H, m), 0.86-0.94 (2 H, m), 0.61-0.67 (2 H, m)
ESI+ m/z 500 [M + H]+

N-(4-((4-(4-((5-cyclopropyl-1H-pyrazol-3-yl)amino)pyrimidin-2-yl)piperazin-1-yl)methyl)phenyl)-2-methyloxazole-4-carboxamide

TABLE 8-continued

| Compound | Examples | Procedure | Yield % |
|---|---|---|---|
| 21 | 63 | 10a | 35 |

¹H NMR (400 MHz, DMSO-d6) δ ppm 11.91 (1 H, br. s.), 10.51 (1 H, s), 9.31 (1 H, br. s.), 7.87 (1 H, d), 7.76 (2 H, m), 7.32 (2 H, m), 6.31 (1 H, br. s.), 6.05 (1 H, br. s.), 3.69 (4 H, br. s.), 3.49 (2 H, s), 2.62 (3 H, s), 2.41 (4 H, t), 1.81-1.91 (1 H, m), 0.85-0.95 (2 H, m), 0.61-0.68 (2H, m)
ESI+ m/z 568 [M + H]+

N-(4-((4-(4-((5-cyclopropyl-1H-pyrazol-3-yl)amino)pyrimidin-2-yl)piperazin-1-yl)methyl)phenyl)-2-methyl-5-(trifluoromethyl)oxazole-4-carboxamide

| 22 | 53-44 | 11 | 16 |
|---|---|---|---|

¹H NMR (400 MHz, DMSO-d6) d ppm 11.91 (1 H, br. s.), 10.79 (1 H, s), 9.31 (1 H, br. s.), 8.88 (1 H, d), 8.21 (1 H, dd), 7.88 (1 H, d), 7.49 (1 H, d), 6.30 (1 H, br. s.), 6.04 (1 H, br. s.), 3.71 (4 H, br. s.), 3.62 (2 H, s), 2.63 (3 H, s), 2.47 (3 H, br. s.), 1.81-1.92 (1 H, m), 0.86-0.94 (2 H, m), 0.61-0.67 (2 H, m)
ESI+ m/z 569 [M + H]+

N-(6-((4-(4-((5-cyclopropyl-1H-pyrazol-3-yl)amino)pyrimidin-2-yl)piperazin-1-yl)methyl)pyridin-3-yl)-2-methyl-5-(trifluoromethyl)oxazole-4-carboxamide

| 23 | 63 | 10a | 26 |
|---|---|---|---|

¹H NMR (400 MHz, DMSO-d6) δ ppm 11.91 (1 H, br. s.), 10.17 (1 H, s), 9.43 (1 H, s), 9.31 (1 H, br. s.), 7.87 (1 H, d), 7.64 (2 H, d), 7.32 (2 H, d), 6.31 (1 H, br. s.), 6.04 (1 H, br. s.), 3.64-3.73 (4 H, m), 3.48 (2 H, s), 2.44 (3 H, s), 2.37-2.43 (4 H, m), 1.81-1.91 (1 H, m), 0.90 (2 H, dd), 0.61-0.68 (2 H, m)
ESI+ m/z 500 [M + H]+

N-(4-((4-(4-((5-cyclopropyl-1H-pyrazol-3-yl)amino)pyrimidin-2-yl)piperazin-1-yl)methyl)phenyl)-3-methylisoxazole-4-carboxamide

| 24 | 53-45 | 11 | 58 |
|---|---|---|---|

¹H NMR (400 MHz, DMSO-d6) δ ppm 11.91 (1 H, br. s.), 10.61 (1 H, s), 9.31 (1 H, br. s.), 8.75 (1 H, d), 8.17 (1 H, d), 8.08 (1 H, t), 7.87 (3 H, d), 7.62-7.75 (1 H, m), 7.33 (2 H, d), 6.31 (1 H, br. s.), 6.05 (1 H, br. s.), 3.70 (4 H, br. s.), 3.50 (2 H, s), 2.43 (4 H, br. s.), 1.87 (1 H, br. s.), 0.90 (2 H, d), 0.65 (2 H, d)
ESI+ m/z 496 [M + H]+

N-(4-((4-(4-((5-cyclopropyl-1H-pyrazol-3-yl)amino)pyrimidin-2-yl)piperazin-1-yl)methyl)phenyl)picolinamide

| 25 | 63 | 10a | 38 |
|---|---|---|---|

¹H NMR (400 MHz, DMSO-d6) δ ppm 11.91 (1 H, br. s.), 10.51 (1 H, s), 9.31 (1 H, br. s.), 8.51-8.56 (1H, m), 7.84-7.91 (1 H, m), 7.76-7.84 (3 H, m), 7.52 (1 H, dd), 7.32 (2 H, d), 6.32 (1 H, br. s.), 6.05 (1H, br. s.), 3.70 (4 H, br. s.), 3.49 (2 H, s), 2.58 (3 H, s), 2.37-2.46 (4 H, m), 1.81-1.91 (1 H, m), 0.85-0.95 (2 H, m), 0.61-0.68 (2 H, m)
ESI+ m/z 510 [M + H]+

N-(4-((4-(4-((5-cyclopropyl-1H-pyrazol-3-yl)amino)pyrimidin-2-yl)piperazin-1-yl)methyl)phenyl)-3-methyl-picolinamide TABLE 8-continued

| Compound | Examples | Procedure | Yield % |
|---|---|---|---|
| 26 | 63 | 10a | 12 |

<sup>1</sup>H NMR (400 MHz, DMSO-d6) δ ppm 11.91 (1 H, br. s.), 10.69 (1 H, s), 8.94 (1 H, d), 8.35-8.42 (1 H, m), 7.88 (1 H, d), 7.81 (1 H, dd), 7.69 (2 H, m), 7.34 (2 H, m), 6.31 (1 H, br. s.), 6.04 (1 H, br. s.), 3.70 (4H, br. s.), 3.49 (2 H, s), 2.43 (4 H, br. s.), 1.81-1.92 (1 H, m), 0.85-0.95 (2 H, m), 0.61-0.69 (2 H, m)
ESI+ m/z 564 [M + H]<sup>+</sup>

N-(4-((4-(4-((5-cyclopropyl-1H-pyrazol-3-yl)amino)pyrimidin-2-yl)piperazin-1-yl)methyl)phenyl)-3-(trifluoromethyl)-picolinamide

| 27 | 63 | 10a | 12 |
|---|---|---|---|

$^1$H NMR (400 MHz, DMSO-d6) δ ppm 11.91 (1 H, br. s.), 10.66 (1 H, s), 9.31 (1 H, br. s.), 8.87 (1 H, d), 8.22 (1 H, d), 7.83-7.90 (2 H, m), 7.64 (2 H, m), 7.34 (2 H, m), 6.32 (1 H, br. s.), 6.05 (1 H, br. s.), 3.69 (4 H, br. s.), 3.49 (2 H, s), 2.42 (4 H, br. s.), 1.82-1.91 (1 H, m), 0.91 (2 H, d), 0.62-0.69 (2 H, m)
ESI+ m/z 564 [M + H]<sup>+</sup>

N-(4-((4-(4-((5-cyclopropyl-1H-pyrazol-3-yl)amino)pyrimidin-2-yl)piperazin-1-yl)methyl)phenyl)-2-(trifluoromethyl)-nicotinamide

| 28 | 63 | 10a | 63 |
|---|---|---|---|

$^1$H NMR (400 MHz, DMSO-d6) δ ppm 11.91 (1 H, br. s.), 10.18 (1 H, s), 9.31 (1 H, br. s.), 8.34 (1 H, dd), 8.06 (1 H, dd), 7.88 (1 H, d), 7.69 (2 H, m), 7.32 (2 H, m), 7.16 (1 H, dd), 6.31 (1 H, br. s.), 6.05 (1H, br. s.), 4.00 (3 H, s), 3.69 (4 H, br. s.), 3.49 (2 H, s), 2.41 (4 H, br. s.), 1.81-1.92 (1 H, m), 0.91 (2 H, d), 0.60-0.69 (2 H, m)
ESI+ m/z 525 [M + H]<sup>+</sup>

N-(4-((4-(4-((5-cyclopropyl-1H-pyrazol-3-yl)amino)pyrimidin-2-yl)piperazin-1-yl)methyl)phenyl)-2-methoxy-nicotinamide

| 29 | 63 | 10a | 51 |
|---|---|---|---|

$^1$H NMR (400 MHz, DMSO-d6) δ ppm 11.91 (1 H, br. s.), 10.74 (1 H, s), 9.31 (1 H, br. s.), 8.96-9.03 (2H, m), 7.88 (1 H, d), 7.91 (1 H, d), 7.65 (2 H, m), 7.34 (2 H, m), 6.31 (1 H, br. s.), 6.05 (1 H, br. s.), 3.70 (4 H, br. s.), 3.50 (2 H, s), 2.42 (4 H, br. s.), 1.82-1.91 (1 H, m), 0.86-0.96 (2 H, m), 0.60-0.69 (2 H, m)
ESI+ m/z 564 [M + H]<sup>+</sup>

N-(4-((4-(4-((5-cyclopropyl-1H-pyrazol-3-yl)amino)pyrimidin-2-yl)piperazin-1-yl)methyl)phenyl)-4-(trifluoromethyl)-nicotinamide

| 30 | 53-46 | 11 | 53 |
|---|---|---|---|

$^1$H NMR (400 MHz, DMSO-d6) δ ppm 11.94 (1 H, br. s.), 10.66 (1 H, br. s.), 9.35 (1 H, br. s.), 8.87 (1 H, d), 8.21 (1 H, d), 7.82-7.90 (2 H, m), 7.63 (2 H, d), 7.34 (2 H, d), 6.27 (1 H, br. s.), 6.06 (1 H, br. s.), 4.05-4.30 (2 H, m), 3.98 (1 H, d), 3.06-3.26 (2 H, m), 2.90-3.06 (1 H, m), 2.68 (1 H, br. s.), 2.43 (1 H, br. s.), 2.09 (1 H, br. s.), 1.81-1.93 (1 H, m), 1.16 (3 H, d), 0.87-0.97 (2 H, m), 0.58-0.69 (2 H, m)
ESI+ m/z 578 [M + H]<sup>+</sup>

(R)-N-(4-((4-(4-((5-cyclopropyl-1H-pyrazol-3-yl)amino)pyrimidin-2-yl)-2-methylpiperazin-1-yl)methyl)phenyl)-2-(trifluoromethyl)nicotinamide TABLE 8-continued

| Compound | Examples | Procedure | Yield % |
|---|---|---|---|
| 31 | 53-47 | 11 | 46 |

(S)-N-(4-((4-(4-((5-cyclopropyl-1H-pyrazol-3-yl)amino)pyrimidin-2-yl)-2-methylpiperazin-1-yl)methyl)phenyl)-2-(trifluoromethyl)nicotinamide ¹H NMR (400 MHz, DMSO-d6) δ ppm 11.93 (1 H, br. s.), 10.65 (1 H, s), 9.33 (1 H, br. s.), 8.87 (1 H, d), 8.21 (1 H, d), 7.82-7.90 (2 H, m), 7.63 (2 H, m), 7.34 (2 H, m), 6.27 (1 H, br. s.), 6.06 (1 H, br. s.), 4.07-4.26 (2 H, m), 3.98 (1 H, d), 3.09-3.23 (2 H, m), 2.98 (1 H, dd), 2.67 (1 H, d), 2.44 (1 H, d), 2.09 (1 H, t), 1.82-1.93 (1 H, m), 1.15 (3 H, d), 0.87-0.97 (2 H, m), 0.61-0.68 (2 H, m)
ESI+ m/z 578 [M + H]+

| 32 | 63 | 10a | 23 |

N-(4-((4-(4-((5-cyclopropyl-1H-pyrazol-3-yl)amino)pyrimidin-2-yl)piperazin-1-yl)methyl)phenyl)-3-(trifluoromethyl)-isonicotinamide ¹H NMR (400 MHz, DMSO-d6) δ ppm 11.91 (1 H, br. s.), 10.72 (1 H, s), 9.31 (1 H, br. s.), 9.10 (1 H, s), 9.03 (1 H, d), 7.88 (1 H, d), 7.79 (1 H, d), 7.63 (2 H, m), 7.34 (2 H, m), 6.31 (1 H, br. s.), 6.03 (1 H, br. s.), 3.69 (4 H, br. s.), 3.49 (2 H, s), 2.42 (4 H, br. s.), 1.81-1.92 (1 H, m), 0.84-0.96 (2 H, m), 0.57-0.72 (2 H, m)
ESI+ m/z 564 [M + H]+

| 33 | 63 | 10a | 21 |

N-(4-((4-(4-((5-cyclopropyl-1H-pyrazol-3-yl)amino)pyrimidin-2-yl)piperazin-1-yl)methyl)phenyl)-1-methyl-3-(trifluoromethyl)-1H-pyrazole- ¹H NMR (400 MHz, DMSO-d6) δ ppm 11.84-12.02 (1 H, m), 10.01-10.18 (1 H, m), 9.19-9.38 (1 H, m), 8.43-8.61 (1 H, m), 7.81-7.97 (1 H, m), 7.55-7.74 (2 H, m), 7.25-7.38 (2 H, m), 6.21-6.41 (1H, m), 5.95-6.19 (1 H, m), 3.99 (3 H, s), 3.60-3.75 (4 H, m), 3.42-3.51 (2 H, m), 2.36-2.46 (4 H, m), 1.77-1.94 (2 H, m), 0.82-0.98 (2 H, m), 0.58-0.70 (2 H, m)
ESI+ m/z 567 [M + H]+

| 34 | 63 | 10a | 16 |

N-(4-((4-(4-((5-cyclopropyl-1H-pyrazol-3-yl)amino)pyrimidin-2-yl)piperazin-1-yl)methyl)phenyl)-1-methyl-1H-imidazole-2-carboxamide ¹H NMR (400 MHz, DMSO-d6) δ ppm 11.91 (1 H, br. s.), 10.27 (1 H, s), 9.31 (1 H, br. s.), 7.87 (1 H, d), 7.78 (2 H, d), 7.44 (1 H, s), 7.29 (2 H, d), 7.08 (1 H, d), 6.31 (1 H, br. s.), 6.04 (1 H, br. s.), 4.00 (3 H, s), 3.61-3.76 (4 H, m), 3.48 (2 H, s), 2.41 (4 H, t), 1.80-1.92 (1 H, m), 0.84-0.96 (2 H, m), 0.60-0.70 (2 H, m)
ESI+ m/z 499 [M + H]+

| 35 | 63 | 10a | 21 |

N-(4-((4-(4-((5-cyclopropyl-1H-pyrazol-3-yl)amino)pyrimidin-2-yl)piperazin-1-yl)methyl)phenyl)pyrazine-2-carboxamide ¹H NMR (400 MHz, DMSO-d36 37 6) δ ppm 11.91 (1 H, br. s.), 10.71 (1 H, s), 9.31 (2 H, d), 8.94 (1 H, d), 8.79-8.85 (1 H, m), 7.87 (3 H, d), 7.34 (2 H, d), 6.31 (1 H, br. s.), 6.05 (1 H, br. s.), 3.70 (4 H, br. s.), 3.50 (2 H, s), 2.42 (4 H, t), 1.81-1.93 (1 H, m), 0.90 (2 H, d), 0.60-0.68 (2 H, m)
ESI+ m/z 497 [M + H]+

TABLE 8-continued

| Compound | Examples | Procedure | Yield % |
|---|---|---|---|
| 36 | 63 | 10a | 14 |

¹H NMR (400 MHz, DMSO-d₆) d ppm 11.91 (1 H, br. s.), 10.85 (1 H, s), 9.31 (1 H, br. s.), 9.11 (1 H, s), 9.05 (1 H, s), 7.88 (1 H, d), 7.67 (2 H, d), 7.37 (2 H, d), 6.33 (1 H, br. s.), 6.05 (1 H, br. s.), 3.70 (4 H, br. s.), 3.50 (2 H, s), 2.43 (4 H, br. s.), 1.87 (1 H, br. s.), 0.91 (2 H, d), 0.65 (2 H, d) ESI+ m/z 565 [M + H]⁺

N-(4-((4-(4-((5-cyclopropyl-1H-pyrazol-3-yl)amino)pyrimidin-2-yl)piperazin-1-yl)methyl)phenyl)-3-(trifluoromethyl)-pyrazine-2-carboxamide

| 37 | 61 | 10d | 37 |
|---|---|---|---|

¹H NMR (400 MHz, DMSO-d6) δ ppm 11.92 (1 H, br. s.), 10.39 (1 H, s), 9.31 (1 H, br. s.), 7.90 (2 H, d), 7.94 (2 H, d), 7.52 (2 H, d), 7.37 (2 H, d), 6.31 (1 H, br. s.), 6.05 (1 H, br. s.), 3.71 (4 H, br. s.), 3.61 (2H, s), 2.38-2.48 (4 H, m), 1.80-1.92 (1 H, m), 0.81-0.97 (2 H, m), 0.59-0.68 (2 H, m) ESI+ m/z 579 [M + H]⁺

4-((4-(4-((5-cyclopropyl-1H-pyrazol-3-yl)amino)pyrimidin-2-yl)piperazin-1-yl)methyl)-N-(4-(trifluoromethoxy)phenyl)benzamide

| 38 | 61 | 10d | 10 |
|---|---|---|---|

¹H NMR (400 MHz, DMSO-d6) δ 11.92 (1 H, br. s.), 10.51 (1 H, s), 9.32 (1 H, br. s.), 8.27 (1 H, s), 8.06 (1 H, d), 7.97 (2 H, d), 7.88 (1 H, d), 7.61 (1 H, t), 7.53 (2 H, d), 7.46 (1 H, d), 6.32 (1 H, br. s.), 6.05 (1 H, br. s.), 3.72 (4 H, br. s.), 3.62 (2 H, s), 2.39-2.48 (4 H, m), 1.76-1.91 (1 H, m), 0.81-0.96 (2 H, m), 0.58-0.67 (2 H, m) ESI+ m/z 563 [M + H]⁺

4-((4-(4-((5-cyclopropyl-1H-pyrazol-3-yl)amino)pyrimidin-2-yl)piperazin-1-yl)methyl)-N-(3-(trifluoromethyl)-phenyl)benzamide

| 39 | 61 | 10d | 7 |
|---|---|---|---|

¹H NMR (400 MHz, Acetone) δ ppm 9.85 (s, 1 H) 8.35-8.51 (m, 1 H) 8.11 (d, J = 8.31 Hz, 2 H) 7.91-8.05 (m, 3 H) 7.72 (d, J = 8.31 Hz, 2 H) 7.59 (d, J = 7.83 Hz, 2 H) 6.48 (br. s., 1 H) 5.99-6.17 (m, 1 H) 5.63 (s, 1 H) 3.82-3.95 (m, 1 H) 3.64-3.74 (m, 2 H) 2.85 (br. s., 3H H) 1.88-1.99 (m, 1 H) 0.88-1.00 (m, 2 H) 0.67-0.77 (m, 2 H) ESI+ m/z 563 [M + H]⁺

4-((4-(4-((5-cyclopropyl-1H-pyrazol-3-yl)amino)pyrimidin-2-yl)piperazin-1-yl)methyl)-N-(4-(trifluoromethyl)phenyl)-benzamide

| 40 | 53-48 | 11 | 59 |
|---|---|---|---|

¹H NMR (400 MHz, DMSO-d6) δ ppm 11.91 (1 H, s), 10.54 (1 H, s), 9.29 (1 H, br. s.), 7.77-7.90 (2 H, m), 7.68 (1 H, d), 7.30-7.45 (2 H, m), 7.19 (2 H, m), 7.07 (2 H, m), 6.31 (1 H, br. s.), 6.03 (1 H, br. s.), 3.64 (4 H, br. s.), 3.38 (2 H, s), 2.33 (4 H, t), 1.80-1.93 (1 H, m), 0.90 (2 H, d), 0.63 (2 H, s) ESI+ m/z 549 [M + H]⁺

N-(4-((4-(4-((5-cyclopropyl-1H-pyrazol-3-yl)amino)pyrimidin-2-yl)piperazin-1-yl)methyl)phenyl)-2-fluorobenzene-sulfonamide TABLE 8-continued

| Compound | Examples | Procedure | Yield % |
|---|---|---|---|
| 41 | 53-49 | 11 | 22 |

N-(5-((4-(4-((5-cyclopropyl-1H-pyrazol-3-yl)amino)pyrimidin-2-yl)piperazin-1-yl)methyl)pyrazin-2-yl)-2-(trifluoromethyl)benzamide $^1$H NMR (400 MHz, DMSO-d6) δ ppm 11.90 (1 H, br. s.), 11.42 (1 H, s), 9.33 (2 H, br. s.), 8.51 (1 H, s), 7.82-7.92 (2 H, m), 7.68-7.82 (3 H, m), 6.31 (1 H, br. s.), 6.04 (1 H, br. s.), 3.77 (1 H, br. s.), 3.71 (5H, br. s.), 2.55 (1 H, s), 1.92 (2 H, s), 1.80-1.90 (1 H, m), 0.87-0.95 (2 H, m), 0.63-0.69 (2 H, m)
ESI+ m/z 565 [M + H]$^+$

| 42 | 53-50 | 11 | 27 |
|---|---|---|---|

N-(6-((4-(4-((5-cyclopropyl-1H-pyrazol-3-yl)amino)pyrimidin-2-yl)piperazin-1-yl)methyl)pyridazin-3-yl)-2-(trifluoromethyl)benzamide $^1$H NMR (400 MHz, DMSO-d6) δ ppm 11.92 (1 H, br. s.), 11.74 (1 H, br. s.), 9.32 (1 H, br. s.), 8.40 (1 H, d), 7.69-7.99 (6 H, m), 6.33 (1 H, br. s.), 6.06 (1 H, br. s.), 3.82 (2 H, br. s.), 3.71 (3 H, br. s.), 1.87 (1H, br. s.), 0.91 (3 H, br. s.), 0.65 (2 H, br. s.)
ESI+ m/z 565 [M + H]$^+$

| 43 | 53-51 | 11 | 10 |
|---|---|---|---|

N-(6-((4-(4-((5-cyclopropyl-1H-pyrazol-3-yl)amino)pyrimidin-2-yl)piperazin-1-yl)methyl)pyridin-3-yl)-2-(trifluoromethyl)benzamide $^1$H NMR (400 MHz, DMSO-d6) δ ppm 11.94 (1 H, br. s.), 11.11 (1 H, br. s.), 9.41 (1 H, br. s.), 8.17 (1H, br. s.), 7.64-7.93 (5 H, m), 6.35 (1 H, br. s.), 6.05 (1 H, br. s.), 3.77 (1 H, br. s.), 3.70 (1 H, br. s.), 3.55 (2 H, br. s.), 2.55 (2 H, s), 1.92 (1 H, s), 1.82-1.91 (1 H, m), 1.23-1.31 (1 H, m), 0.87-0.98 (2 H, m), 0.67 (2 H, quin)
ESI+ m/z 564 [M + H]$^+$

| 44 | 57-37 | 11 | 40 |
|---|---|---|---|

N-(4-((4-(4-((5-cyclopropyl-1,3,4-oxadiazol-2-yl)amino)pyrimidin-2-yl)piperazin-1-yl)methyl)phenyl)-2-(trifluoromethyl)benzamide $^1$H NMR (400 MHz, DMSO-d6) δ ppm 10.96 (s, 1H), 10.53 (s, 1H), 8.19 (d, J = 5.4 Hz, 1H), 7.88-7.77 (m, 2H), 7.75-7.63 (m, 4H), 7.31 (d, J = 8.3 Hz, 2H), 6.86 (d, J = 5.9 Hz, 1H), 3.73 (br. s., 4H), 3.49 (s, 2H), 2.42 (t, J = 4.6 Hz, 4H), 2.14 (tt, J = 5.0, 8.5 Hz, 1H), 1.11-1.05 (m, 2H), 0.97-0.91 (m, 2H)
ESI+ m/z 555 [M + H]$^+$ TABLE 8-continued

| Compound | Examples | Procedure | Yield % |
|---|---|---|---|
| 45 | 56-37 | 11 | 38 |

¹H NMR (400 MHz, DMSO-d₆) δ ppm 10.39 (1 H, s), 9.72 (1 H, s), 8.07 (1 H, d), 8.02 (1 H, d), 7.63-7.73 (3 H, m), 7.62 (2 H, s), 7.28-7.40 (4 H, m), 6.65 (1 H, d), 6.53-6.61 (1 H, m), 3.81 (3 H, s), 3.74 (4 H, br. s.), 3.49 (2 H, s), 2.44 (4 H, br. s.)
ESI+ m/z 564 [M + H]+

N-(4-((4-(4-((4-methoxypyridin-2-yl)amino)pyrimidin-2-yl)piperazin-1-yl)methyl)phenyl)-2-(trifluoromethyl)benzamide

| 46 | 55-37 | 11 | 49 |
|---|---|---|---|

¹H NMR (400 MHz, DMSO-d₆) δ ppm 11.87 (1 H, br. s.), 10.53 (1 H, s), 9.18 (1 H, br. s.), 7.77-7.88 (2H, m), 7.62-7.74 (4 H, m), 7.32 (2 H, d), 5.93-6.36 (2 H, m), 3.69 (4 H, br. s.), 3.48 (2 H, br. s.), 2.41 (4 H, br. s.), 2.08-2.16 (3 H, m), 1.79-1.92 (1 H, m), 0.90 (2 H, d), 0.60-0.68 (2 H, m)
ESI+ m/z 577 [M + H]+

N-(4-((4-(4-((5-cyclopropyl-1H-pyrazol-3-yl)amino)-6-methylpyrimidin-2-yl)piperazin-1-yl)methyl)phenyl)-2-(trifluoromethyl)benzamide

| 47 | 54-37 | 11 | 41 |
|---|---|---|---|

¹H NMR (400 MHz, DMSO-d₆) δ ppm 11.86 (1 H, s), 10.53 (1 H, s), 9.31 (1 H, br. s.), 7.76-7.90 (3 H, m), 7.63-7.75 (4 H, m), 7.32 (2 H, d), 6.04-6.44 (2 H, m), 3.69 (4 H, br. s.), 3.48 (2 H, s), 2.41 (4 H, br. s.), 2.19 (3 H, s)
ESI+ m/z 537 [M + H]+

N-(4-((4-(4-((3-methyl-1H-pyrazol-5-yl)amino)pyrimidin-2-yl)piperazin-1-yl)methyl)phenyl)-2-(trifluoromethyl)benzamide

| 48 | 63 | 10c | 22 |
|---|---|---|---|

¹H NMR (400 MHz, DMSO-d₆) δ ppm 11.91 (1 H, br. s.), 9.31 (1 H, br. s.), 7.98 (1 H, s), 7.87 (1 H, d), 7.46 (2 H, d), 7.17 (2 H, d), 6.30 (1 H, br. s.), 6.04 (1 H, br. s.), 4.05 (1 H, td), 3.68 (4 H, br. s.), 3.39-3.55 (3 H, m), 3.32-3.39 (1 H, m), 2.39 (4 H, t), 1.79-2.05 (4 H, m), 1.47-1.63 (1 H, m), 1.13 (3 H, d), 0.79-0.98 (2 H, m), 0.54-0.76 (2 H, m)
ESI+ m/z 502 [M + H]+

N-(4-((4-(4-((5-cyclopropyl-1H-pyrazol-3-yl)amino)pyrimidin-2-yl)piperazin-1-yl)methyl)phenyl)-2-methylpyrrolidine-1-carboxamide

TABLE 8-continued

| Compound | Examples | Procedure | Yield % |
|---|---|---|---|
| 49 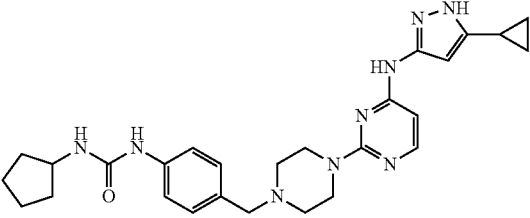 [SMILES: O=C(Nc1ccc(CN2CCN(c3nccc(Nc4cc(C5CC5)[nH]n4)n3)CC2)cc1)NC1CCCC1] 1-cyclopentyl-3-(4-((4-(4-((3-cyclopropyl-1H-pyrazol-5-yl)amino)pyrimidin-2-yl)piperazin-1-yl)methyl)phenyl)urea | 53-52 <br> $^1$H NMR (400 MHz, DMSO-d$_6$) δ ppm 11.91 (1 H, br. s.), 9.30 (1 H, br. s.), 8.21 (1 H, s), 7.87 (1 H, d), 7.33 (2 H, d), 7.16 (2 H, d), 6.31 (1 H, br. s.), 6.11 (1 H, d), 5.95-6.08 (1 H, m), 3.93 (1 H, sxt), 3.67 (4H, br. s.), 3.41 (2 H, br. s.), 2.38 (4 H, br. s.), 1.77-1.91 (3 H, m), 1.48-1.71 (4 H, m), 1.29-1.42 (2 H, m), 0.90 (2 H, d), 0.59-0.68 (2 H, m) <br> ESI+ m/z 502 [M + H]$^+$ | 11 | 47c |

Pharmacological Evaluation of the Compounds of the Invention

Compounds of Formula (I), according to the invention, have been studied in vitro in order to establish their potential FYN kinase inhibitory activity and their efficacy in a cellular model for testing kinase inhibition, as well as to establish the efficacy of the best compounds, resulting from the screening in vitro, in experiments of induced hyperalgesia and pain behaviour in a model of osteoarthritis in rats.

PP2, 4-amino-5-(4-chlorophenyl)-7-(dimethylethyl)pyrazolo[3,4-d]pyrimidine, a pharmacological tool able to selectively inhibit the members of SRC-family kinases (Hanke et al., J. of Biological Chemistry 271 (2):695-701) was used as comparative drugs.

The obtained results are summarized in the following Tables 9-12.

Example 68

In Vitro Kinase Assay.

Assays to determine the kinase inhibitory activity of compounds were performed using an automatic liquid handling device (Microlab STAR Hamilton) and Z'-LYTE™ Kinase Assay Platform, a Fluorescence Resonance Energy Transfer (FRET)-based assay platform compatible with high-throughput screening (HTS) applications. The assay employs a fluorescence-based, coupled-enzyme format and utilizes the differential sensitivity of phosphorylated and non-phosphorylated peptides to proteolytic cleavage.

Test compounds were evaluated in a screening test towards active FYN (human recombinant, 62.7 kDa). The desired enzyme was incubated in a 384 low-volume microplate with a synthetic peptide-substrate, ATP and different inhibitor concentrations, ranging from $10^{-10}$ M up to $10^{-5}$ M final concentration. Samples representing the 0% inhibition (or total enzymatic activity) were in the presence of compound diluent (1% DMSO final) in Reaction Buffer (50 mM Hepes, 10 mM MgCl2, 1 mM EGTA, 0.01% Brij-35, pH 7.5).

A near-Km ATP concentrations for the kinase and an optimal enzyme concentration that phosphorylates 20-40% of the Z'-LYTE™ Tyr 2 Peptide in a one-hour incubation, were selected. All reagents were diluted in reaction buffer and the kinase reaction was carried out in a total volume of 10 µl, for 60 minutes at 25° C. The 0% Phosphorylation (i.e. no ATP) and 100% Phosphorylation (i.e. synthetically phosphorylated peptide supplied) Assay Controls, included in each plate, allowed to calculate the percent phosphorylation achieved in the specific reaction well. The 0% Inhibition and 0% Phosphorylation (i.e. 100% Inhibition) Controls define the dynamic range in the screen. At the end of incubation, a secondary reaction (the Development Reaction) started by adding 5 µl of Development Reagent, containing a site-specific protease that recognizes and cleaves non-phosphorylated peptides, and was interrupted after 60 minutes with 5 µl/sample of Stop Reagent. Measurement of the Coumarin (Ex. 400 nm, Em. 460 nm) and Fluorescein (Ex. 400 nm, Em. 535 nm) emission signals were performed by a fluorescence plate reader (Envision, PerkinElmer).

The compounds were tested in a range of concentrations $10^{-6}$-$10^{-9}$ M.

Results are expressed as percentage of inhibition and the IC50 values were calculated by non-linear curve fitting using GraphPad™ Prism software.

The FYN kinase inhibitory activity of representative examples of compounds of Formula (I) is reported in the following table.

TABLE 9

FYN KINASE INHIBITION

| Compound | IC50(nM) FYN INHIBITION |
|---|---|
| 1 | 96 |
| 2 | 9 |
| 3 | 70 |
| 4 | 17 |
| 5 | 23 |
| 6 | 89 |
| 7 | 150 |
| 8 | 39 |
| 9 | >1000 |
| 10 | 950 |
| 11 | 16 |
| 12 | 29 |
| 13 | 23 |
| 14 | 16 |
| 15 | 220 |
| 16 | 122 |
| 17 | 30 |
| 18 | 94 |
| 19 | 1020 |
| 20 | 86 |
| 21 | 42 |
| 22 | 424 |
| 23 | 103 |
| 24 | 1100 |
| 25 | 105 |
| 26 | 9 |
| 27 | 27 |
| 28 | 237 |

TABLE 9-continued

FYN KINASE INHIBITION

| Compound | IC50(nM) FYN INHIBITION |
|---|---|
| 29 | 8 |
| 30 | 180 |
| 31 | 667 |
| 32 | 17 |
| 33 | 74 |
| 34 | 1450 |
| 35 | 282 |
| 36 | 8 |
| 37 | >1000 |
| 38 | >1000 |
| 39 | >1000 |
| 40 | 280 |
| 41 | 4 |
| 42 | 663 |
| 43 | 27 |
| 44 | >1000 |
| 45 | 441 |
| 46 | 29 |
| 47 | 41 |
| 48 | 37 |
| 49 | 69 |
| PP2 | 46 |

As Table 9 shows, the more potent Fyn kinase inhibitors of Formula (I) resulted to be compound 2, 11, 14, 26, 29, 36 and 41. Advantageous compounds hence are those wherein A is the phenyl or the pyridyl or the pyrazinyl group, preferably ortho-substituted to the amidic group B with the —$CF_3$ substituent.

Furthermore, the preferred compound resulted have G being 1-H-pyrazol-3-yl, substituted, more preferably in the 5-position with the cyclopropyl group, as exhibited by the same compounds above indicated.

As it is evident from Table 9, PP2 was less effective.

Example 69

Cellular Model for Testing Kinase Inhibition: Gene Reporter (GR) Assay

To determine if the compounds of the invention were active also in a cellular model, a gene reporter assay was established in a cell line (JB6 CI 41-5a (P+)) know to activate Fyn kinase via an inflammatory stimuli (TNFα). GR assay measures the activation of the nuclear transcription factor NF-kB, situated down-stream the Fyn activation pathway. Products active in this analysis has to penetrate in the cell and inhibit the activation pathway of NF-kB.

Gene Reporter Assay

The murine epithelial cell line JB6 CI 41-5a (P+) (ATCC® Cat. # CRL-2010) was stably transfected with the pGL4.32[luc2P/NFkB-RE/Hygro] vector (Promega). Clonal selection was achieved by limiting dilution in MEM (+Earle's BSS+1.5 g/l sodium bicarbonate+0.1 mM NEAA)+GlutaMAX™-I, +1 mM sodium pyruvate, +5% FBS+80 µg/ml Hygromycin B. The clones were tested for their response to TNFα stimulus. The obtained transfected cells (JB6(P+) NFkB-RE-luc2P T3-$C_{10}$) contained a firefly luciferase gene (luc2P) under the control of minimal TATA promoter with multiple Nuclear Factor-kB response elements (NFkB-REs). These NFkB-REs are DNA binding sequences for the NF-kB transcription factor.

JB6(P+) NFkB-RE-luc2P T3-C10 cells were used for the analysis of NF-kB activity modulation, after TNFα stimulation, by Fyn-inhibitors (Hwang et al.; Biochem. Pharmacol. 2009, 77 (7):1213-22).

6000 cells/well were plated in a 96× well plate. After 24 h new medium without antibiotics was given. After further 24 h the cells were pre-treated with the different compounds for 1 h and then stimulated with 2 ng/ml TNFα for 4 h. In each experiments two positive standards were always used, and each tested condition was analyzed in quadruplicate.

The luciferase analysis was performed with ONE-Glo™+ToxLuciferase Reporter and Cell Viability Assay kit (Promega). This assay combined luciferase assay chemistry with a cell viability marker to better understand reporter gene expression in the context of cell health. The assay uses a two-step process. The first part of the assay was a non-lytic fluorescence assay (CellTiter-Fluor™ Cell Viability Assay) that measured the relative number of live cells in a culture population, as it measures a conserved and constitutive protease activity within live cells. The live-cell protease activity was restricted to intact viable cells and was measured using a fluorogenic, cell-permeant peptide substrate (glycyl-phenylalanyl-aminofluorocoumarin; GF-AFC). The generated fluorescent signal, proportional to the number of living cells, was measured with EnVision microplate reader (PerkinElmer) using an excitation wavelength of 400 nm and emission wavelength of 500 nm.

The second part of the assay uses the ONE-Glo™ Luciferase Assay System to quantify firefly luciferase reporter gene expression. The ONE-Glo™ Assay contained a fluoro-luciferin substrate, more tolerant to sample components than standard luciferase assay reagents. Luminescence was measured with EnVision microplate reader (PerkinElmer).

Compounds of Formula (I) were tested for their capacity to penetrate into the cell and inhibit the activation pathway of NF-kB.

The results obtained are summarized in the following Table 10.

TABLE 10

| Gene reporter (GR) inhibition | |
|---|---|
| Compound | $IC_{50}$(nM) GR Inhibition |
| 2 | 190 |
| 4 | 788 |
| 8 | 766 |
| 12 | 430 |
| 13 | 493 |
| 14 | 603 |
| 17 | >2000 |
| 18 | 1366 |
| 21 | 854 |
| 23 | 1933 |
| 26 | 247 |
| 27 | 1343 |
| 29 | 973 |
| 32 | 1000 |
| 36 | >2000 |
| 41 | >2000 |
| 43 | 1053 |
| PP2 | 505 |

As Table 10 shows, some compounds of the invention, particularly the compounds of the Examples 2 and 26 demonstrated to be able to penetrate into the cell and inhibit at sub-µmolar concentration the FYN kinase activation, via TNF-α stimulation. Also the standard comparator PP2 demonstrated to be able to entry into the cell and to be effective in this model.

Example 70

Toxicity in JB6 Cells

Cell toxicity analysis in JB6 CI 41-5a (P+) is important to determine if the results obtained in GR assay are due to the pharmacological effect or to a toxicity effect of the products.

The study was performed with the following method:

The murine epithelial cell line JB6 CI 41-5a (P+) (ATCC® Cat. # CRL-2010) was used to analyze the products cell toxicity by MTT method. $10^4$ cells/well were plated in a 96× well plate MEM 5%. 48 h after plating the cells were pre-treated with the different compounds and positive standards for 1 h and then stimulated with TNFα (to simulate the same experimental conditions used in the gene reporter assay) for 4 and 24 h. At the end of the incubation time, the medium was removed and was substituted with a mixture 10:1 of MEM 5% MTT (2 mg/ml) for 1 h at 37° C. in the cell incubator. MTT is a tetrazolium salt especially useful for assaying the quantification of living metabolically active cells; it works by being metabolized by mitochondrial dehydrogenases to form a formazan dye (salt). After this incubation the supernatant was removed and the precipitated salt was dissolved with 100 μl of DMSO. The plate was then read at 540 nm. 100 μl of DMSO alone (without cells) were used as a blank, that was subtracted from the measure of each sample.

The compounds of the invention demonstrated a scarce cellular toxicity in JB6 cell line after 24 hours of incubation. The compounds 2, 21 and 26, as representative compounds of Formula (I) of the invention exhibited a percent residual cell vitality at 3 μmolar higher than 50%, whereas the putative standard reference PP2 was much more toxic, exhibiting at the same concentration only a 18% of residual cell vitality.

Example 71

Kinase Selectivity

Compound 2, as a representative compound of the invention, was examined for kinase selectivity.

Its potential kinase inhibition activity was studied in a standard panel of about 100 human kinase assay by Cerep. As already shown in Table 2, it exhibits a $10^{-9}$ M FYN kinase inhibition. Among the other kinases examined of the SRC family, Compound 2 inhibited all of them with an $IC_{50}$ higher than $10^{-7}$ M concentration and with an average potency ratio of about 100. Compound 2 was practically ineffective for more than 70% of the remaining kinases examined, a part RET, CDK2, FLT-3 and FLT-4, that were inhibited higher than 50% at $10^{-7}$ M concentration. On the contrary, PP2 was much less selective for the kinases of SRC family. In fact, their $IC_{50}$ inhibition ($10^{-9}$ M) for these kinases were as follows:
a) Compound 2: FYN (9), SRC (730), LYN (1400), YES (270), BLK (480), LCK (450) and HCK (3200);
b) PP2: FYN (44), SRC (70), LYN (64), YES (61), BLK (132), LCK (67) and HCK (61);

Example 72

Description of Pharmacological Activity in "vivo" of the Compounds of the Invention Compounds of formula (I) have been proved to be potent analgesics in several models of inflammatory, chronic and neuropathic pain.

Accordingly, the compounds of the invention are useful for the treatment of both acute and chronic pain, including but not limited to: postoperative pain, muscular pain, pain resulting from various forms of trauma, as well as chronic pain, neuropathic pain, cancer pain, pain caused by arthritis.

The efficacy of the compounds of Formula (I) for the treatment of inflammatory and neuropathic pain has been determined using the following in vivo animal models.

CFA-induced Inflammatory Pain in Rats.

Male Wistar rats were injected into the right hind footpad with 300 μg of *Mycobacterium tuberculosis* in 100 μL of liquid paraffin (Complete Freund's Adjuvant; CFA). Seventy-two hours later, compounds 2 and 26 were administered subcutaneously and 24 h after the administration, the response to noxious mechanical stimulation was assessed by measuring paw withdrawal threshold (PWT) with an analgesimeter of the Randall-Selitto type. Animals were gently restrained, and steadily increasing pressure was applied to the dorsal surface of both the ipsi-lateral (CFA-treated) and the contra-lateral paw via a dome-shaped plastic tip.

100% protection means that the animal treated with the compound and CFA can tolerate the same stimulus (weight) as the control animal which has not received CFA treatment.

Table 11 shows the results obtained in this CFA model, for two representative compounds of Formula (I) in comparison to PP2.

TABLE 11

| | % protective effect vs. CFA induced hyperalgesia | |
|---|---|---|
| Compound | 3 μmolar concentration | 10 μmolar concentration |
| Compound 2 | 100 | — |
| Compound 26 | 100 | — |
| PP2 | 45 | 47 |

The results shown in Table 11 demonstrated that compounds 2 and 26, two representative compounds of the invention, given by local (i.d.) administration, were both very potent inhibitor of CFA induced hyperalgesia, whereas the two comparators demonstrated to be less potent in this experimental paradigm.

Example 73

Pharmacokinetics

Compound 2 given to rats at 1 mg/kg orally exhibited an oral bioavailability of 51% and an AUC (0-24 h) of 877 ng*h/ml.

In comparison, under the same experimental conditions, PP2 showed a much lower oral bioavailability: AUC 160 ng*h/ml.

Therefore, the oral activity of Example 2 was examined in a model of induced osteoarthritis in the rat described in the next experiment.

Example 74

Surgically Induced Meniscal Tear Osteoarthritis in the Rat (MMT)

Male Sprague Dawley rats (Charles River) approximately 350 g body weight were used. Rats were anesthetized using 2.5% isoflurane in oxygen with a flow rate of 1 l per minute. The right hind leg was shaved and surgically prepared. The medial collateral ligament was exposed and transected. The meniscus was grasped with a hemostat and reflected proximally toward the femur. The meniscus was cut through its full thickness at the narrowest point. The connective tissue layer and the skin were closed with coated Vicryl 8-0 and 4-0 silk sutures, respectively. Sham operated animals underwent an identical procedure with the exception that the medial collateral ligament was exposed but not transected. After a recovery period of 2 weeks, mechanical hyperalgesia was evaluated for the following 4 weeks, once a week, before and 90 minutes after drugs administration. Pharmacological oral treatment was performed for 28 days, starting from 14 days after surgery. After 6 weeks from surgery, rats (ten animals per group) were sacrificed and the ipsilateral knee was removed for histopathological analysis. Compounds 2 of the invention at 10 and 30 mg/kg and PP2 at 10 mg/kg were given daily dissolved in saline at 5 ml/kg, orally.

The maximum possible effect (MPE %) was calculated by the following formula:

100*(Compound−Vehicle)/(Sham−Vehicle)

The results are shown in the following Table 12

TABLE 12

Pain behavior in a rat model of osteoarthritis

| | Days post-surgery/Pain threshold (g) | | | | | Pain threshold: MPE (%) | | | |
|---|---|---|---|---|---|---|---|---|---|
| Days post surgery)/ Groups | 14 | 21 | 28 | 35 | 42 | 21 | 28 | 35 | 42 |
| Sham | 485 | 465 | 443 | 403 | 377 | — | — | — | — |
| Vehicle | 315 | 275 | 288 | 293 | 277 | — | — | — | — |
| Compound 2 10 mg/kg | 308 | 333 | 323 | 313 | 298 | 30.5 | 22.6 | 18.2 | 21 |
| Compound 2 30 mg/kg | 305 | 358 | 343 | 335 | 320 | 44 | 35.5 | 38.2 | 43 |
| PP2 10 mg/kg | 285 | 278 | 267 | 262 | 253 | 1.8 | 0 | 0 | 0 |

Table 12 shows that the compound 2, the preferred compound of Formula (I) of the invention was able to reduce dose-dependently the pain behavior in a rat model of osteoarthritis, during the whole period of the treatment, five weeks, starting two weeks after the surgical MMT. On the contrary, PP2 the standard FYN kinase comparator was ineffective at 10 mg/kg, whereas its higher doses were not tolerated. It is also possible that this inactivity of PP2 is due to its poor oral absorption, as shown above in the paragraph pharmacokinetics.

The invention claimed is:

1. A compound of Formula (I):

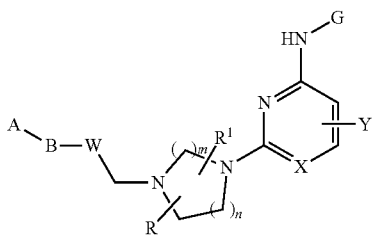

(I)

wherein:
A is selected from phenyl, 5-6 membered heterocyclic ring containing one or more hetero atoms selected from N, S and O and ($C_5$-$C_7$) cycloalkyl,
wherein said phenyl is optionally substituted with one or more substituents independently selected from halogen, trifluoromethyl, trifluoromethoxy, ($C_1$-$C_4$)alkyl, ($C_1$-$C_3$)alkoxy, ($C_3$-$C_6$)cycloalkyl, ($C_3$-$C_6$)cycloalkyloxy, nitro, amino, hydroxyl, cyano, carboxamide, sulfonamide, and methansulfonyl,
said 5-6 membered heterocyclic ring is a 5-6 membered heteroaryl optionally substituted with one or more substituents independently selected from halogen, trifluoromethyl, trifluoromethoxy, ($C_1$-$C_4$)alkyl, ($C_1$-$C_3$)alkoxy, ($C_3$-$C_6$)cycloalkyl, ($C_3$-$C_6$)cycloalkyloxy, nitro, amino, hydroxyl, cyano, carboxamide, sulfonamide, methansulfonyl, and 5-membered heterocyclic ring optionally substituted with ($C_1$-$C_3$)alkyl;
said ($C_5$-$C_7$)cycloalkyl is optionally substituted independently with one or two ($C_1$-$C_4$)alkyl;
B is independently selected from —CONH—, —NHCO—, —SO$_2$NH—, and —NHCONH—;
W is phenyl or heteroaryl group comprising one or two heteroatoms selected from N, O and S, said phenyl and said heteroaryl optionally substituted independently with one or two ($C_1$-$C_4$)alkyl, ($C^1$-$C_3$)alkoxy, ($C_3$-$C_6$) cycloalkyl, or ($C_3$-$C_6$)cycloalkyloxy;
R and $R^1$ independently are selected from a group consisting of H, ($C_1$-$C_3$)alkyl and ($C_1$-$C_3$)alkoxy;
m is 2;
n is 1;
X is N;
Y is independently selected from H, CH$_3$, CH$_2$—OH, and CN;
G is a 5-6 membered heteroaryl group, comprising one or more heteroatoms selected from N, O and S, and optionally substituted with one or more substituents independently selected from halogen, ($C_1$-$C_4$)alkyl, and ($C_3$-$C_6$)cycloalkyl,
or a pharmaceutically acceptable salt, thereof.

2. The compound of claim 1 wherein A is phenyl.

3. The compound of claim 2, wherein A is phenyl substituted with a substituent selected from halogen, ($C_1$-$C_4$) alkyl, ($C_1$-$C_3$)alkoxy, trifluoromethyl, trifluoromethoxy, and methansulfonyl.

4. The compound of claim 3 wherein A is phenyl substituted with trifluoromethyl.

5. The compound of claim 1, wherein A is selected from oxazole, pyridyl, imidazole, pyrazol and pyrazinyl, optionally substituted with trifluoromethyl, ($C_1$-$C_3$)alkyl, or trifluoromethoxy.

6. A compound of Formula (I):

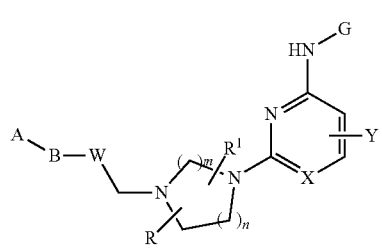

(I)

wherein:
A is a pyrrolidine, optionally substituted with methoxy,
B is independently selected from —CONH—, —NHCO—, —SO$_2$NH—, and —NHCONH—;
W is phenyl or heteroaryl group comprising one or two heteroatoms selected from N, O and S, said phenyl and said heteroaryl optionally substituted independently with one or two ($C_1$-$C_4$)alkyl, ($C_1$-$C_3$)alkoxy, ($C_3$-$C_6$)cycloalkyl, or ($C_3$-$C_6$)cycloalkyloxy;
R and $R^1$ independently are selected from a group consisting of H, ($C_1$-$C_3$)alkyl and ($C_1$-$C_3$)alkoxy;
m is 2;
n is 1;
X is N;

Y is independently selected from H, CH₃, CH₂—OH, and CN;

G is a 5-6 membered heteroaryl group, comprising one or more heteroatoms selected from N, O and S, and optionally substituted with one or more substituents independently selected from halogen, (C₁-C₄)alkyl, and (C₃-C₆)cycloalkyl, or a pharmaceutically acceptable salt, thereof.

7. The compound of claim 1, wherein A is cyclopentyl, optionally substituted with a (C₁-C₄)alkyl.

8. The compound according to claim 1 wherein G is 1-H-pyrazol.

9. The compound of claim 8 wherein G is 1-H pyrazol substituted with a cyclopropyl group.

10. A compound selected from the group consisting of
N-(4-((4-(45-cyclopropyl-1H-pyrazol-3-yl)amino)pyrimidin-2-yl)piperazin-1-yl)methyl)phenyl)benzamide
N-(4-((4-(45-cyclopropyl-1H-pyrazol-3-yl)amino)pyrimidin-2-yl)piperazin-1-yl)-methyl)phenyl)-2-(trifluoromethyl)benzamide
N-(4-((4-(45-cyclopropyl-1H-pyrazol-3-yl)amino)pyrimidin-2-yl)piperazin-1-yl)-methyl)phenyl)-2-fluorobenzamide
N-(4-((4-(45-cyclopropyl-1H-pyrazol-3-yl)amino)pyrimidin-2-yl)piperazin-1-yl)-methyl)phenyl)-2-methylbenzamide
2-chloro-N-(4-((4-(4-((5-cyclopropyl-1H-pyrazol-3-yl)amino)pyrimidin-2-yl)piperazin-1-yl)methyl)phenyl)benzamide
N-(4-(45-cyclopropyl-1H-pyrazol-3-yl)amino)pyrimidin-2-yl)piperazin-1-yl)-methyl)phenyl)-2-isopropylbenzamide
N-(4-((4-(45-cyclopropyl-1H-pyrazol-3-yl)amino)pyrimidin-2-yl)piperazin-1-yl)-methyl)phenyl)-2-methoxybenzamide
N-(4-((4-(45-cyclopropyl-1H-pyrazol-3-yl)amino)pyrimidin-2-yl)piperazin-1-yl)-methyl)phenyl)-2-(trifluoromethoxy)benzamide
N-(4-((4-(45-cyclopropyl-1H-pyrazol-3-yl)amino)pyrimidin-2-yl)piperazin-1-yl)-methyl)phenyl)-3-(trifluoromethyl)benzamide
N-(4-((4-(45-cyclopropyl-1H-pyrazol-3-yl)amino)pyrimidin-2-yl)piperazin-1-yl)-methyl)phenyl)-4-(trifluoromethyl)benzamide
N-(4-((4-(45-cyclopropyl-1H-pyrazol-3-yl)amino)pyrimidin-2-yl)piperazin-1-yl)-methyl)phenyl)-2,4-difluorobenzamide
N-(4-((4-(45-cyclopropyl-1H-pyrazol-3-yl)amino)pyrimidin-2-yl)piperazin-1-yl)-methyl)phenyl)-3-fluoro-2-(trifluoromethyl)benzamide
N-(4-((4-(45-cyclopropyl-1H-pyrazol-3-yl)amino)pyrimidin-2-yl)piperazin-1-yl)-methyl)phenyl)-2-fluoro-6-(trifluoromethyl)benzamide
N-(4-((4-(45-cyclopropyl-1H-pyrazol-3-yl)amino)pyrimidin-2-yl)piperazin-1-yl)-methyl)phenyl)-4-fluoro-2-(trifluoromethyl)benzamide
N-(4-((4-(45-cyclopropyl-1H-pyrazol-3-yl)amino)pyrimidin-2-yl)piperazin-1-yl)-methyl)phenyl)-2-methoxy-4-methylbenzamide
N-(4-((4-(45-cyclopropyl-1H-pyrazol-3-yl)amino)pyrimidin-2-yl)piperazin-1-yl)-methyl)phenyl)-3-(methylsulfonyl)benzamide
N-(4-((4-(45-cyclopropyl-1H-pyrazol-3-yl)amino)pyrimidin-2-yl)piperazin-1-yl)-methyl)-2-methylphenyl)-2-fluorobenzamide
N-(4-((4-(4-((5-cyclopropyl-1H-pyrazol-3-yl)amino)-6-methylpyrimidin-2-yl)piperazin-1-yl)methyl)-2-ethylphenyl)-2-fluorobenzamide
N-(4-((4-(4-((5-cyclopropyl-1H-pyrazol-3-yl)amino)-6-methylpyrimidin-2-yl)piperazin-1-yl)methyl)-3-ethylphenyl)-2-fluorobenzamide
N-(4-((4-(45-cyclopropyl-1H-pyrazol-3-yl)amino)pyrimidin-2-yl)piperazin-1-yl)-methyl)phenyl)-2-methyloxazole-4-carboxamide
N-(4-((4-(45-cyclopropyl-1H-pyrazol-3-yl)amino)pyrimidin-2-yl)piperazin-1-yl)-methyl)phenyl)-2-methyl-5-(trifluoromethyl)oxazole-4-carboxamide
N-(6-((4-(45-cyclopropyl-1H-pyrazol-3-yl)amino)pyrimidin-2-yl)piperazin-1-yl)-methyl)pyridin-3-yl)-2-methyl-5-(trifluoromethyl)oxazole-4-carboxamide
N-(4-((4-(45-cyclopropyl-1H-pyrazol-3-yl)amino)pyrimidin-2-yl)piperazin-1-yl)-methyl)phenyl)-3-methylisoxazole-4-carboxamide
N-(4-((4-(45-cyclopropyl-1H-pyrazol-3-yl)amino)pyrimidin-2-yl)piperazin-1-yl)-methyl)phenyl)picolinamide
N-(4-((4-(45-cyclopropyl-1H-pyrazol-3-yl)amino)pyrimidin-2-yl)piperazin-1-yl)-methyl)phenyl)-3-methylpicolinamide
N-(4-((4-(45-cyclopropyl-1H-pyrazol-3-yl)amino)pyrimidin-2-yl)piperazin-1-yl)-methyl)phenyl)-3-(trifluoromethyl)picolinamide
N-(4-((4-(45-cyclopropyl-1H-pyrazol-3-yl)amino)pyrimidin-2-yl)piperazin-1-yl)-methyl)phenyl)-2-(trifluoromethyl)nicotinamide
N-(4-((4-(45-cyclopropyl-1H-pyrazol-3-yl)amino)pyrimidin-2-yl)piperazin-1-yl)-methyl)phenyl)-2-methoxynicotinamide
N-(4-((4-(45-cyclopropyl-1H-pyrazol-3-yl)amino)pyrimidin-2-yl)piperazin-1-yl)-methyl)phenyl)-4-(trifluoromethyl)nicotinamide
(R)-N-(4-((4-(4-((5-cyclopropyl-1H-pyrazol-3-yl)amino)pyrimidin-2-yl)-2-methyl-piperazin-1-yl)methyl)phenyl)-2-(trifluoromethyl)nicotinamide
(S)-N-(4-((4-(4-((5-cyclopropyl-1H-pyrazol-3-yl)amino)pyrimidin-2-yl)-2-methyl-piperazin-1-yl)methyl)phenyl)-2-(trifluoromethyl)nicotinamide
N-(4-((4-(45-cyclopropyl-1H-pyrazol-3-yl)amino)pyrimidin-2-yl)piperazin-1-yl)-methyl)phenyl)-3-(trifluoromethyl)isonicotinamide
N-(4-((4-(45-cyclopropyl-1H-pyrazol-3-yl)amino)pyrimidin-2-yl)piperazin-1-yl)-methyl)phenyl)-1-methyl-3-(trifluoromethyl)-1H-pyrazol e-4-carboxamide
N-(4-((4-(45-cyclopropyl-1H-pyrazol-3-yl)amino)pyrimidin-2-yl)piperazin-1-yl)-methyl)phenyl)-1-methyl-1H-imidazole-2-carboxamide
N-(4-((4-(45-cyclopropyl-1H-pyrazol-3-yl)amino)pyrimidin-2-yl)piperazin-1-yl)-methyl)phenyl)pyrazine-2-carboxamide
N-(4-((4-(45-cyclopropyl-1H-pyrazol-3-yl)amino)pyrimidin-2-yl)piperazin-1-yl)-methyl)phenyl)-3-(trifluoromethyl)pyrazine-2-carboxamide
4-((4-(4-((5-cyclopropyl-1H-pyrazol-3-yl)amino)pyrimidin-2-yl)piperazin-1-yl)methyl)-N-(4-(trifluoromethoxy)phenyl)benzamide
4-((4-(4-((5-cyclopropyl-1H-pyrazol-3-yl)amino)pyrimidin-2-yl)piperazin-1-yl)methyl)-N-(3-(trifluoromethyl)phenyl)benzamide
4-((4-(4-((5-cyclopropyl-1H-pyrazol-3-yl)amino)pyrimidin-2-yl)piperazin-1-yl)methyl)-N-(4-(trifluoromethyl)phenyl)benzamide N-(4-((4-(45-cyclopropyl-1H-pyrazol-3-yl)amino)pyrimidin-2-yl)piperazin-1-yl)-methyl)phenyl)-2-fluorobenzenesulfonamide N-(5-((4-(445-cyclopropyl-1H-pyrazol-3-yl)amino)pyrimidin-2-yl)piperazin-1-yl)-methyl)pyrazin-2-yl)-2-(trifluoromethyl)benzamide N-(6-((4-(45-cyclopropyl-1H-pyrazol-3-yl)amino)pyrimidin-2-yl)piperazin-1-yl)-methyl)pyridazin-3-yl)-2-(trifluoromethyl)benzamide N-(6-((4-(45-cyclopropyl-1H-pyrazol-3-yl)amino)pyrimidin-2-yl)piperazin-1-yl)-methyl)pyridin-3-yl)-2-(trifluoromethyl)benzamide N-(4-((4-(4-((5-cyclopropyl-1,3,4-oxadiazol-2-yl)amino)pyrimidin-2-yl)pi perazin-1-yl)-methyl)phenyl)-2-(trifluoromethyl)benzamide N-(4-((4-(4-((4-methoxypyridin-2-yl)amino)pyrimidin-2-yl)piperazin-1-yl)methyl)-phenyl)-2-(trifluoromethyl)benzamide N-(4-((4-(4-((3-cyclopropyl-1H-pyrazol-5-yl)amino)-6-methylpyrimidin-2-yl)piperazin-1-yl)methyl)phenyl)-2-(trifluoromethyl)benzamide N-(4-((4-(4-((3-methyl-1H-pyrazol-5-yl)amino)pyrimidin-2-yl)piperazin-1-yl)methyl)-phenyl)-2-(trifluoromethyl)benzamide N-(4-((4-(4-((5-cyclopropyl-1H-pyrazol-3-yl)amino)pyrimidin-2-yl)piperazin-1-yl)-methyl)phenyl)-2-methyl-pyrrolidine-1-carboxamide and 1-cyclopentyl-3-(4-((4-(4-((3-cyclopropyl-1H-pyrazol-5-yl)amino)pyrimidin-2-yl)-piperazin-1-yl)methyl)phenyl)urea.

11. The compound according to claim 10 selected from the group consisting of N-(4-((4-(4-((5-cyclopropyl-1H-pyrazol-3-yl)amino)pyrimidin-2-yl)piperazin-1-yl)-methyl)phenyl)-2-(trifluoromethyl)benzamide and N-(4-((4-(4-((5-cyclopropyl -1H-pyrazol-3-yl)amino)pyrimidin-2-yl)piperazin-1-yl)-methyl)phenyl)-3-(trifluoromethyl)picolinamide.

12. A pharmaceutical composition comprising a compound of claim 1 or a pharmaceutically acceptable salt thereof and a pharmaceutically acceptable carrier.

13. A compound of Formula (I) or a pharmaceutically acceptable salt thereof according to claim 1 for the use in the inhibition of a FYN kinase.

14. A compound of Formula (I) or a pharmaceutically acceptable salt thereof according to claim 1, for use in the treatment of a FYN kinase-mediated disease or disorder.

15. The compound for use of claim 14, wherein the FYN kinase-mediated disease or disorder is arthritis, osteoarthritis, rheumatoid arthritis, psoriatic arthritis, acute and chronic pain, osteoarthritis, rheumatoid arthritis pain, postoperative pain, visceral pain, pain associated with cancer, trigeminal neuralgia, diabetic neuropathy acute and chronic pain, or muscular pain.

* * * * *

UNITED STATES PATENT AND TRADEMARK OFFICE
CERTIFICATE OF CORRECTION

PATENT NO. : 10,125,121 B2
APPLICATION NO. : 15/559341
DATED : November 13, 2018
INVENTOR(S) : Artusi et al.

It is certified that error appears in the above-identified patent and that said Letters Patent is hereby corrected as shown below:

In the Claims

Claim 1, at Column 70, Line 5, insert --a-- before "5-membered"

Claim 1, at Column 70, Line 14, delete "C¹" and insert --$C_1$--

Claim 10, at Column 71, Line 16, delete "N-(4-((4-(45-cyclopropyl-1H-pyrazol-3-yl)amino)pyrimidin-2-yl)piperazin-1-yl)methyl)phenyl)benzamide" and insert --N-(4-((4-(4-((5-cyclopropyl-1H-pyrazol-3-yl)amino)pyrimidin-2-yl)piperazin-1-yl)methyl)phenyl)benzamide--

Claim 10, at Column 71, Line 18, delete "N-(4-((4-(45-cyclopropyl-1H-pyrazol-3-yl)amino)pyrimidin-2-yl)piperazin-1-yl)-methyl)phenyl)-2-(trifluoromethyl)benzamide" and insert --N-(4-((4-(4-((5-cyclopropyl-1H-pyrazol-3-yl)amino)pyrimidin-2-yl)piperazin-1-yl)methyl)phenyl)-2-(trifluoromethyl)benzamide--

Claim 10, at Column 71, Line 21, delete "N-(4-((4-(45-cyclopropyl-1H-pyrazol-3-yl)amino)pyrimidin-2-yl)piperazin-1-yl)-methyl)phenyl)-2-fluorobenzamide" and insert --N-(4-((4-(4-((5-cyclopropyl-1H-pyrazol-3-yl)amino)pyrimidin-2-yl)piperazin-1-yl)methyl)phenyl)-2-fluorobenzamide--

Claim 10, at Column 71, Line 24, delete "N-(4-((4-(45-cyclopropyl-1H-pyrazol-3-yl)amino)pyrimidin-2-yl)piperazin-1-yl)-methyl)phenyl)-2-methylbenzamide" and insert --N-(4-((4-(4-((5-cyclopropyl-1H-pyrazol-3-yl)amino)pyrimidin-2-yl)piperazin-1-yl)methyl)phenyl)-2-methylbenzamide--

Claim 10, at Column 71, Line 30, delete "N-(4-((4-(45-cyclopropyl-1H-pyrazol-3-yl)amino)pyrimidin-2-yl)piperazin-1-yl)-methyl)phenyl)-2-isopropylbenzamide" and insert --N-(4-((4-(4-((5-cyclopropyl-1H-pyrazol-3-yl)amino)pyrimidin-2-yl)piperazin-1-yl)methyl)phenyl)-2-isopropylbenzamide--

Signed and Sealed this
Second Day of July, 2019

Andrei Iancu
*Director of the United States Patent and Trademark Office*

CERTIFICATE OF CORRECTION (continued)
U.S. Pat. No. 10,125,121 B2

Claim 10, at Column 71, Line 33, delete "N-(4-((4-(45-cyclopropyl-1H-pyrazol-3-yl)amino)pyrimidin-2-yl)piperazin-1-yl)-methyl)phenyl)-2-methoxybenzamide" and insert --N-(4-((4-(4-((5-cyclopropyl-1H-pyrazol-3-yl)amino)pyrimidin-2-yl)piperazin-1-yl)methyl)phenyl)-2-methoxybenzamide--

Claim 10, at Column 71, Line 36, delete "N-(4-((4-(45-cyclopropyl-1H-pyrazol-3-yl)amino)pyrimidin-2-yl)piperazin-1-yl)-methyl)phenyl)-2-(trifluoromethoxy)benzamide" and insert --N-(4-((4-(4-((5-cyclopropyl-1H-pyrazol-3-yl)amino)pyrimidin-2-yl)piperazin-1-yl)methyl)phenyl)-2-(trifluoromethoxy)benzamide--

Claim 10, at Column 71, Line 39, delete "N-(4-((4-(45-cyclopropyl-1H-pyrazol-3-yl)amino)pyrimidin-2-yl)piperazin-1-yl)-methyl)phenyl)-3-(trifluoromethyl)benzamide" and insert --N-(4-((4-(4-((5-cyclopropyl-1H-pyrazol-3-yl)amino)pyrimidin-2-yl)piperazin-1-yl)methyl)phenyl)-3-(trifluoromethyl)benzamide--

Claim 10, at Column 71, Line 42, delete "N-(4-((4-(45-cyclopropyl-1H-pyrazol-3-yl)amino)pyrimidin-2-yl)piperazin-1-yl)-methyl)phenyl)-4-(trifluoromethyl)benzamide" and insert --N-(4-((4-(4-((5-cyclopropyl-1H-pyrazol-3-yl)amino)pyrimidin-2-yl)piperazin-1-yl)methyl)phenyl)-4-(trifluoromethyl)benzamide--

Claim 10, at Column 71, Line 45, delete "N-(4-((4-(45-cyclopropyl-1H-pyrazol-3-yl)amino)pyrimidin-2-yl)piperazin-1-yl)-methyl)phenyl)-2,4-difluorobenzamide" and insert --N-(4-((4-(4-((5-cyclopropyl-1H-pyrazol-3-yl)amino)pyrimidin-2-yl)piperazin-1-yl)methyl)phenyl)-2,4-difluorobenzamide--

Claim 10, at Column 71, Line 48, delete "N-(4-((4-(45-cyclopropyl-1H-pyrazol-3-yl)amino)pyrimidin-2-yl)piperazin-1-yl)-methyl)phenyl)-3-fluoro-2-(trifluoromethyl)benzamide" and insert --N-(4-((4-(4-((5-cyclopropyl-1H-pyrazol-3-yl)amino)pyrimidin-2-yl)piperazin-1-yl)methyl)phenyl)-3-fluoro-2-(trifluoromethyl)benzamide--

Claim 10, at Column 71, Line 51, delete "N-(4-((4-(45-cyclopropyl-1H-pyrazol-3-yl)amino)pyrimidin-2-yl)piperazin-1-yl)-methyl)phenyl)-2-fluoro-6-(trifluoromethyl)benzamide" and insert --N-(4-((4-(4-((5-cyclopropyl-1H-pyrazol-3-yl)amino)pyrimidin-2-yl)piperazin-1-yl)methyl)phenyl)-2-fluoro-6-(trifluoromethyl)benzamide--

Claim 10, at Column 71, Line 54, delete "N-(4-((4-(45-cyclopropyl-1H-pyrazol-3-yl)amino)pyrimidin-2-yl)piperazin-1-yl)-methyl)phenyl)-4-fluoro-2-(trifluoromethyl)benzamide" and insert --N-(4-((4-(4-((5-cyclopropyl-1H-pyrazol-3-yl)amino)pyrimidin-2-yl)piperazin-1-yl)methyl)phenyl)-4-fluoro-2-(trifluoromethyl)benzamide--

Claim 10, at Column 71, Line 57, delete "N-(4-((4-(45-cyclopropyl-1H-pyrazol-3-yl)amino)pyrimidin-2-yl)piperazin-1-yl)-methyl)phenyl)-2-methoxy-4-methylbenzamide" and insert --N-(4-((4-(4-((5-cyclopropyl-1H-pyrazol-3-yl)amino)pyrimidin-2-yl)piperazin-1-yl)methyl)phenyl)-2-methoxy-4-methylbenzamide--

CERTIFICATE OF CORRECTION (continued)
U.S. Pat. No. 10,125,121 B2

Claim 10, at Column 71, Line 60, delete "N-(4-((4-(45-cyclopropyl-1H-pyrazol-3-yl)amino)pyrimidin-2-yl)piperazin-1-yl)-methyl)phenyl)-3-(methylsulfonyl)benzamide" and insert --N-(4-((4-(4-((5-cyclopropyl-1H-pyrazol-3-yl)amino)pyrimidin-2-yl)piperazin-1-yl)methyl)phenyl)-3-(methylsulfonyl)benzamide--

Claim 10, at Column 71, Line 63, delete "N-(4-((4-(45-cyclopropyl-1H-pyrazol-3-yl)amino)pyrimidin-2-yl)piperazin-1-yl)-methyl)-2-methylphenyl)-2-fluorobenzamide" and insert --N-(4-((4-(4-((5-cyclopropyl-1H-pyrazol-3-yl)amino)pyrimidin-2-yl)piperazin-1-yl)methyl)-2-methylphenyl)-2-fluorobenzamide--

Claim 10, at Column 72, Line 7, delete "N-(4-((4-(45-cyclopropyl-1H-pyrazol-3-yl)amino)pyrimidin-2-yl)piperazin-1-yl)-methyl)phenyl)-2-methyloxazole-4-carboxamide" and insert --N-(4-((4-(4-((5-cyclopropyl-1H-pyrazol-3-yl)amino)pyrimidin-2-yl)piperazin-1-yl)methyl)phenyl)-2-methyloxazole-4-carboxamide--

Claim 10, at Column 72, Line 10, delete "N-(4-((4-(45-cyclopropyl-1H-pyrazol-3-yl)amino)pyrimidin-2-yl)piperazin-1-yl)-methyl)phenyl)-2-methyl-5-(trifluoromethyl)oxazole-4-carboxamide" and insert --N-(4-((4-(4-((5-cyclopropyl-1H-pyrazol-3-yl)amino)pyrimidin-2-yl)piperazin-1-yl)methyl)phenyl)-2-methyl-5-(trifluoromethyl)oxazole-4-carboxamide--

Claim 10, at Column 72, Line 13, delete "N-(6-((4-(45-cyclopropyl-1H-pyrazol-3-yl)amino)pyrimidin-2-yl)piperazin-1-yl)methyl)pyridin-3-yl)-2-methyl-5-(trifluoromethyl)oxazole-4-carboxamide" and insert --N-(6-((4-(4-((5-cyclopropyl-1H-pyrazol-3-yl)amino)pyrimidin-2-yl)piperazin-1-yl)methyl)pyridin-3-yl)-2-methyl-5-(trifluoromethyl)oxazole-4-carboxamide--

Claim 10, at Column 72, Line 16, delete "N-(4-((4-(45-cyclopropyl-1H-pyrazol-3-yl)amino)pyrimidin-2-yl)piperazin-1-yl)-methyl)phenyl)-3-methyl-isoxazole-4-carboxamide" and insert --N-(4-((4-(4-((5-cyclopropyl-1H-pyrazol-3-yl)amino)pyrimidin-2-yl)piperazin-1-yl)methyl)phenyl)-3-methyl-isoxazole-4-carboxamide--

Claim 10, at Column 72, Line 19, delete "N-(4-((4-(45-cyclopropyl-1H-pyrazol-3-yl)amino)pyrimidin-2-yl)piperazin-1-yl)-methyl)phenyl)picolinamide" and insert --N-(4-((4-(4-((5-cyclopropyl-1H-pyrazol-3-yl)amino)pyrimidin-2-yl)piperazin-1-yl)methyl)phenyl)picolinamide--

Claim 10, at Column 72, Line 22, delete "N-(4-((4-(45-cyclopropyl-1H-pyrazol-3-yl)amino)pyrimidin-2-yl)piperazin-1-yl)-methyl)phenyl)-3-methyl-picolinamide" and insert --N-(4-((4-(4-((5-cyclopropyl-1H-pyrazol-3-yl)amino)pyrimidin-2-yl)piperazin-1-yl)-methyl)phenyl)-3-methylpicolinamide--

Claim 10, at Column 72, Line 25, delete "N-(4-((4-(45-cyclopropyl-1H-pyrazol-3-yl)amino)pyrimidin-2-yl)piperazin-1-yl)-methyl)phenyl)-3-(trifluoromethyl)picolinamide" and insert --N-(4-((4-(4-((5-cyclopropyl-1H-pyrazol-3-yl)amino)pyrimidin-2-yl)piperazin-1-yl)methyl)phenyl)-3-(trifluoromethyl)picolinamide--

CERTIFICATE OF CORRECTION (continued)
U.S. Pat. No. 10,125,121 B2

Claim 10, at Column 72, Line 28, delete "N-(4-((4-(45-cyclopropyl-1H-pyrazol-3-yl)amino)pyrimidin-2-yl)piperazin-1-yl)-methyl)phenyl)-2-(trifluoromethyl)nicotinamide" and insert --N-(4-((4-(4-((5-cyclopropyl-1H-pyrazol-3-yl)amino)pyrimidin-2-yl)piperazin-1-yl)methyl)phenyl)-2-(trifluoromethyl)nicotinamide--

Claim 10, at Column 72, Line 31, delete "N-(4-((4-(45-cyclopropyl-1H-pyrazol-3-yl)amino)pyrimidin-2-yl)piperazin-1-yl)-methyl)phenyl)-2-methoxynicotinamide" and insert --N-(4-((4-(4-((5-cyclopropyl-1H-pyrazol-3-yl)amino)pyrimidin-2-yl)piperazin-1-yl)methyl)phenyl)-2-methoxynicotinamide--

Claim 10, at Column 72, Line 33, delete "N-(4-((4-(45-cyclopropyl-1H-pyrazol-3-yl)amino)pyrimidin-2-yl)piperazin-1-yl)-methyl)phenyl)-4-(trifluoromethyl)nicotinamide" and insert --N-(4-((4-(4-((5-cyclopropyl-1H-pyrazol-3-yl)amino)pyrimidin-2-yl)piperazin-1-yl)methyl)phenyl)-4-(trifluoromethyl)nicotinamide--

Claim 10, at Column 72, Line 42, delete "N-(4-((4-(45-cyclopropyl-1H-pyrazol-3-yl)amino)pyrimidin-2-yl)piperazin-1-yl)-methyl)phenyl)-3-(trifluoromethyl)isonicotinamide" and insert --N-(4-((4-(4-((5-cyclopropyl-1H-pyrazol-3-yl)amino)pyrimidin-2-yl)piperazin-1-yl)methyl)phenyl)-3-(trifluoromethyl)isonicotinamide--

Claim 10, at Column 72, Line 45, delete "N-(4-((4-(45-cyclopropyl-1H-pyrazol-3-yl)amino)pyrimidin-2-yl)piperazin-1-yl)-methyl)phenyl)-1-methyl-3-(trifluormethyl)-1H-pyrazole-4-carboxamide" and insert --N-(4-((4-(4-((5-cyclopropyl-1H-pyrazol-3-yl)amino)pyrimidin-2-yl)piperazin-1-yl)methyl)phenyl)-1-methyl-3-(trifluormethyl)-1H-pyrazole-4-carboxamide--

Claim 10, at Column 72, Line 48, delete "N-(4-((4-(45-cyclopropyl-1H-pyrazol-3-yl)amino)pyrimidin-2-yl)piperazin-1-yl)-methyl)phenyl)-1-methyl-1H-imidazole-2-carboxamide" and insert --N-(4-((4-(4-((5-cyclopropyl-1H-pyrazol-3-yl)amino)pyrimidin-2-yl)piperazin-1-yl)methyl)phenyl)-1-methyl-1H-imidazole-2-carboxamide--

Claim 10, at Column 72, Line 51, delete "N-(4-((4-(45-cyclopropyl-1H-pyrazol-3-yl)amino)pyrimidin-2-yl)piperazin-1-yl)-methyl)phenyl)pyrazine-2-carboxamide" and insert --N-(4-((4-(4-((5-cyclopropyl-1H-pyrazol-3-yl)amino)pyrimidin-2-yl)piperazin-1-yl)methyl)phenyl)pyrazine-2-carboxamide--

Claim 10, at Column 72, Line 54, delete "N-(4-((4-(45-cyclopropyl-1H-pyrazol-3-yl)amino)pyrimidin-2-yl)piperazin-1-yl)-methyl)phenyl)-3-(trifluoromethyl)pyrazine-2-carboxamide" and insert --N-(4-((4-(4-((5-cyclopropyl-1H-pyrazol-3-yl)amino)pyrimidin-2-yl)piperazin-1-yl)methyl)phenyl)-3-(trifluoromethyl)pyrazine-2-carboxamide--

Claim 10, at Column 73, Line 1, delete "N-(4-((4-(45-cyclopropyl-1H-pyrazol-3-yl)amino)pyrimidin-2-yl)piperazin-1-yl)-methyl)phenyl)-2-fluorobenzenesulfonamide" and insert --N-(4-((4-(4-((5-cyclopropyl-1H-pyrazol-3-yl)amino)pyrimidin-2-yl)piperazin-1-yl)methyl)phenyl)-2-fluorobenzenesulfonamide--

CERTIFICATE OF CORRECTION (continued)
U.S. Pat. No. 10,125,121 B2

Claim 10, at Column 73, Line 4, delete "N-(5-((4-(445-cyclopropyl-1H-pyrazol-3-yl)amino)pyrimidin-2-yl)piperazin-1-yl)-methyl)pyrazine-2-yl)-2-(trifluoromethyl)benzamide" and insert --N-(5-((4-(4-((5-cyclopropyl-1H-pyrazol-3-yl)amino)pyrimidin-2-yl)piperazin-1-yl)-methyl)pyrazine-2-yl)-2-(trifluoromethyl)benzamide--

Claim 10, at Column 73, Line 7, delete "N-(6-((4-(45-cyclopropyl-1H-pyrazol-3-yl)amino)pyrimidin-2-yl)piperazin-1-yl)-methyl)pyridazin-3-yl)-2-(trifluoromethyl)benzamide" and insert --N-(6-((4-(4-((5-cyclopropyl-1H-pyrazol-3-yl)amino)pyrimidin-2-yl)piperazin-1-yl)methyl)pyridazin-3-yl)-2-(trifluoromethyl)benzamide--

Claim 10, at Column 73, Line 10, delete "N-(6-((4-(45-cyclopropyl-1H-pyrazol-3-yl)amino)pyrimidin-2-yl)piperazin-1-yl)-methyl)pyridin-3-yl)-2-(trifluoromethyl)benzamide" and insert --N-(6-((4-(4-((5-cyclopropyl-1H-pyrazol-3-yl)amino)pyrimidin-2-yl)piperazin-1-yl)methyl)pyridin-3-yl)-2-(trifluoromethyl)benzamide--

Claim 10, at Column 73, Line 13, delete "N-(4-((4-(4-((5-cyclopropyl-1,3,4-oxadiazol-2-yl)amino)pyrimidin-2-yl)pi perazin-1-yl)-methyl)phenyl)-2-(trifluoromethyl)benzamide" and insert --N-(4-((4-(4-((5-cyclopropyl-1,3,4-oxadiazol-2-yl)amino)pyrimidin-2-yl)piperazin-1-yl)-methyl)phenyl)-2-(trifluoromethyl)benzamide--